(12) United States Patent
Williams et al.

(10) Patent No.: US 9,186,402 B2
(45) Date of Patent: *Nov. 17, 2015

(54) METHOD FOR PREPARING LARGAZOLE ANALOGS AND USES THEREOF

(71) Applicants: Colorado State University Research Foundation, Fort Collins, CO (US); Dana-Farber Cancer Institute, Inc., Boston, MA (US); University of Notre Dame du Lac, Notre Dame, IN (US)

(72) Inventors: Robert M. Williams, Fort Collins, CO (US); James E. Bradner, Cambridge, MA (US); Albert Bowers, Boston, MA (US); Tenaya Newkirk, Fort Collins, CO (US); Olaf G. Wiest, Notre Dame, IN (US)

(73) Assignees: Colorado State University Research University, Fort Collins, CO (US); Dana-Farber Cancer Institute, Inc., Boston, MA (US); University of Notre Dame du Lac, Notre Dame, IN (US)

( * ) Notice: Subject to any disclaimer, the term of this patent is extended or adjusted under 35 U.S.C. 154(b) by 205 days.

This patent is subject to a terminal disclaimer.

(21) Appl. No.: 13/944,446

(22) Filed: Jul. 17, 2013

(65) Prior Publication Data

US 2014/0093449 A1    Apr. 3, 2014

Related U.S. Application Data

(60) Continuation of application No. 13/490,693, filed on Jun. 7, 2012, now Pat. No. 8,513,290, which is a division of application No. 12/504,508, filed on Jul. 16, 2009, now Pat. No. 8,217,076.

(60) Provisional application No. 61/151,087, filed on Feb. 9, 2009, provisional application No. 61/081,653, filed on Jul. 17, 2008.

(51) Int. Cl.
| | |
|---|---|
| *C07D 513/18* | (2006.01) |
| *C07D 513/22* | (2006.01) |
| *C07D 498/18* | (2006.01) |
| *A61K 39/395* | (2006.01) |
| *A61K 31/429* | (2006.01) |

(52) U.S. Cl.
CPC ......... *A61K 39/39558* (2013.01); *A61K 31/429* (2013.01); *C07D 498/18* (2013.01); *C07D 513/18* (2013.01)

(58) Field of Classification Search
CPC .. C07D 513/22; C07D 513/18; C07D 498/18; A61K 31/429
See application file for complete search history.

(56) References Cited

U.S. PATENT DOCUMENTS

| | | | |
|---|---|---|---|
| 4,456,592 | A | 6/1984 | Okumura et al. |
| 5,846,933 | A | 12/1998 | Korngold et al. |
| 6,509,315 | B1 | 1/2003 | Joullie et al. |
| 2005/0119169 | A1 | 6/2005 | Deslongchamps et al. |
| 2007/0129289 | A1 | 6/2007 | Joullie et al. |

FOREIGN PATENT DOCUMENTS

| | | |
|---|---|---|
| JP | 03-141296 | 6/1991 |
| WO | WO 2007/061939 | 5/2007 |
| WO | WO 2007/100385 | 9/2007 |
| WO | WO 2009/032352 | 3/2009 |

OTHER PUBLICATIONS

Avenoza A., et al. (2001) Tetrahedron: Asymmetry 12(6):949-957 "Enantioselective synthesis of (S)- and (R)-methylserines: application to the synthesis of (S)- and (R)-N-Boc-N,O-isopropylidene-a-methylserinals".
Berge, et al. (1977) J. Pharm. Sci. 66:1-19 "Pharmaceutical salts".
Bolden, J. E., et al. (2006) Nat. Rev. Drug Discovery 5:769-784 "Anticancer activities of histone deacetylase inhibitors".
Bowers, A.A., et al. (2008) J Am Chem Soc 130:11219-22 Total "Synthesis and Biological Mode of Action of Largazole: A Potent Class I Histone Deacetylase Inhibitor".
Bowers, A.A., et al. (2009) Org. Letters 11(6) 1301-1304 "Synthesis and Histone Deacetylase Inhibitory Activity of Largazole Analogs: Alteration of the Zinc-Binding Domain and Macrocyclic Scaffold".
Bradner (2010) Nat. Chem Biol. 6(3):238-243, "Chemical Phylogenetics of Histone Deacetylases".
Burger's Medicinal Chemistry and Drug Discovery (1995, Manfred E. Wolff ed., 5th ed. 172-178, 929-932).
Chen, Y., et al. (2003) J Org Chem 68:8902-8905 "Total Synthesis of the Depsipeptide FR-901375".
Cleve, Trip Report for 9th Tetrahedron Symposium, Berkeley, CA Klos, Jul. 22-25, 2008, "Discovery and Optimization of Diamine Analogues as Potent Inhibitors of Leukotriene A4 Hydrolase."
Freireich, et al. (1966) Cancer Chemother Rep 50:219 "Quantitative comparison to toxicity of anticancer agents in mouse, rat, hamster, dog, monkey and man".
Furumai, R., et al. (2001) PNAS USA 98:87-92 "Potent Histone Deacetylase Inhibitors Built From Trichostatin A and Cyclic Tetrapeptide Antibiotics Including Trapoxin".

(Continued)

*Primary Examiner* — Sreeni Padmanabhan
*Assistant Examiner* — Sahar Javanmard
(74) *Attorney, Agent, or Firm* — Swanson & Bratschun, L.L.C.

(57) ABSTRACT

Analogs of largazole are described herein. Methods of treating cancer and blood disorders using largazole and largazole analogs and pharmaceutical compositions comprising the same are additionally described herein. Methods for preparing largazole analogs are likewise described.

11 Claims, 5 Drawing Sheets

(56) References Cited

OTHER PUBLICATIONS

Ghosh, A.K. & Kulkarni, S. (2008) Org. Lett. 10:3907-3909 "Enantioselective Total Synthesis of (+)-Largazole, a Potent Inhibitor of Histone Deacetylase".
Greshock, et al. (2008) Org Lett 10:613-616 "Improved Total Synthesis of the Potent HDAC Inhibitor FK228 (FR-901228)".
Grozinger, C.M., et al. (1999) Proc. Nat. Acad. Sci. USA 96:4868-4873 "Three proteins define a class of human histone deacetylases related to yeast Hdalp".
Handbook of Pharmaceutical Salts. Properties, Selection, and Use (P. Heinrich Stahl and C. Wermuth, Eds., Verlag Helvetica Chica Acta, Zurich, Switzerland (2002)).
International Search Report and Written Opinion dated Sep. 28, 2009 for corresponding PCT Application No. PCT/US09/50878.
Jeanguenat, A. & Seebach, D. (1991) J Chem Soc, Perkins Trans 1:2291-2298 "Stereoselective chain elongation at C-3 of cysteine through 2,3-dihydrothiazoles, without racemization. Preparation of 2-amino-5-hydroxy-3-mercaptoalkanoic acid derivatives".
Johnstone, R.W. (2002) Nature Rev. Drug Disc. 1:287-299 "Histone deacetylase inhibitors: novel drugs for the treatment of cancer".
Katsura, Y., et al. (1994) J Med Chem 37(1):57-66 "Studies on anti-ulcer drugs. 7. 2-Guanidino-4-pyridylthiazoles as histamine H2-receptor antagonists with potent gastroprotective effects against nonsteroidal antiinflammatory drug-induced injury".
Lange, U.E.W., et al. (1999) Tetrahedron Lett. 40:7067-7070 "A new mild method for the synthesis of amidines".
Li, K.W., et al. (1996) J Am Chem Soc 118:7237-7238 "Total Synthesis of the Antitumor depsipeptide FR-901, 228".
Marsault, et al. (2006) Journal of Medicinal Chemistry pp. C-D "Discovery of a New Class of Macrocyclic Antagonists to the Human Motilin Receptor."
Masuoka, Y., et al. (2001) Tetrahedron Lett. 42:41-44 "Spiruchostatins A and B, novel gene expression-enhancing substances produced by Pseudomonas sp.".
Miller, T. A., et al. (2003) J. Med. Chem. 46:5097-5116 "Histone deacetylase inhibitors".
Minucci, S., et al. (2006) Nature Rev. Cancer 6:38-51 "Histone deacetylase inhibitors and the promise of epigenetic (and more) treatments for cancer".
Moradei, O., et al. (2005) Curr. Med. Chem. Anti-Cancer Agents 5:529-560 "Histone deacetylase inhibitors: latest developments, trends and prospects".
Mulqueen, G.C., et al. (1993) Tetrahedron 49:5359-5364 "Synthesis of the thiazoline-based siderophore (S)-desferrithiocin".
Nasveschuk, C.G., et al. (2008) Org. Lett. 10:3595-3598 "A Concise Total Synthesis of Largazole, Solution Structure, and Some Preliminary Structure Activity Relationships".
Nishino, N., et al. (2003) Org Lett 5:5079-5082 "cyclic tetrapeptides bearing a sulfhydryl group potently inhibit histone deacetylases".
Patani and LaVoie (1996) Chem. Rev. 96:3147-3176 "Bioisosterism: A Rational Approach in Drug Design".
Phillips, A.J., et al. (2000) Org Lett 2(8):1165-1168 "Synthesis of Functionalized Oxazolines and Oxazoles with DAST and Deoxo-Fluor".
Reiner, J., et al. (2002) Bioorg Med Chem Lett 12(8):1203-1208 "Non-covalent thrombin inhibitors featuring p3-heterocycles with P1-monocyclic arginine surrogates".
Scientific Tables, Geigy Pharmaceuticals, Ardley, N.Y., (1970) 537.
Seiser, T.; et al. (2008) Angew. Chem. Int. Ed. 47:6483-6485 "Synthesis and Biological Activity of Largazole and Derivatives".
Shigematsu, N., et al. (1994) J. Antibiot. 47:311-314 "A novel antitumor bicycle depsipeptide produced by Chromobacterium violaceum No. 968".
Smith, N.D. and Goodman, M. (2003) Org. Lett. 5:1035-1037 "Enantioselective synthesis of alpha-methyl-D-cysteine and lanthionine building blocks via alpha-methyl-D-serine-beta-lactone".
Somech, R., et al. (2004) Cancer Treat. Rev. 30:461 "Histone deacetylase inhibitors—a new tool to treat cancer".
Taori, K., et al. (2008) J. Am. Chem. Soc. 130:1806-1807 and 13506 "Structure and Activity of Largazole, a Potent Antiproliferative Agent from the Floridian Marine Cyanobacterium Symploca sp."
Taunton, J., et al. (1996) Science 272:408-411 "A Mammalian Histone Deacetylase Related to the Yeast Transcriptional Regulator Rpd3p".
Townsend, P.A., et al. (2007) The bicyclic depsipeptide family of histone deacetylase inhibitors, in Chemical Biology; Schreiber, S.L., et al. Eds.Wiley-VCH Verlag GmbH & Co. 693-720.
Ueda, H., et al. (1994) J. Antibiot. 47:315-323 "FR901228, a novel antitumor bicyclic depsipeptide produced by Chromobacterium violaceum No. 968 III. Antitumor activities on experimental tumors in mice".
Ueda, H., et al. (1994) J. Antibiot. 47:301-310 "FR901228, a novel antitumor bicyclic depsipeptide produced by Chromobacterium violaceum No. 968 I. Taxonomy, fermentation, isolation, physicochemical and biological properties, and antitumor activity".
Vanommeslaeghe, K., et al. (2005) Bioorg. Med. Chem. 13:3987-3992 "Theoretical study revealing the functioning of a novel combination of catalytic motives in Histone Deacetylase".
Vanommeslaeghe, K., et al. (2005) Bioorg. Med. Chem. 13:6070-6082 "DFT-based Ranking of Zink-chelating Groups in Histone Deacetylase Inhibitors".
Videnov, G., et al. (1996) Angew Chem Int Ed Eng 35:1503-1506 "Synthesis of Naturally Occurring, Conformationally Restricted Oxazole and Thiazole Containing Di- and Tripeptide Mimetics".
Ying, Y., et al. (2008) J. Am. Chem. Soc. 130:8455-8459 "Total Synthesis and Molecular Target of Largazole, a Histone Deacetylase Inhibitor".
Ying, Y., et al. (2008) Organic Letters 10(18):4021-4024 "Synthesis and Activity of Largazole Analogues with Linker and Macrocycle Modification".
Yoshida, M., et al. (1990) J. Antibiot. 43:1101-1106 "Structural Specificity for Biological Activity of Trichostatin A, A Specific Inhibitor of Mammalian Cell Cycle with Potent Differentiation-Inducing Activity in Friend Leukemia Cells".
Yoshida, M., et al. (1990) *J. Biol. Chem.* 265:17174 "Potent and specific inhibition of mammalian histone deacetylase both in vivo and in vitro by trichostatin A".
Yurek-George, A. (2007) J. Med. Chem. 50:5720-5726 "The First Biologically Active Synthetic Analogues of FK228, the Depsipeptide Histone Deacetylase Inhibitor".
Yurek-George, A., et al. (2004) J Am Chem Soc 126:1030-1031 "Total synthesis of spiruchostatin A, a potent histone deacetylase inhibitor".

METHOD FOR PREPARING LARGAZOLE ANALOGS AND USES THEREOF

CROSS-REFERENCE TO RELATED APPLICATIONS/PATENTS & INCORPORATIONS BY REFERENCE

This application is a continuation of U.S. patent application Ser. No. 13/490,693, filed Jun. 7, 2012, now U.S. Pat. No. 8,217,076, which is a divisional of U.S. patent application Ser. No. 12/504,508, filed Jul. 16, 2009, each entitled entitled "Method for Preparing Largazole Analogs and Uses Thereof" which claims priority from U.S. Provisional Patent Application Ser. No. 61/081,653, filed on Jul. 17, 2008, entitled "Method for Preparing Largazole and Largazole Thiol and Uses and Analogs Thereof" and 61/151,087, filed on Feb. 9, 2009, entitled "Method for Preparing Largazole Analogs and Uses Thereof," which are hereby incorporated by reference in their entirety.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

STATEMENT OF RIGHTS TO INVENTIONS MADE UNDER FEDERALLY SPONSORED RESEARCH

This work was supported by the government, in part, by grants from the National Institutes of Health and National Cancer Institute (CA136283, GM49631, and 1K08 CA128972-01A1) and the National Cancer Institute's Initiative for Chemical Genetics of the National Institutes of Health (N01-CO-12400). Thus, the government has certain rights to this invention.

BACKGROUND OF THE INVENTION

Largazole (1) is a densely functionalized macrocyclic depsipeptide, recently isolated from the cyanobacterium Symploca sp. (Taori, K., et al. 2008 *J. Am. Chem. Soc.* 130:1806-1807 and 13506; Ying, Y., et al. 2008 *J. Am. Chem. Soc.* 130). This natural product exhibits exceptionally potent and selective biological activity, with two- to ten-fold differential growth inhibition in a number of transformed and non-transformed human- and murine-derived cell lines. The remarkable selectivity of this agent against cancer cells prompts particular interest in its mode of action and its value as a potential cancer chemotherapeutic.

It has previously been stated that "the 3-hydroxy-7-mercaptohept-4-enoic acid unit in 1 is unprecedented in natural products." (Somech, R., et al. 2004 *Cancer Treat. Rev.* 30:461-472; Miller, T. A., et al. 2003 *J. Med. Chem.* 46:5097-5116; Moradei, O., et al. 2005 *Curr. Med. Chem.*; Anti-Cancer Agents 5:529-560; Bolden, J. E., et al. 2006 *Nat. Rev. Drug Discovery* 5:769-784). In contrast to this assertion, the (S)-3-hydroxy-7-mercaptohept-4-enoic acid is, in fact, an essential motif in several cytotoxic natural products, including FK228 (FR901228) (Japanese Patent No. 03-141296, Jun. 17, 1991, Fujisawa Pharmaceutical Co., Ltd., Jpn. Kokai Tokkyo Koho JP, 1991; Ueda, H., et al. 1994; *J. Antibiot.* 47:301-310; Shigematsu, N., et al. 1994 *J. Antibiot.* 47:311-314; Ueda, H., et al. 1994 *J. Antibiot.* 47:315-323), FR901375 (Japanese Patent No. 03-141296, Jun. 17, 1991, Fujisawa Pharmaceutical Co., Ltd., Jpn. Kokai Tokkyo Koho JP; Ueda, H., et al. 1994; *J. Antibiot.* 47:301-310; Shigematsu, N., et al. 1994 *J. Antibiot.* 47:311-314; Ueda, H., et al. 1994 *J. Antibiot.* 47:315-323) and spiruchostatin (Masuoka, Y., et al. 2001 *Tetrahedron Lett.* 42:41-44) (structures depicted below), all of which are known histone deacetylase inhibitors (HDACi) (Townsend, P. A., et al. 2007 *The bicyclic depsipeptide family of histone deacetylase inhibitors, in Chemical Biology*; Schreiber, S. L., et al. Eds. Wiley-VCH Verlag GmbH & Co. 693-720).

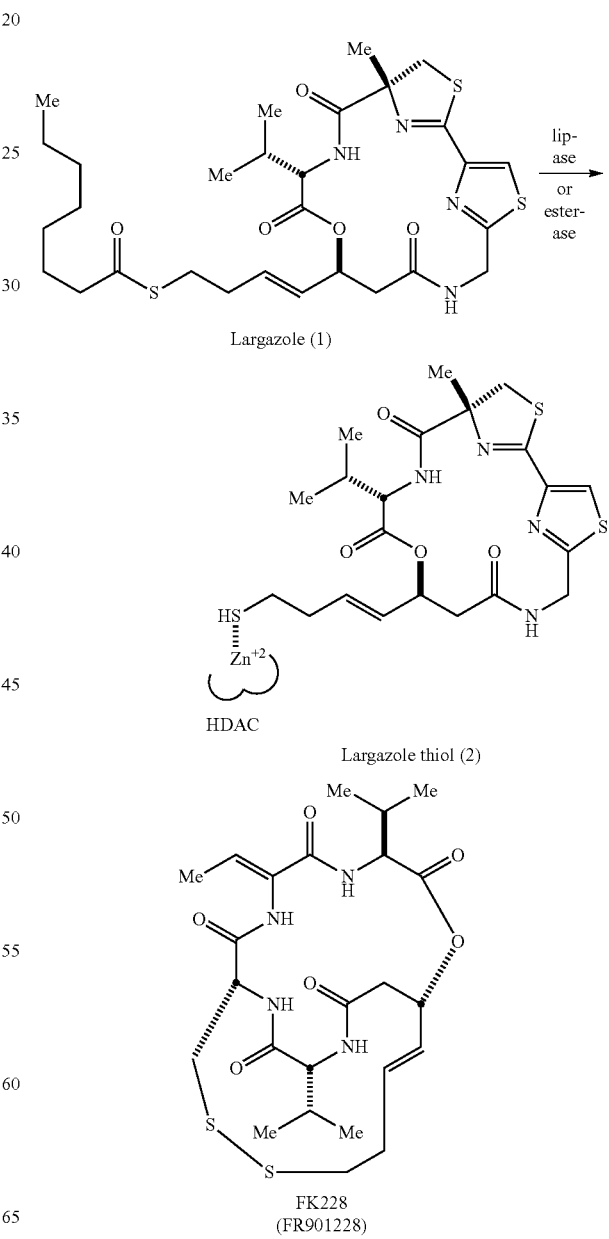

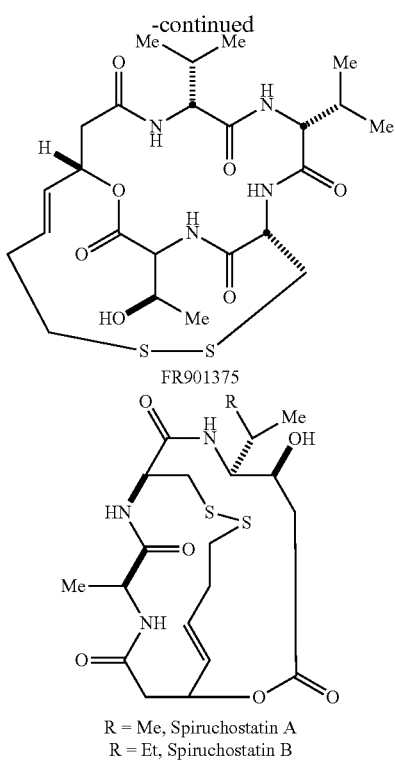

R = Me, Spiruchostatin A
R = Et, Spiruchostatin B

The histone deacetylase enzymes are zinc metalloenzymes that catalyze the hydrolysis of acetylated lysine residues in chromatin and, thereby, regulate transcription in eukaryotic cells (Somech, R., et al. 2004 *Cancer Treat. Rev.* 30:461; Miller, T. A., et al. 2003 S. *J. Med. Chem.* 46:5097-5116; Moradei, O., et al. 2005 *Curr. Med. Chem.; Anti-Cancer Agents* 5:529-560; Bolden, J. E., et al. 2006 *Nat. Rev. Drug Discovery* 5:769-784). Their selective inhibition has recently become a major area of research in cancer chemotherapy (Minucci, S., et al. 2006 *Nature Rev. Cancer* 6:38-51). To date, eighteen HDACs have been identified, which are generally divided into four classes based on sequence homology to yeast counterparts (Taunton, J., et al. 1996 *Science* 272: 408-411; Grozinger, C. M., et al. 1999 *Proc. Nat. Acad. Sci. USA* 96:4868-4873; Johnstone, R. W. 2002 *Nature Rev. Drug Disc.* 1:287-299). With respect to cancer therapy, there is an emerging consensus that Class I HDACs are clinically relevant, and that the undesirable toxicity associated with the first generation of HDAC inhibitors may be related to class indiscriminancy. As a result, programs have been initiated that are aimed at the synthesis and modification of peptide- and depsipeptide-based HDACi with the objective of optimizing structures for class- and even isoform-specific inhibition.

BRIEF SUMMARY OF THE INVENTION

The three natural substances FK228, FR901375, and spiruchostatin, are all activated in vitro and in vivo by reductive cleavage of a disulfide bond to expose the free sulfhydryl residue of the pendant (S)-3-hydroxy-7-mercaptohept-4-enoic acid moiety that coordinates to the active-site $Zn^{+2}$ residue of the HDACs resulting in a potent inhibitory effect (Yoshida, M., et al. 1990 *J. Biol. Chem.* 265:17174-17179; Yoshida, M., et al. 1990 *J. Antibiot.* 43:1101-1106). Given that largazole contains this well-known $Zn^{+2}$-binding arm, it would appear that largazole is simply a pro-drug that is activated by hydrolytic removal of the octanoyl residue by cellular lipases and/or esterases to produce the putative cytotoxic species 2 (the "largazole thiol"). It has previously been demonstrated that thioester analogues of FK228 retain their antiproliferative activity in cell-based assays (WO 2007/061939; Yurek-George, A., et al. 2007 *J. Med. Chem.* 50:5720-5726).

Reported herein are an efficient total synthesis of largazole, and the largazole thiol (2), as well as a demonstration that 2 is an extraordinarily potent HDACi. Further reported herein are additional largazole analogs, as well as uses of largazole, largazole thiol, and largazole analogs for the treatment of cancer and for the treatment of blood disorders.

In one aspect, the invention provides a compound of Formula (I)

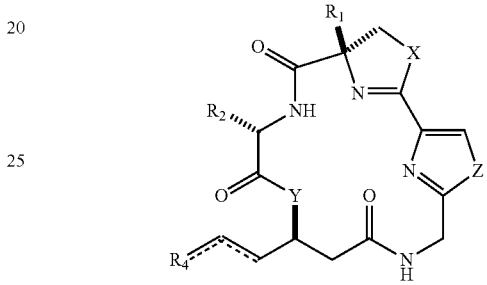

wherein X is S or O; Y is NR or O, wherein R is H, lower alkyl, or lower arylalkyl; Z is S or O; $R_1$ is H, lower alkyl, or lower arylalkyl; $R_2$ is lower alkyl, isopropyl, n-propyl, cyclopropyl, isobutyl, n-butyl, sec-butyl, or tert-butyl; $R_4$ is H, $(CH_2)_n COOH$, $(CH_2)_n CONHR$, $(CH_2)_n CONHOH$, $(CH_2)_n SR_3$, $SR_5$ (wherein $R_5$ is lower alkyl or lower aryl),

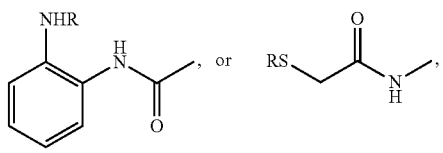

wherein n is at least 1, and wherein $R_3$ is H, octanoyl, acyl, SR, a higher acyl derivative, or

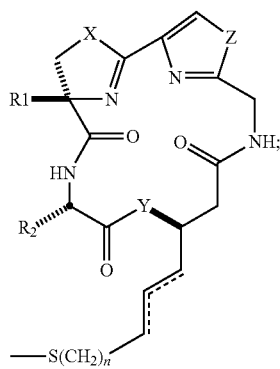

or a pharmaceutically acceptable salt, solvate, clathrate, prodrug, or stereoisomer thereof; wherein the compound is not largazole.

In another embodiment of a compound of the invention, X is S or O; Y is NH or O; Z is S or O; R$_1$ is H or methyl; R$_2$ is lower alkyl or isopropyl; R$_4$ is H, (CH$_2$)$_n$COOH, (CH$_2$)$_n$CONHR, (CH$_2$)$_n$CONHOH, (CH$_2$)$_n$SR$_3$,

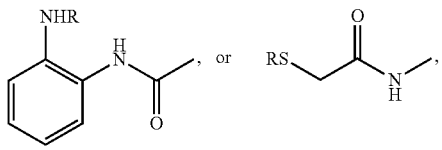

wherein n is at least 1, and wherein R$_3$ is H, octanoyl, acyl, SR, a higher acyl derivative, or

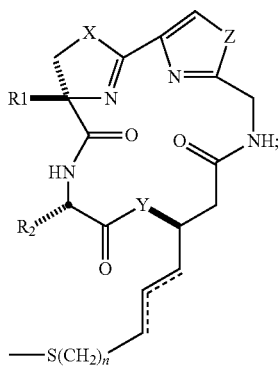

or a pharmaceutically acceptable salt, solvate, clathrate, prodrug, or stereoisomer thereof; wherein the compound is not largazole.

In another embodiment, the invention provides a compound of the formula (II):

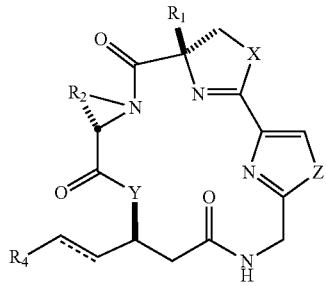

wherein the substituents are as defined above.

In another aspect, the invention provides a compound of Formula (III)

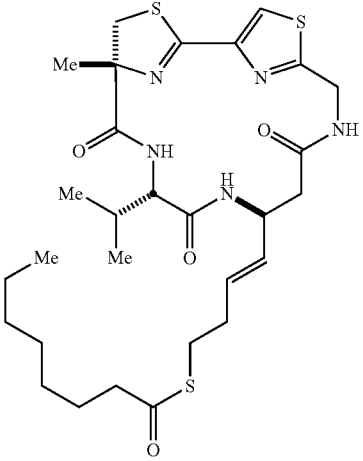

or a pharmaceutically acceptable salt, solvate, clathrate, prodrug, or stereoisomer thereof.

In yet another aspect, the invention provides a compound of Formula (IV)

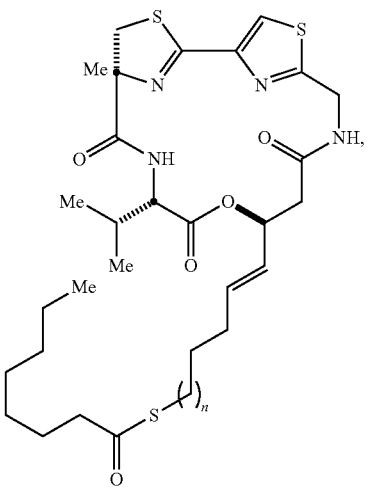

wherein n=1 or 2, or a pharmaceutically acceptable salt, solvate, clathrate, prodrug, or stereoisomer thereof.

In yet another aspect, the invention is directed to a compound of Formula (V)

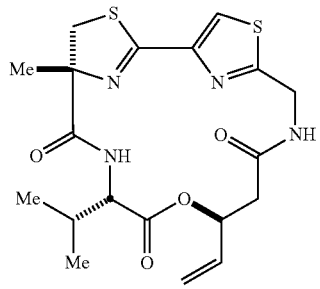

or a pharmaceutically acceptable salt, solvate, clathrate, prodrug, or stereoisomer thereof.

In yet another aspect, the invention is directed to a compound of Formula (VI)

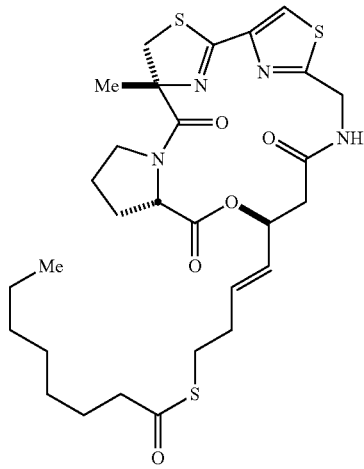

or a pharmaceutically acceptable salt, solvate, clathrate, prodrug, or stereoisomer thereof.

In yet another aspect, the invention is directed to a compound of Formula (VII)

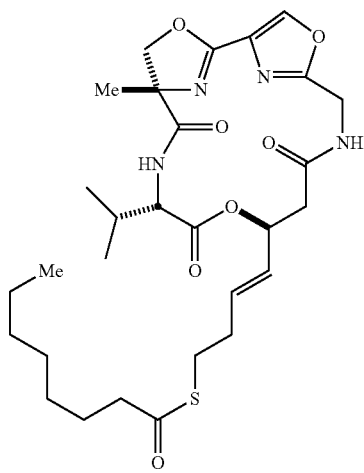

or a pharmaceutically acceptable salt, solvate, clathrate, prodrug, or stereoisomer thereof.

In yet another aspect, the invention provides a compound of Formula (VIII)

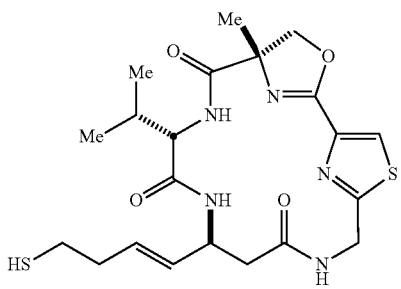

or a pharmaceutically acceptable salt, solvate, clathrate, prodrug, or stereoisomer thereof.

In yet another aspect, the invention provides a compound of Formula (IX)

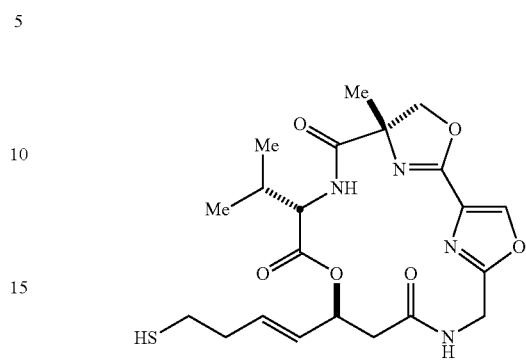

or a pharmaceutically acceptable salt, solvate, clathrate, prodrug, or stereoisomer thereof.

In yet another aspect, the invention provides a compound of Formula (X)

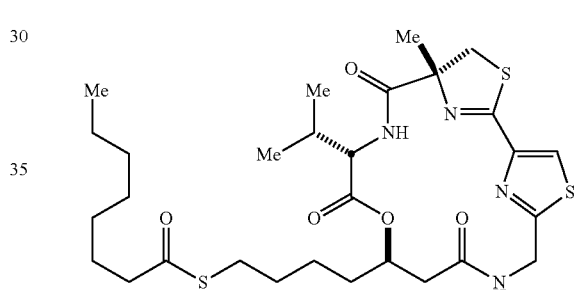

or a pharmaceutically acceptable salt, solvate, clathrate, prodrug, or stereoisomer thereof.

In yet another aspect, the invention provides a compound of Formula (X1)

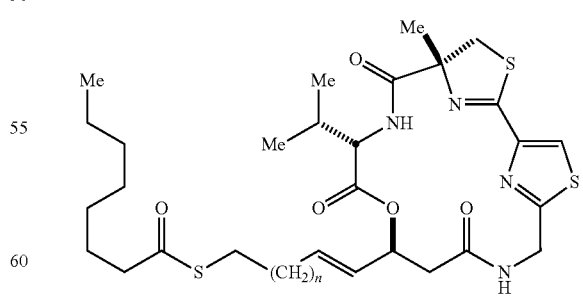

wherein n is at least 1;

or a pharmaceutically acceptable salt, solvate, clathrate, prodrug, or stereoisomer thereof.

In another aspect, the invention provides a compound of Formula (XII)

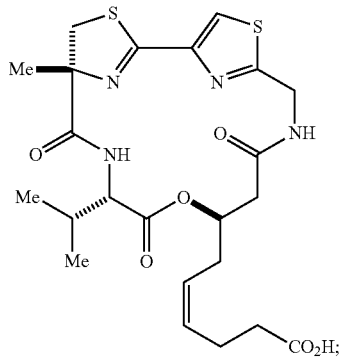

or a pharmaceutically acceptable salt, solvate, clathrate, prodrug, or stereoisomer thereof.

In yet another aspect, the invention provides a compound of Formula (XIII)

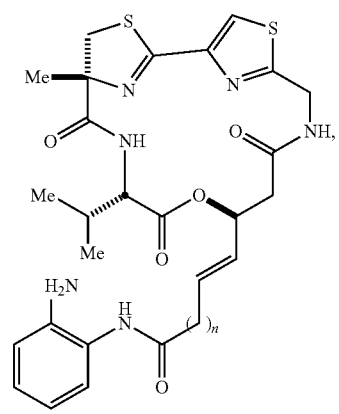

wherein n=2; or a pharmaceutically acceptable salt, solvate, clathrate, prodrug, or stereoisomer thereof.

In yet another aspect, the invention provides a compound of Formula (XIV)

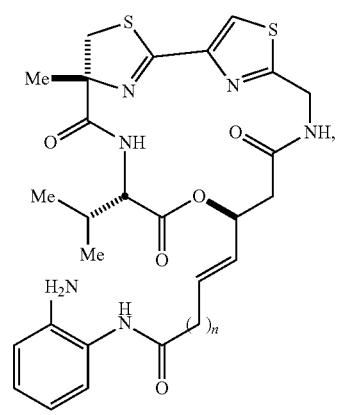

wherein n=3; or a pharmaceutically acceptable salt, solvate, clathrate, prodrug, or stereoisomer thereof.

In yet another aspect the invention provides a compound of Formula (XV)

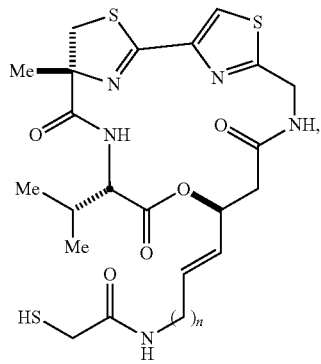

wherein n=1; or a pharmaceutically acceptable salt, solvate, clathrate, prodrug, or stereoisomer thereof.

In yet another aspect, the invention provides a compound of Formula (XVI)

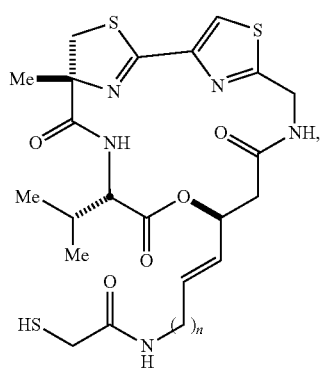

wherein n=2; or a pharmaceutically acceptable salt, solvate, clathrate, prodrug, or stereoisomer thereof.

In yet another aspect, the invention provides a compound of Formula (XVII)

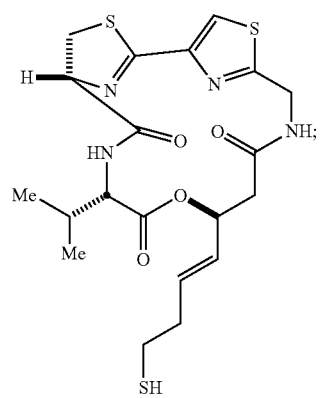

or a pharmaceutically acceptable salt, solvate, clathrate, prodrug, or stereoisomer thereof.

In yet another aspect, the invention provides a compound of Formula (XVIII)

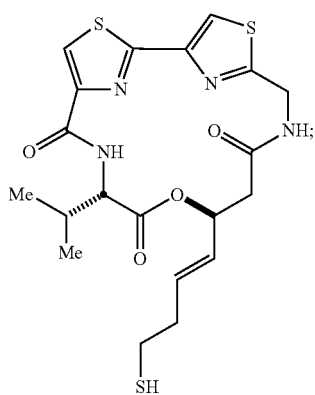

or a pharmaceutically acceptable salt, solvate, clathrate, prodrug, or stereoisomer thereof.

In one aspect, the invention provides a compound of Formula (XIX)

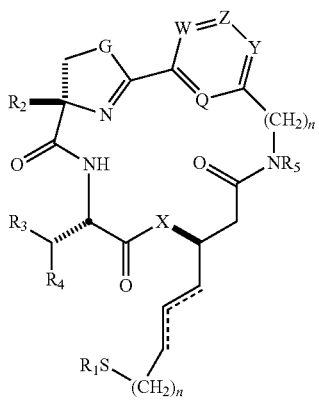

n = 0, 1, 2, 3, etc.

wherein X=O or $NR_6$, wherein $R_6$=H, lower alkyl, or lower arylalkyl; G=S, O, or $NR_9$, wherein $R_9$=H, lower alkyl, or lower arylalkyl; Q, Y, W, Z are, independently, N or CH, wherein at least one of Q, Y, W, and Z is CH; $R_1$=C(O)$(CH_2)_6CH_3$, $C(O)R_7$ (wherein $R_7$=lower alkyl, lower aryl, or lower arylalkyl), or

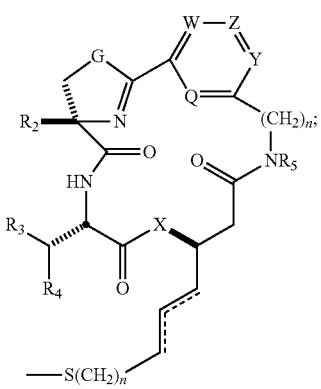

or a pharmaceutically acceptable salt, solvate, clathrate, prodrug, or stereoisomer thereof.

In another aspect, the invention provides a compound of Formula (XX)

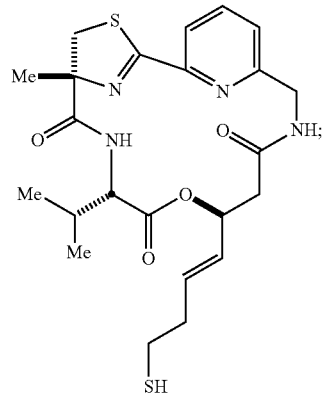

or a pharmaceutically acceptable salt, solvate, clathrate, prodrug, or stereoisomer thereof.

In another aspect, the invention provides a method for treating cancer in a subject, comprising administering to the subject a therapeutically effective amount of a compound as disclosed herein, wherein the compound is not largazole. In another aspect, a method of the invention further comprises treating said subject with an additional form of therapy for cancer.

In yet another aspect, the invention provides a method for treating a blood disorder in a subject, comprising administering to the subject a therapeutically effective amount of a compound of Formula (I)

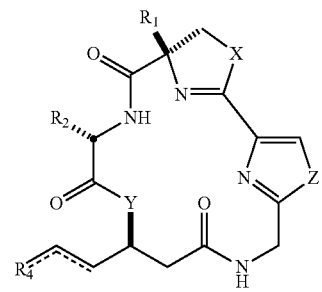

wherein X is S or O; Y is NR or O, wherein R is H, lower alkyl, or lower arylalkyl; Z is S or O; $R_1$ is H, lower alkyl, or lower arylalkyl; $R_2$ is lower alkyl, isopropyl, n-propyl, cyclopropyl, isobutyl, n-butyl, sec-butyl, or tert-butyl; $R_4$ is H, $(CH_2)_nCOOH$, $(CH_2)_nCONHR$, $(CH_2)_nCONHOH$, $(CH_2)_nSR_3$, $SR_5$ (wherein $R_5$ is lower alkyl or lower aryl),

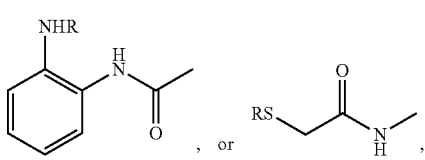

wherein n is at least 1, and wherein $R_3$ is H, octanoyl, acyl, SR, a higher acyl derivative, or

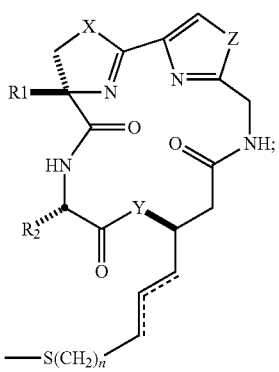

or a pharmaceutically acceptable salt, solvate, clathrate, prodrug, or stereoisomer thereof.

In yet another aspect, the invention provides a method for treating a blood disorder in a subject, comprising administering to the subject a therapeutically effective amount of a compound as disclosed herein. In an additional aspect of a method of the invention, the blood disorder is at least one of a hemoglobinopathy or a thalassemia. In a further aspect of the invention, the method further comprises treating the subject with an additional form of therapy for the blood disorder.

A method according to the invention may further comprise obtaining the compound. In a further aspect of a method according to the invention, the subject is human.

In one aspect, the invention provides a pharmaceutical composition comprising a therapeutically effective amount of a compound as disclosed herein and at least one pharmaceutically acceptable excipient for treating cancer in a subject, wherein the compound is not largazole.

In another aspect, the invention provides a pharmaceutical composition comprising a therapeutically effective amount of a compound of Formula (I)

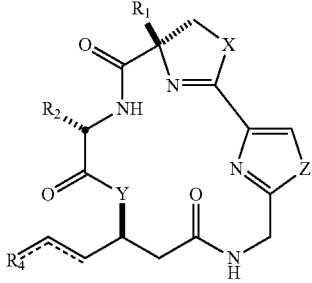

wherein X is S or O; Y is NR or O, wherein R is H, lower alkyl, or lower arylalkyl; Z is S or O; $R_1$ is H, lower alkyl, or lower arylalkyl; $R_2$ is lower alkyl, isopropyl, n-propyl, cyclopropyl, isobutyl, n-butyl, sec-butyl, or tert-butyl; $R_4$ is H, $(CH_2)_n COOH$, $(CH_2)_n CONHR$, $(CH_2)_n CONHOH$, $(CH_2)_n SR_3$, $SR_5$ (wherein $R_5$ is lower alkyl or lower aryl),

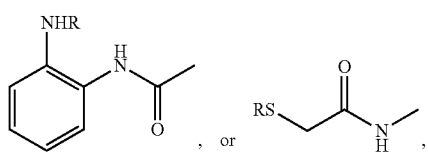

wherein n is at least 1, and wherein $R_3$ is H, octanoyl, acyl, SR, a higher acyl derivative, or

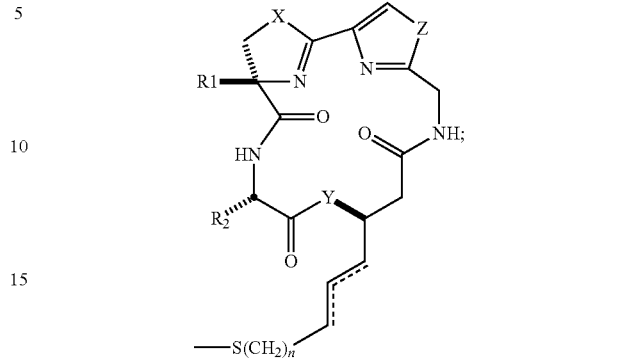

or a pharmaceutically acceptable salt, solvate, clathrate, prodrug, or stereoisomer thereof; and at least one pharmaceutically acceptable excipient for treating a blood disorder in a subject.

In yet another aspect, the invention provides a pharmaceutical composition comprising a therapeutically effective amount of a compound as disclosed herein and at least one pharmaceutically acceptable excipient for treating a blood disorder in a subject. In a further aspect of a composition of the invention, the blood disorder is a hemoglobinopathy or a thalassemia. In still a further aspect of a composition of the invention, the subject is human.

In another aspect, the invention provides a composition containing a radiolabelled compound of Formula (I)

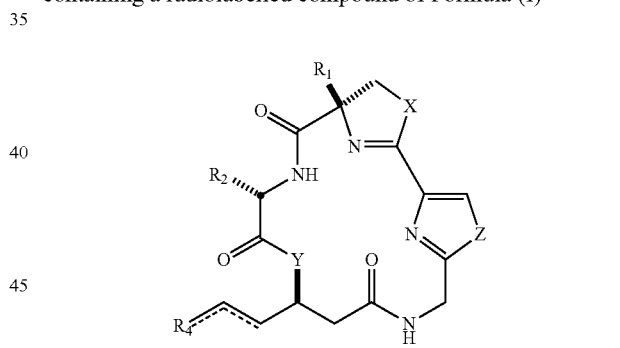

wherein X is S or O; Y is NR or O,
wherein R is H, lower alkyl, or lower arylalkyl; Z is S or O; $R_1$ is H, lower alkyl, or lower arylalkyl; $R_2$ is lower alkyl, isopropyl, n-propyl, cyclopropyl, isobutyl, n-butyl, sec-butyl, or tert-butyl; $R_4$ is H, $(CH_2)_n COOH$, $(CH_2)_n CONHR$, $(CH_2)_n CONHOH$, $(CH_2)_n SR_3$, $SR_5$ (wherein $R_5$ is lower alkyl or lower aryl),

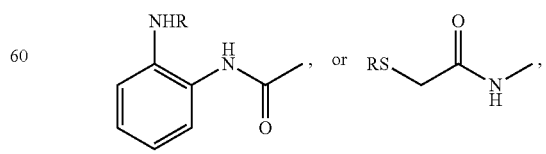

wherein n is at least 1, and wherein $R_3$ is H, octanoyl, acyl, SR, a higher acyl derivative, or

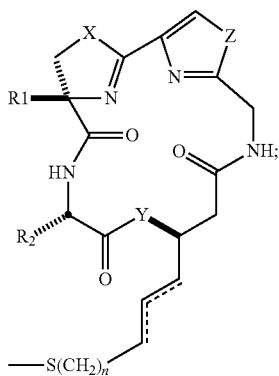

or a pharmaceutically acceptable salt, solvate, clathrate, prodrug, or stereoisomer thereof; wherein the compound is not largazole.

Other aspects of the invention are described in or are obvious from the following disclosure and are within the ambit of the invention.

BRIEF DESCRIPTION OF THE FIGURES

The following Detailed Description of the Invention, given by way of Examples, but not intended to limit the invention to specific embodiments described, may be understood in conjunction with the accompanying figures, in which:

FIG. 5, below, provides the data gathered in numerical form.

DETAILED DESCRIPTION OF THE INVENTION

I. Definitions

Figure 1A:
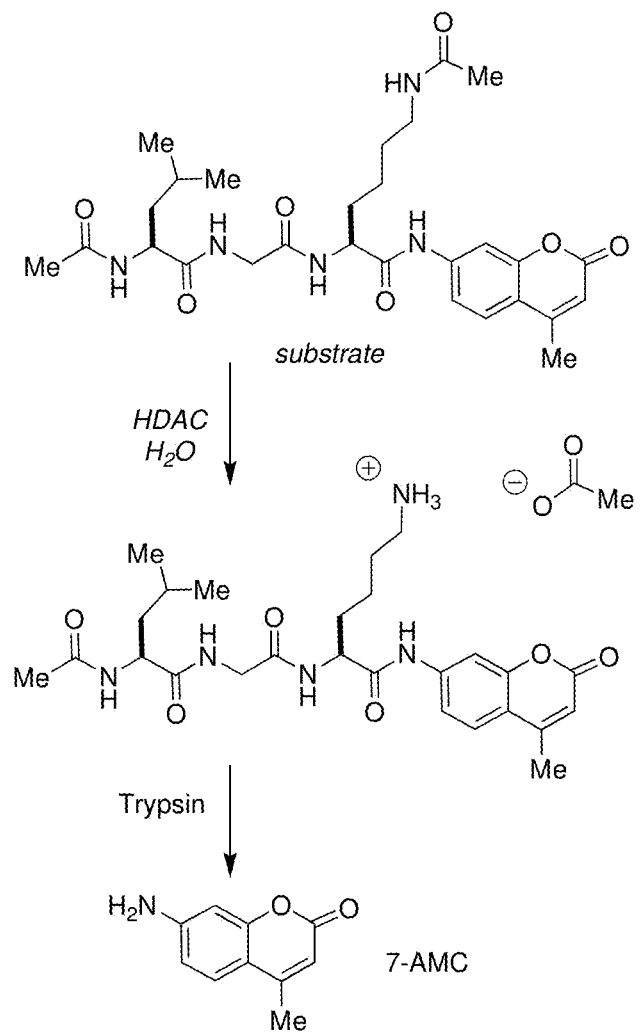
FIG. 1A schematically depicts the kinetic biochemical assay of HDAC function. The fluorophore 7-amino-4-methylcoumarin (7AMC) is linked by an amide bond to acetylated lysine in the context of a deacetylase substrate. Pictured is a derived substrate compatible with assays for HDAC1, HDAC2, HDAC3 and HDAC6. The deacetylase hydrolyzes the acetylated lysine, which is then a substrate for rapid trypsin digest releasing TAMC (lower structure) detected in real time by a fluorescence plate-reader.

As used herein, the term "compound(s) of the invention" and similar terms refer to a compound of formula (I) or a pharmaceutically acceptable salt, solvate, clathrate, or prodrug thereof.

In the compound of Formula (I), the designation of one line parallel to a dotted line represents an optional double bond. When present, the double bond may be either is cis- or trans-configuration.

As used herein, "lower alkyl" or "lower alkyl moieties" contain from 1-12 carbon atoms, "lower aryl" or "lower aryl moieties" contain from 6-12 carbon atoms, and "lower arylalkyl" or "lower arylalkyl moieties" contain from 7-12 carbon atoms. In a preferred embodiment, lower alkyl refers to a $C_{1-7}$alkyl, lower aryl to a $C_{6-10}$aryl, and lower arylalkyl to a $C_{7-11}$aralkyl. Included are substituted derivatives of lower chain alkyl, aryl and arylalkyl moieties, wherein the substituent is selected from (but are not limited to) one or more of the following chemical moieties: —OH, —$OR_7$, —COON, —$COOR_7$, —$CONH_2$, —$NH_2$, —$NHR_7$, —$NR_7R_7$, —SH, —$SR_7$, —$SO_2R_7$, —$SO_2H$, —$SOR_7$, —$PO_3R_7$, —$OPO_3R_7$, and halogen (including F, Cl, Br and I), wherein each occurrence of $R_7$ is independently selected from a lower chain alkyl, aryl or arylalkyl moiety. Moreover, cyclic lower chain alkyl, aryl and arylalkyl moieties of the invention include naphthalene, as well as heterocyclic compounds such as thiophene, pyrrole, furan, imidazole, oxazole, thiazole, pyrazole, 3-pyrroline, pyrrolidine, pyridine, pyrimidine, purine, quinoline, isoquinoline and carbazole.

As used herein, the term "prodrug" refers to a derivative of a compound that can hydrolyze, oxidize, or otherwise react under biological conditions (in vitro or in vivo) to provide a compound of the invention. Prodrugs may only become active upon some reaction under biological conditions, but they may have activity in their unreacted forms. Examples of prodrugs contemplated herein include, without limitation, analogs or derivatives of compounds of the invention. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs and their uses are well known in the art (see, e.g., Berge, et al. 1977 *J. Pharm. Sci.* 66:1-19). Prodrugs can typically be prepared using well-known methods, such as those described in Burger's Medicinal Chemistry and Drug Discovery (1995, Manfred E. Wolff ed., 5th ed. 172-178, 931-932).

It will be noted that the structure of some of the compounds of this invention includes asymmetric carbon atoms, and thus may exist as racemic mixtures or as isolated isomeric forms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

Furthermore, some of the crystalline forms of the compounds of Formula (I) may exist as polymorphs, which are included in the present invention. In addition, some of the compounds of Formula (I) may also form solvates with water or other organic solvents. Such solvates are similarly included within the scope of this invention.

The term "treating", as used herein, refers to altering the disease course of the subject being treated. Therapeutic effects of treatment include, without limitation, preventing occurrence or recurrence of disease, alleviation of symptom(s), diminishment of direct or indirect pathological consequences of the disease, decreasing the rate of disease progression, amelioration or palliation of the disease state, and remission or improved prognosis.

Cancer is a term used for diseases in which abnormal cells divide without control and are able to invade other tissues. There are more than 100 different types of cancer. Most cancers are named for the organ or type of cell in which they start—for example, cancer that begins in the colon is called colon cancer; cancer that begins in basal cells of the skin is called basal cell carcinoma. The main categories of cancer include carcinomas, sarcomas, leukemias, lymphomas and myelomas, and central nervous system cancers. Some common cancer types include, but are not limited to, bladder cancer, breast cancer, colon and rectal cancer, endometrial cancer, kidney (renal cell) cancer, leukemia, lung cancer, melanoma, non-Hodgkin's lymphoma, pancreatic cancer, prostate cancer, skin cancer (non-melanoma), and thyroid cancer. In a preferred embodiment, the cancers contemplated for treatment herein include cutaneous T-cell lymphoma, non-Hodgkin's and Hodgkin's lymphoma, pancreatic cancer, and ovarian cancer.

Hemoglobinopathies and thalassemias can both be characterized as "blood disorders". Blood disorders includes disorders that can be treated, prevented, or otherwise ameliorated by the administration of a compound of the invention. A blood disorder is any disorder of the blood and blood-forming organs. The term blood disorder includes nutritional anemias (e.g., iron deficiency anemia, sideropenic dysphasia, Plummer-Vinson syndrome, vitamin B 12 deficiency anemia, vitamin B 12 deficiency anemia due to intrinsic factor, pernicious anemia, folate deficiency anemia, and other nutritional anemias), myelodysplastic syndrome, bone marrow failure or anemia resulting from chemotherapy, radiation or other agents or therapies, hemolytic anemias (e.g., anemia due to enzyme disorders, anemia due to phosphate dehydrogenase (G6PD) deficiency, favism, anemia due to disorders of glutathione metabolism, anemia due to disorders of glycolytic enzymes, anemias due to disorders of nucleotide metabolism and anemias due to unspecified enzyme disorder), thalassemia, α-thalassemia, β-thalassemia, δβ-thalassemia, thalassemia trait, hereditary persistence of fetal hemoglobin (HPFP), and other thalassemias, sickle cell disorders (sickle cell anemia with crisis, sickle cell anemia without crisis, double heterozygous sickling disorders, sickle cell trait and other sickle cell disorders), hereditary hemolytic anemias (hereditary spherocytosis, hereditary elliptocytosis, other hemoglobinopathies and other specified hereditary hemolytic anemias, such as stomatocyclosis), acquired hemolytic anemia (e.g., drug-induced autoimmune hemolytic anemia, other autoimmune hemolytic anemias, such as warm autoimmune hemolytic anemia, drug-induced non-autoimmune hemolytic anemia, hemolytic-uremic syndrome, and other non-autoimmune hemolytic anemias, such as microangiopathic hemolytic anemia); aplastic anemias (e.g., acquired pure red cell aplasia (erythroblastopenia), other aplastic anemias, such as constitutional aplastic anemia and Fanconi anemia, acute posthemorrhagic anemic, and anemias in chronic diseases), coagulation defects (e.g., disseminated intravascular coagulation (difibrination syndrome)), hereditary factor VIII deficiency (hemophilia A), hereditary factor IX deficiency (Christmas disease), and other coagulation defects such as Von Willebrand's disease, hereditary factor Xi deficiency (hemophilia C), purpura (e.g., qualitative platelet defects and Glanzmann's disease), neutropenia, agranulocytosis, functional disorders of polymorphonuclear neutrophils, other disorders of white blood cells (e.g., eosinophilia, leukocytosis, lymphocytosis, lymphopenia, monocytosis, and plasmacyclosis), diseases of the spleen, methemoglobinemia, other diseases of blood and blood forming organs (e.g., familial erythrocytosis, secondary polycythemia, essential thrombocytosis and basophilia), thrombocytopenia, infectious anemia, hypoproliferative or hypoplastic anemias, hemoglobin C, D and E disease, hemoglobin lepore disease, and HbH and HbS diseases, anemias due to blood loss, radiation therapy or chemotherapy, or thrombocytopenias and neutropenias due to radiation therapy or chemotherapy, sideroblastic anemias, myelophthisic anemias, antibody-mediated anemias, and certain diseases involving lymphoreticular tissue and reticulohistiocytic system (e.g., Langerhans' cell hystiocytosis, eosinophilic granuloma, Hand-Schuller-Christian disease, hemophagocytic lymphohistiocytosis, and infection-associated hemophagocytic syndrome).

The term "pharmaceutically acceptable excipient", as used herein, refers to carriers and vehicles that are compatible with the active ingredient (for example, a compound of the invention) of a pharmaceutical composition of the invention (and preferably capable of stabilizing it) and not deleterious to the subject to be treated. For example, solubilizing agents that form specific, more soluble complexes with the compounds of the invention can be utilized as pharmaceutical excipients for delivery of the compounds. Suitable carriers and vehicles are known to those of extraordinary skill in the art. The term "excipient" as used herein will encompass all such carriers, adjuvants, diluents, solvents, or other inactive additives. Suitable pharmaceutically acceptable excipients include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical compositions of the invention can also be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like, which do not deleteriously react with the active compounds of the invention.

The compounds of the invention that are basic in nature are capable of forming a wide variety of salts with various inorganic and organic acids. The acids that may be used to prepare pharmaceutically acceptable acid addition salts of the compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other compounds of the invention not specifically described in the foregoing experimental section can be accomplished using combinations of the reactions described above that will be apparent to those skilled in the art.

Thus, as used herein, the term "pharmaceutically acceptable salt," is a salt formed from an acid and a basic group of a compound of the invention. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate salts.

The term "pharmaceutically acceptable salt" also refers to a salt prepared from a compound of the invention having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. Other pharmaceutically acceptable salts are described in the Handbook of Pharmaceutical Salts. Properties, Selection, and Use (P. Heinrich Stahl and C. Wermuth, Eds., Verlag Helvetica Chica Acta, Zurich, Switzerland (2002)).

The term "subject" as used herein refers to a vertebrate, preferably a mammal, more preferably a primate, still more preferably a human. Mammals include, without limitation, humans, primates, wild animals, feral animals, farm animals, sports animals, and pets.

The term "therapeutically effective amount" as used herein refers to an amount sufficient to effect a beneficial or desired clinical result upon treatment. Specifically, the term "therapeutically effective amount" means an amount of a compound of this invention sufficient to measurably (i) reduce or inhibit the growth of transformed (cancer) cells in a relevant in vitro assay or cause a measurable improvement in an animal model of cancer and/or (ii) induce expression of fetal hemoglobin in a relevant in vitro assay or cause a measurable improvement in an animal model of a hemoglobinopathy and/or thalassemia, for example, a sickle cell disease. Alternatively, a "therapeutically effective amount" is an amount of a compound of this invention sufficient to confer a therapeutic or prophylactic effect on the treated subject against (i) cancer and/or (ii) a hemoglobinopathy and/or thalassemia. Therapeutically effective amounts will vary, as recognized by those skilled in the art, depending on the specific disease treated, the route of administration, the excipient selected, and the possibility of combination therapy.

Physiological effects that can be measured to determine the therapeutically effective amount include, without limitation, substrate protein hyperacetylation (histone, tubulin, hsp90, p53, STAT, etc.), gene induction (fetal hemoglobin, spinal muscle atrophy gene), impaired protein trafficking, improved neuronal vesicle trafficking, induction of apoptosis, cell cycle arrest, and induction of p21.

Relevant assays to measure such effects include, without limitation, Western (immuno)blot, RT-PCR, expression profile by microarray or other technology, high-content immunofluorescence, cytoblot, biochemical inhibition of HDAC proteins, alterations in chromatin structure by ChIP, and alterations in histone and/or other target protein modification by mass spectrometry.

The term "obtaining" as in "obtaining the compound" is intended to include purchasing, synthesizing or otherwise acquiring the compound (or indicated substance or material).

The terms "comprises", "comprising", are intended to have the broad meaning ascribed to them in U.S. Patent Law and can mean "includes", "including" and the like.

The invention can be understood more fully by reference to the following detailed description and illustrative examples, which are intended to exemplify non-limiting embodiments of the invention.

II. Embodiments of the Invention

Compounds of the Invention

The compounds of the invention are defined herein by their chemical structures and/or chemical names. The compounds of the invention are generally named according to the IUPAC or CAS nomenclature system. Abbreviations that are well known to one of ordinary skill in the art may be used. When a compound is referred to by both a chemical structure and a chemical name, and the chemical structure and chemical name conflict, the chemical structure is determinative of the compound's identity.

A dotted line parallel to a solid line in a chemical structure indicates the optional presence of a double bond. Two dotted lines parallel to solid lines adjacent to one another indicates the optional presence of a double bond in either, but not both, of the two positions. Either a E (trans) or Z (cis) geometry is indicated. In fact, all alkenes contemplated herein can exist as either E (trans) or Z (cis) geometry.

When administered to a subject, the compounds of the invention are administered in isolated form or as the isolated form in a pharmaceutical composition. As used herein, "isolated" means that the compounds of the invention are separated from other components of either (a) a natural source, such as a plant or cell, preferably bacterial culture, or (b) a synthetic organic chemical reaction mixture. Preferably, via conventional techniques, the compounds of the invention are purified. As used herein, "purified" means that when isolated, the isolate contains at least about 80%, preferably at least about 90%, more preferably at least about 95% and even more preferably at least about 98%, of a single compound of the invention by weight of the isolate.

Radioactive compounds have a long history of use in the discovery of new drugs. The compounds of the invention all have the potential to be easily radiolabeled and can be used to discover other new agents that (i) reduce or inhibit the growth of transformed (cancer) cells and/or (ii) induce fetal hemoglobin expression. For example, radioactive compounds of the invention can be utilized to validate, optimize, and standardize bioassays used for discovery of other compounds that (i) reduce or inhibit the growth of transformed (cancer) cells and/or (ii) induce fetal hemoglobin expression. Likewise, radioactive compounds of the invention can be utilized as a benchmark to discover compounds that show improved activity in bioassays that (i) reduce or inhibit the growth of transformed (cancer) cells and/or (ii) induce fetal hemoglobin expression.

In one embodiment, the invention is directed to the largazole analogs:

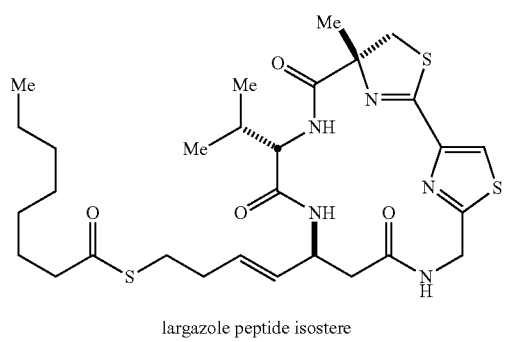

largazole peptide isostere

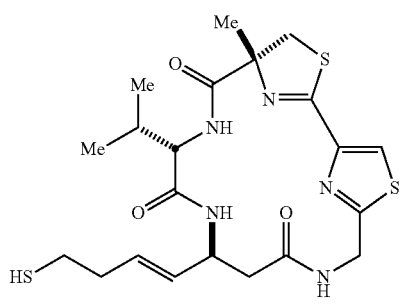

largazole thiol peptide isostere

In another embodiment, the invention is directed to the largazole analogs:

(1)

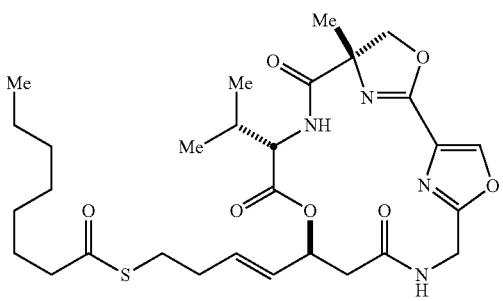

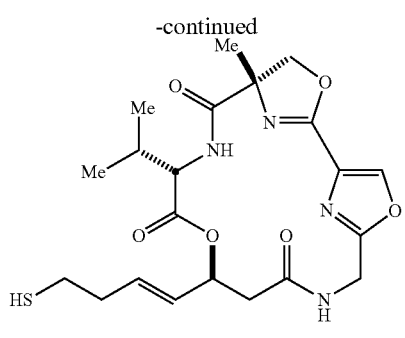

oxazole-oxazoline analog (2)

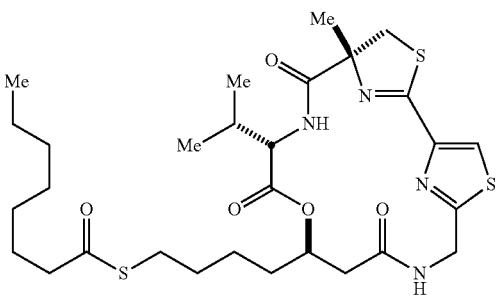

Saturated largazole

Longer side-chain analogs:

(3)

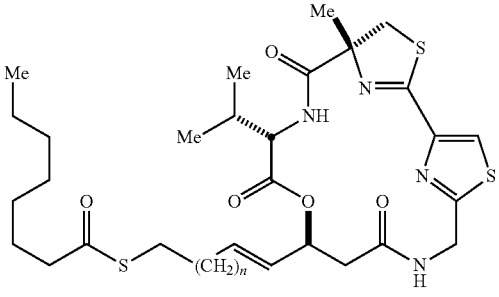

longer chain analogs,
where n = 1 = largazole
n = 2
n = 3

Valine to proline replacement:

(4)

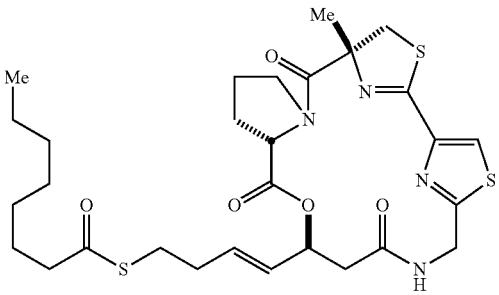

Preparation of Compounds of the Invention

The compounds of the invention can be prepared in an efficient, cost-effective manner.

Disconnection of the macrocycle to the four key subunits, that is, α-methyl cysteine (3), thiazole (4), (S)-valine (5), and (S)-3-hydroxy-7-mercaptohept-4-enoic acid (6), is illustrated below.

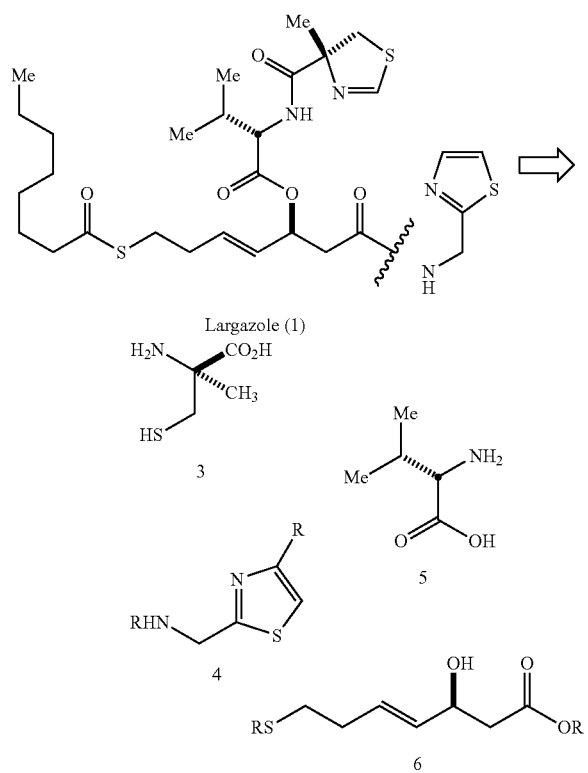

Largazole (1)

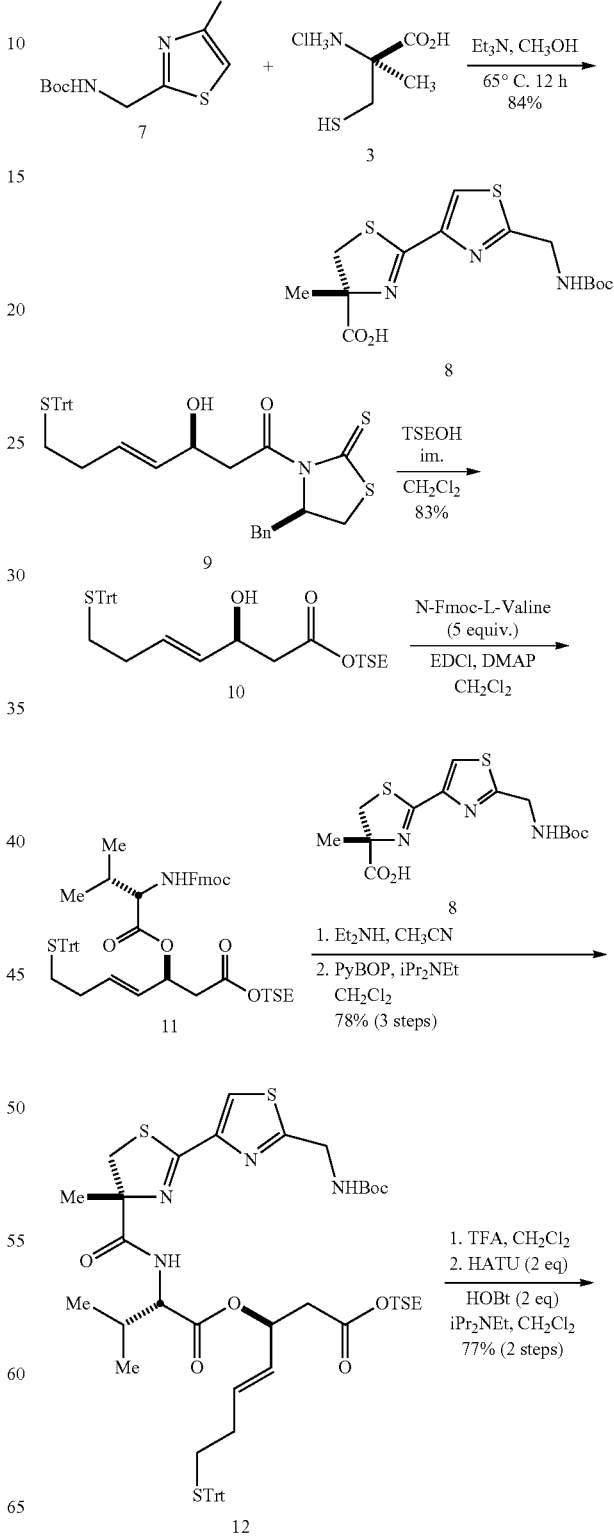

Given the ready availability of these building blocks from prior efforts (Jeanguenat, A. and Seebach 1991 *J. Chem. Soc., Perkin Trans.* 1:2291-2298; Mulqueen, G. C., et al. 1993 *Tetrahedron* 49:5359-5364; Li, K. W., et al. 1996 *J Am Chem Soc* 118:7237-7238; Chen, Y., et al. 2003 *J Org Chem* 68:8902-8905; Yurek-George, A., et al. 2004 *J Am Chem Soc* 126:1030-1031), the underlying synthetic challenge turned out to be the macrocyclization strategy. Due to the anticipated susceptibility of the β-carboxylate linkage to undergo elimination, initial efforts were focused on installing this linkage last. However, all methods, both direct (macrolactonization via Yamaguchi, Mukaiyama, Keck, and Shiina procedures) and indirect (inversion via Mitsunobu reaction) failed to provide the desired macrocycle. An additional attempt at closure of the depsipeptide ring via a late-stage thiazoline-forming reaction also failed to provide the desired macrocyclic product.

Thus, a strategy involving early installation of the ester and subsequent closure about the least-hindered amide bond was employed. The necessary α-methyl cysteine subunit with the requisite (R)-stereochemistry was obtained via the Pattenden modification of the Seebach protocol on L-cysteine methyl ester (Scheme 1, below) (Jeanguenat, A. and Seebach 1991 *J. Chem. Soc., Perkin Trans.* 1:2291-2298; Mulqueen, G. C., et al. 1993 *Tetrahedron* 49:5359-5364). Alternatively, α-methyl serine was obtained and converted into α-methyl cysteine by a published procedure (Smith, N. D. and Goodman, M. 2003 *Org. Lett.* 5:1035-1037). Gram quantities of this amino acid were obtained in high enantiomeric purity and condensed with the known nitrile (7) (Videnov, G., et a/0.1996 *Angew. Chem. Int. Ed. Eng.* 35:1503-1506; Lange, U. E. W., et a/0.1999 *Tetrahedron Lett.* 40:7067-7070) to provide the thiazoline-thiazole subunit (8) in high yield.

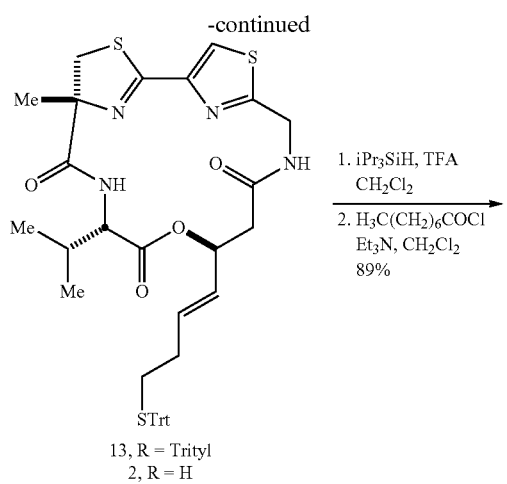

13, R = Trityl
2, R = H 1. iPr₃SiH, TFA CH₂Cl₂
2. H₃C(CH₂)₆COCl Et₃N, CH₂Cl₂
89%

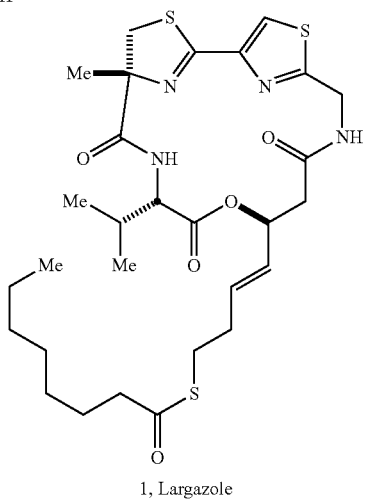

1, Largazole

A novel synthetic route to the β-hydroxy acid (10) has recently been found based on a Noyori asymmetric transfer hydrogenation (Greshock, D. M., et al. 2008 *Org Lett* 10:613-616). A recently elucidated synthesis of this subunit has also been found to be expedient and high yielding (Yurek-George, A., et al. 2004 *J. Am. Chem. Soc.* 126:1030-1031). Thiazolidinethione (9) was treated with 2-trimethylsilylethanol to provide the TSE-protected acid (10), which was subsequently coupled to N-Fmoc-L-valine to afford 11. Due to the sluggish reactivity of allylic alcohol 10, it was found necessary to use an excess (5 equivalents) of the commercially available amino acid. Removal of the Fmoc group and PyBOP-mediated coupling to the thiazoline-thiazole carboxylic acid (8) furnished the acyclic precursor (12).

Cyclization was effected under high dilution in the presence of two equivalents each of HOBt and HATU, furnishing the desired macrocycle 13 in 77% isolated yield from 12. Removal of the S-trityl protecting group was accomplished with iPr₃SiH and TFA to provide an authentic sample of the largazole thiol (2) in excellent yield.

Acylation of 2 with octanoyl chloride under standard conditions afforded synthetic largazole in 89% yield from 13. The spectroscopic data ($^1$H NMR, $^{13}$C NMR and HRMS) for the synthetic substance were in excellent agreement with that published for the natural product.[1]

As regards the synthesis of largazole analogs, several schemes are described as follows:

1. Synthesis of the Largazole Peptide Isostere:

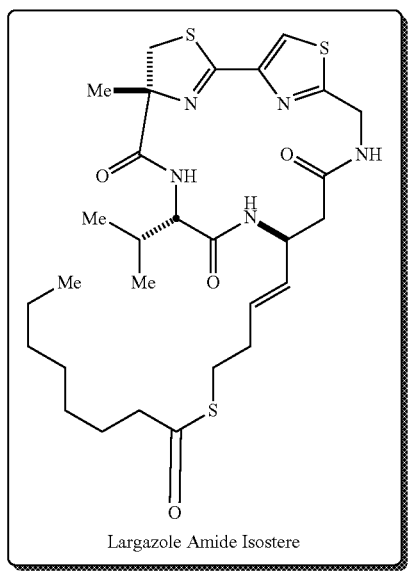

Largazole Amide Isostere

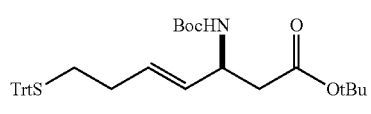
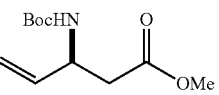
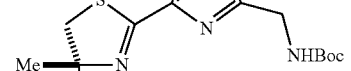
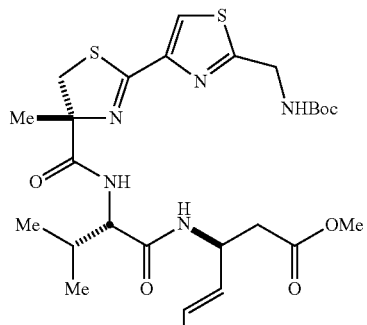
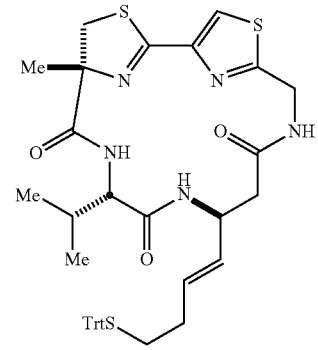
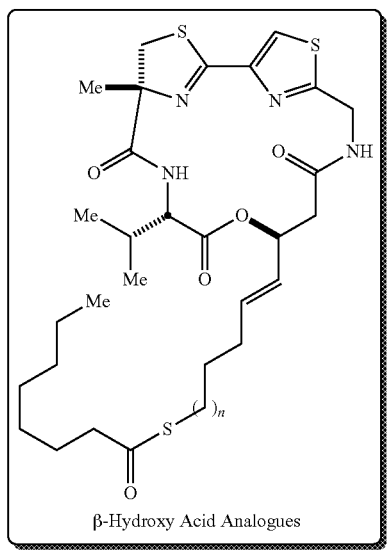
2. Synthesis of Zinc-Binding Domain (Side-Chain) Analogs:
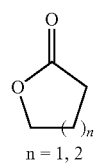
-continued
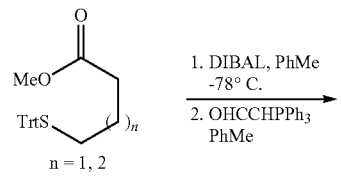
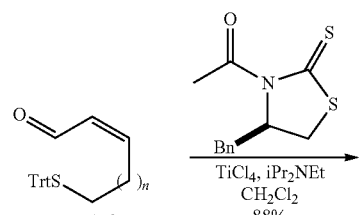
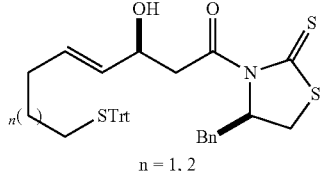
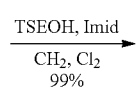
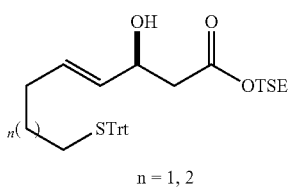

29
-continued
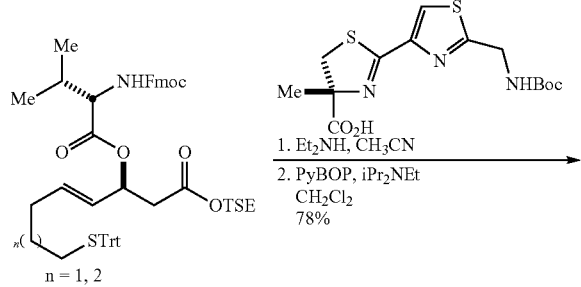
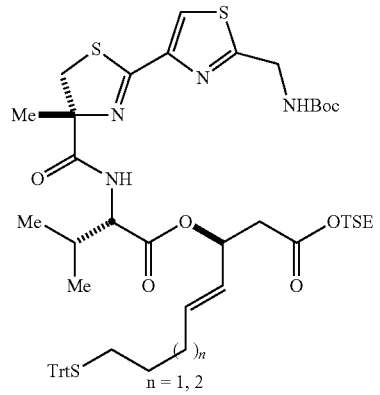
3. Synthesis of the Largazole Template Metathesis Substrate:
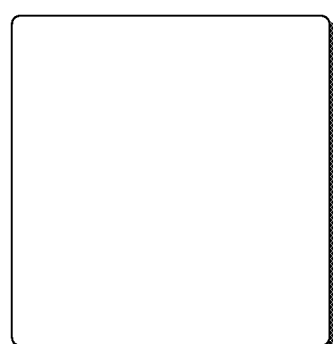
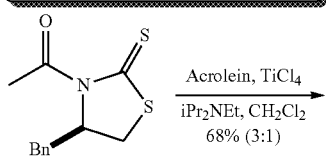
30
-continued
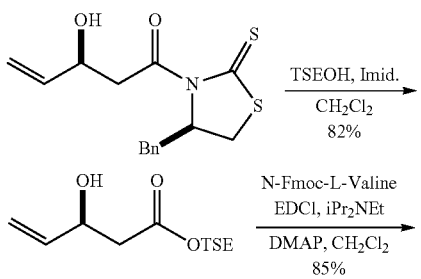
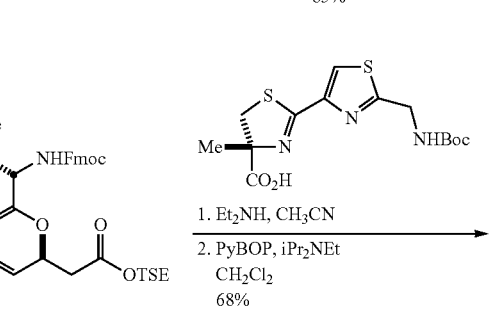
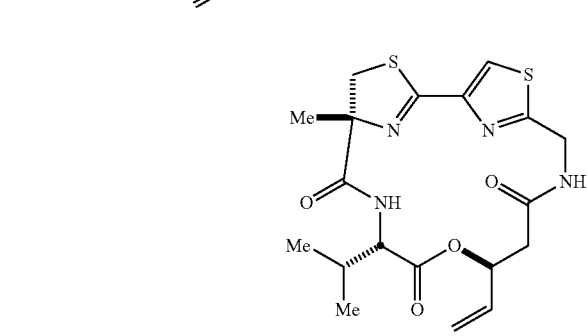
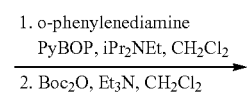
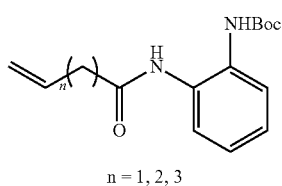

31
-continued
32
-continued
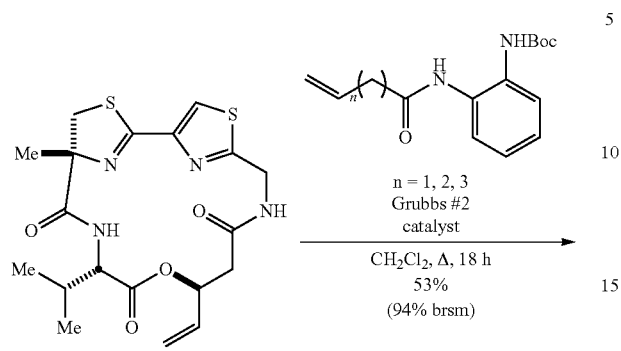
n = 1, 2, 3
Grubbs #2 catalyst
CH₂Cl₂, Δ, 18 h
53%
(94% brsm)
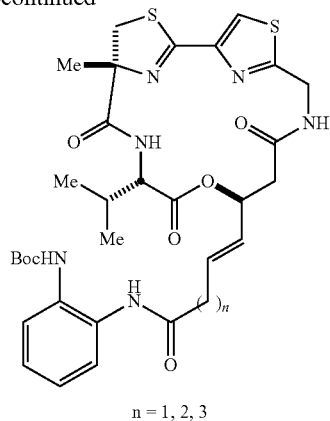
n = 1, 2, 3
4. Synthesis of the Largazole Proline Analogue:
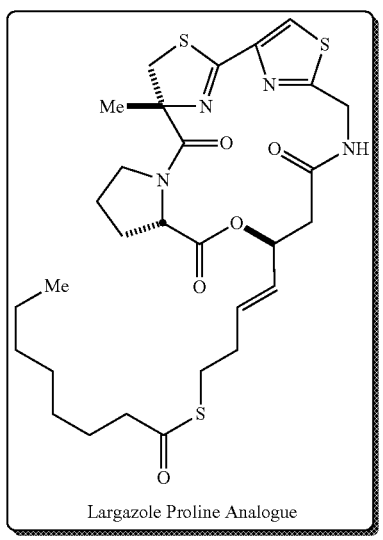
Largazole Proline Analogue
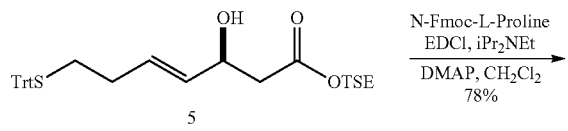
N-Fmoc-L-Proline
EDCl, iPr₂NEt
DMAP, CH₂Cl₂
78%
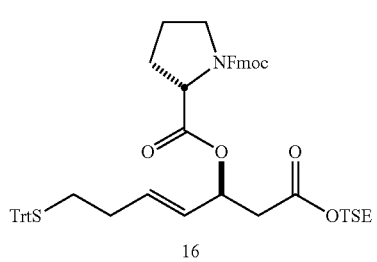
1. Et₂NH, CH₃CN
2. PyBOP, iPr₂NEt
   CH₂Cl₂
   68%

33
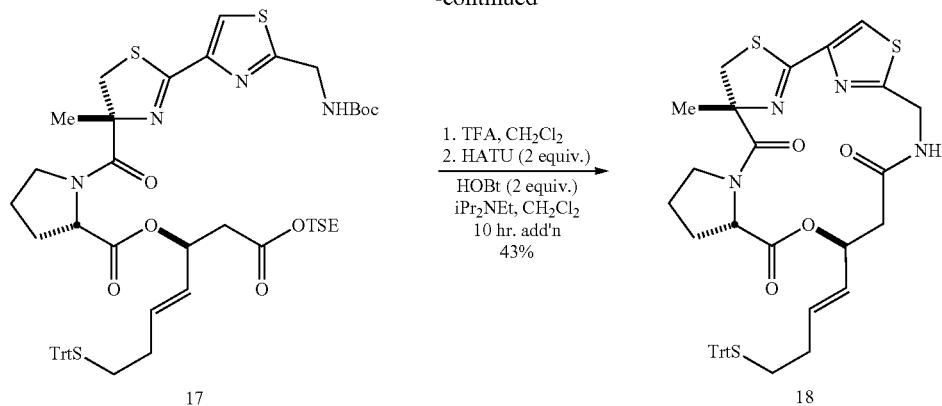
5. Synthesis of Largazole Oxazoline-Oxazole Analogue:
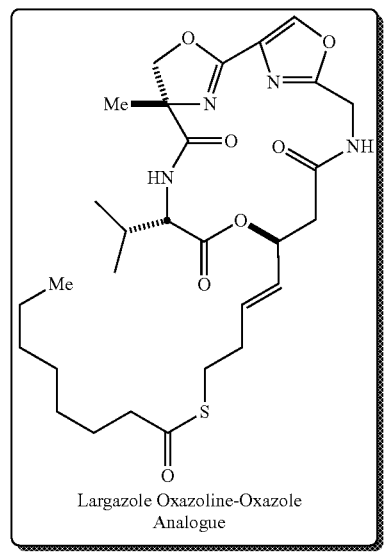
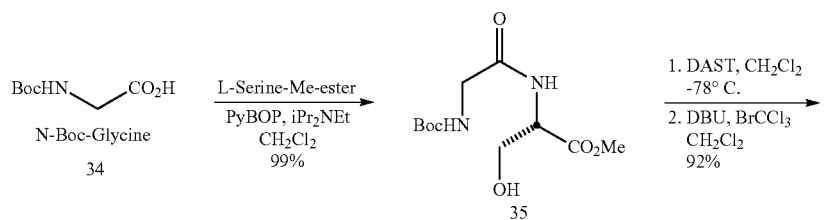
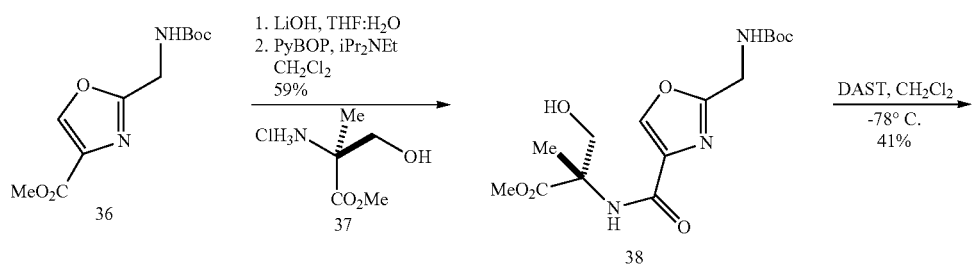

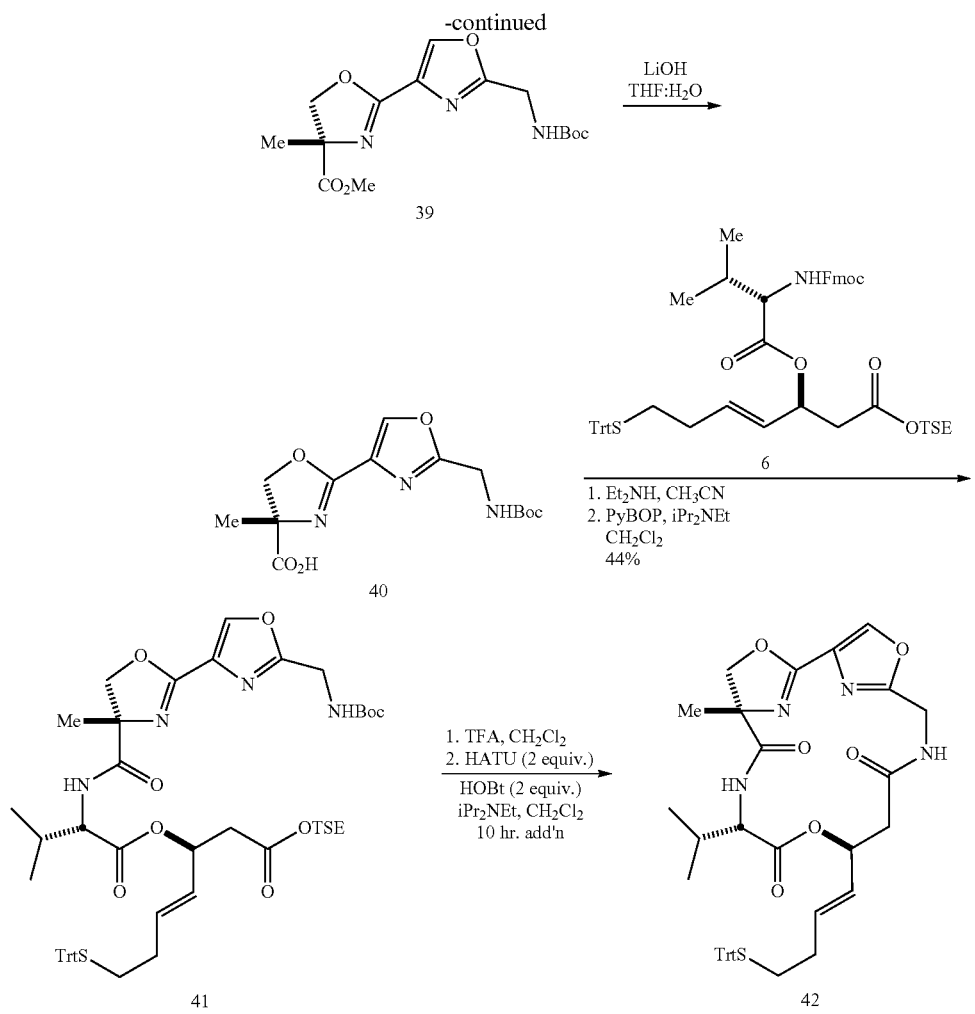

Having recently disclosed a concise, modular, and scalable total synthesis of Largazole and demonstrated its picomolar activity against HDACs 1, 2, and 3, as well as low nanomolar cytotoxicity against a number of chemoresistant cancer cell lines (Vanommeslaeghe, K., et al. 2005 *Bioorg. Med. Chem.* 13:6070-6082; Vanommeslaeghe, K., et al. 2005 *Bioorg. Med. Chem.* 13:3987-3992) and having disclosed a detailed conformation-activity relationship model for Largazole, FK228, and their corresponding amide isosteres with insights into the key contacts and associated spatial determinants that provide this remarkable level of activity (Somech, R., et al. 2004 *Cancer Treat. Rev.* 30:461; Miller, T. A., et al. 2003 *J. Med. Chem.* 46:5097-5116; Moradei, O., et al. 2005 *Curr. Med. Chem.; Anti-Cancer Agents* 5:529-560; Bolden, J. E., et al. 2006 *Nat. Rev. Drug Discovery* 5:769-784), described herein are efforts to modify the structural scaffold of Largazole in an effort to further define and expand structure-activity relationships within the family of macrocyclic HDACi's.

The previously reported route to Largazole proved highly reproducible and could be adapted to simple variants of the macrocyclic core (Bowers, A. A., et al. 2008 *J Am Chem Soc* 130:11219-22). Thus, milligram quantities of the C-2 epimer (3) and the enantiomer (2) of Largazole were easily accessible. Efforts to perturb the conformation of the macrocycle by imparting greater rigidity resulted in the replacement of the valine residue with proline (4). Compound 4 could be obtained in only slightly diminished overall yield via the same synthetic route deployed in the total synthesis of Largazole.

Scheme 1. Synthesis of Largazole-Azumamide Hybrid.

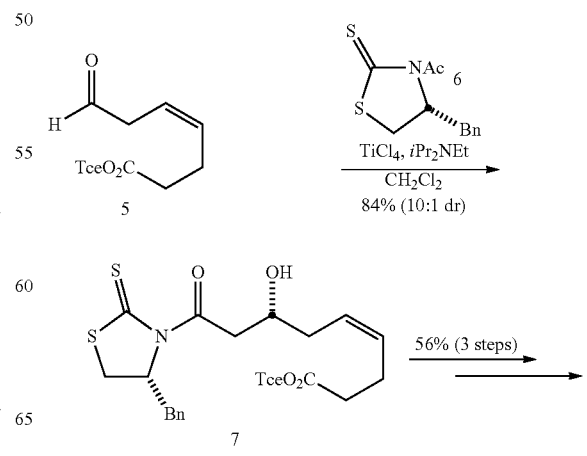

Scheme 2. Metathesis Route to Largazole Hybrids.

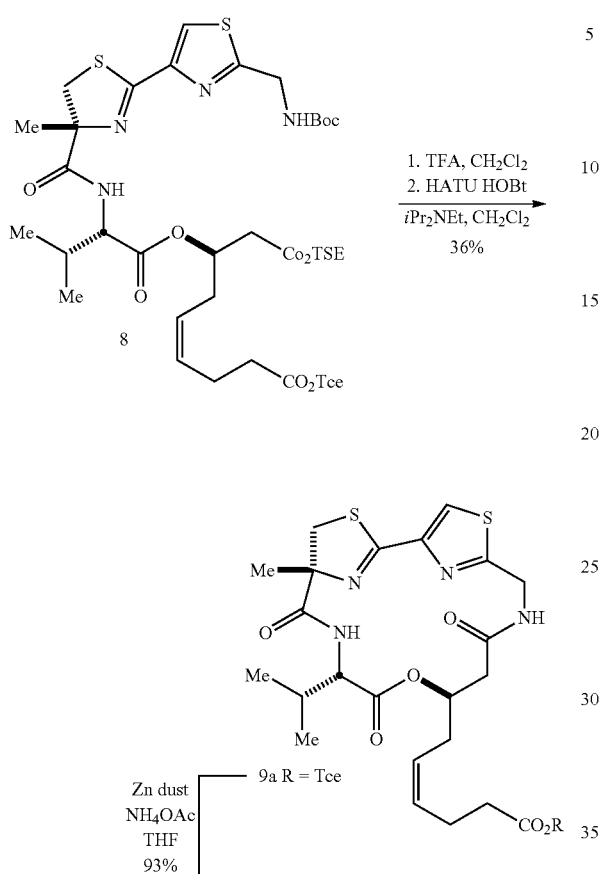

Two methods were employed to alter side chain functionality and access a series of Largazole chimeras. For the Largazole-Azumamide hybrid (9), the cis-geometry of the alkene residue necessitated its early introduction. Thus, aldol condensation of aldehyde 5 with thiazolidine-2-thione 6 provided the necessary β-hydroxy acid building block (7, Scheme 1, above). For other variants investigated, late-stage introduction of the zinc-binding side arms via cross metathesis proved expedient. Cross metathesis to attach the natural side-chain in their syntheses of Largazole itself was investigated (Nasveschuk, C. G., et al. 2008 *Org. Lett.* 10:3595-3598; Ghosh, A. K. and Kulkarni, S. 2008 *Org. Lett.* 10:3907-3909; Ying, Y., et al. 2008 *J. Am. Chem. Soc.* 130:8455-8459; Seiser, T.; et al. 2008 *Angew. Chem. Int. Ed.* 47:6483-6485).

For Largazole, the four-atom linker length relative to the thiol has been found to be optimal for maximum HDAC inhibition. However, literature precedent has shown that a four-to five-atom chain is optimal in small molecules bearing alternative zinc-binding functionality. Therefore, in the series of analogs prepared via metathesis, both the four- and the five-atom tethers were synthesized.

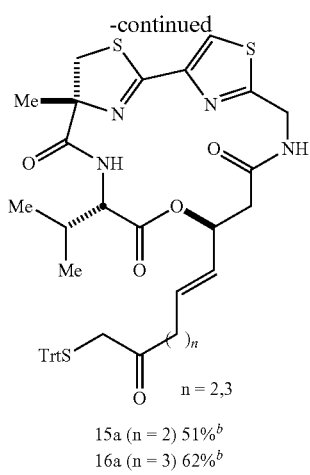

15a (n = 2) 51%[b]
16a (n = 3) 62%[b]

Conditions: (a) Grubb's 2nd generation (b) Hoveyda-Grubb's 2nd generation

Compounds 11 and 12 bear an α-aminobenzamide group. Meanwhile, compounds 13, 14 and 15, 16 contain α-thioamides and α-thioketones, respectively. These two motifs were identified as potential candidates in a computational study and have demonstrated promise in subsequent medicinal efforts (Furumai, R., et al. 2001 PNAS USA 98:87-92; Nishino, N., et al. 2003 Org Lett 5:5079-5082). Initial yields employing Grubb's second-generation ruthenium catalyst were low with poor conversion. The Hoveyda-Grubbs second-generation catalyst proved much more efficient. All Boc- and Trityl-protecting groups were removed prior to biological assay.

The significance of the methyl substituent on the thiazoline ring was also examined. Condensation of nitrile 17 with L-cysteine proved remarkably facile, proceeding in near quantitative yield (Scheme 3, below). Initial efforts at coupling to ester 19 provided poor yields of the desired acyclic precursor 20. The major product was thiazole-thiazole 21, resulting from in situ oxidation. Optimization of conditions for this coupling eventually allowed for up to 62% yield of the desired product. Oxidation could be the cause of the somewhat diminished yields in the cyclization of 20. Compound 23 could not be detected in NMR spectra of the crude reaction mixtures from cyclization of 20. Moreover, 23 could not be prepared directly from its acyclic precursor 21. Instead, oxidation of 22 under standard conditions provided 23. This macrocycle clearly contains some added constraint, as demonstrated by the presence of rotamers in the $^1$H NMR spectrum in CDCl$_3$. Both substrate 22a and 23a could be deprotected in good yield using standard conditions previously described.

Scheme 3. Synthesis of Cysteine & Thiazole-Thiazole Analogs.

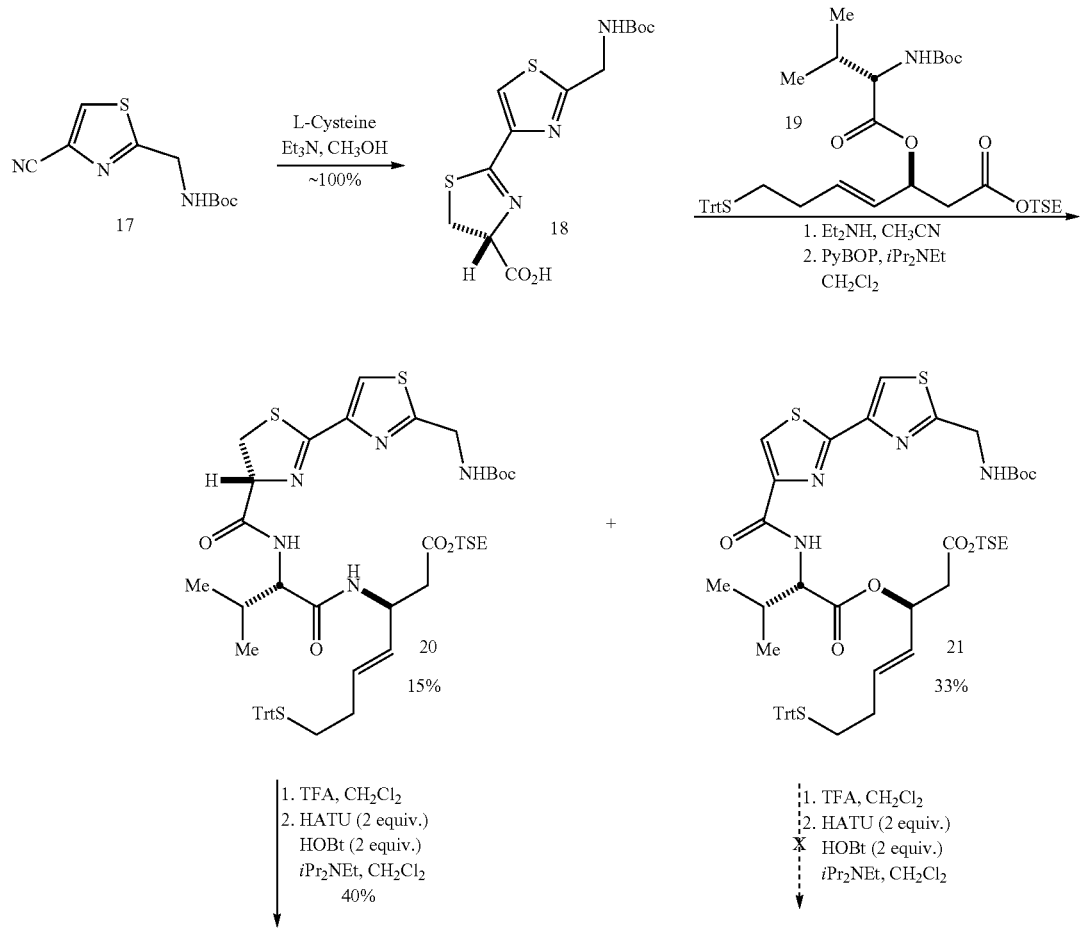

41

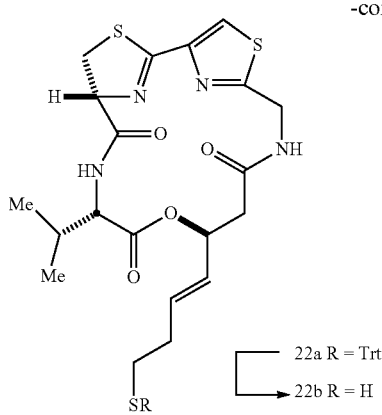

22a R = Trt
22b R = H

DBU,
BrCCl₃
—————→
CH₂Cl₂
52%

42

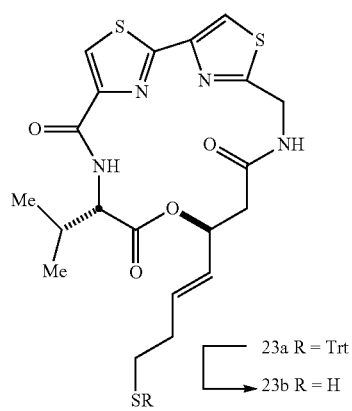

23a R = Trt
23b R = H

-continued

Replacement of the thiazole moiety with a pyridine residue in the heterocyclic backbone was readily ammenable to the synthetic strategy described herein (Scheme 4, below). Chloro-nitrile 24 could be Boc-protected and then condensed with α-methyl cysteine to provide acid 27. Subsequent deprotection, coupling, and cyclization provided analog 29.

Scheme 4. Synthesis of Thiazole to Pyridine Substitution.

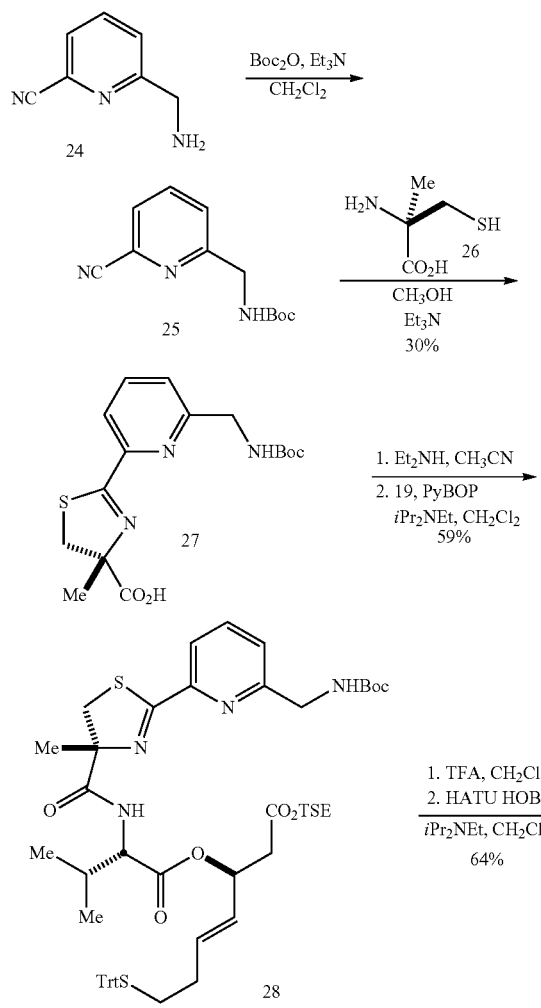

-continued

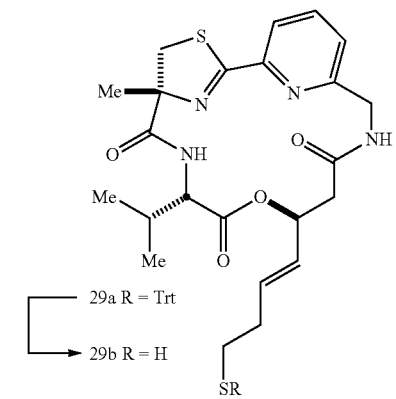

29a R = Trt
29b R = H

Additional single-atom replacements were performed within the largazole macrocyclic scaffold to interrogate very small structural and attendant conformational changes. Due to the inherent acid instability of oxazolines, additional protecting group manipulations were required for synthesis of oxazoline-oxazole substrate 39 (Scheme 5, below). Thus, oxazole 31 could be saponified and coupled to α-methyl serine (Taori, K., et al. 2008 *J. Am. Chem. Soc.* 130: 1806-1807 and 13506).

Switching the nitrogen protecting group then allowed for cyclization and deprotection/acylation with thiazolidine-2-thione 35 to obtain alcohol 36. Coupling to Fmoc-L-valine then provided the acyclic precursor 38.

Scheme 5. Synthesis of the Oxazoline-Oxazole Analog.

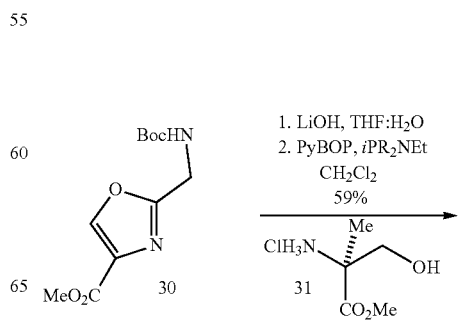

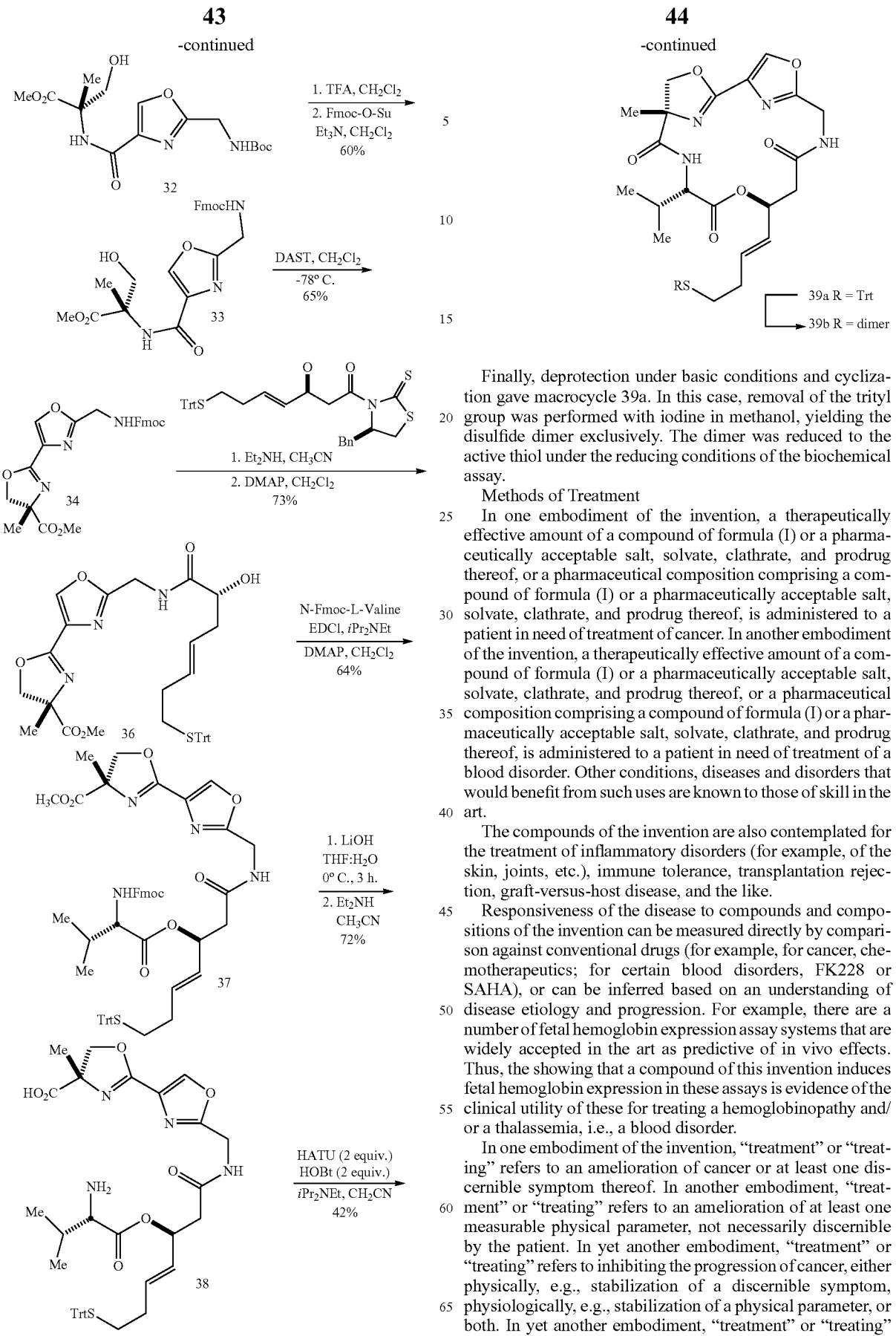

Finally, deprotection under basic conditions and cyclization gave macrocycle 39a. In this case, removal of the trityl group was performed with iodine in methanol, yielding the disulfide dimer exclusively. The dimer was reduced to the active thiol under the reducing conditions of the biochemical assay.

Methods of Treatment

In one embodiment of the invention, a therapeutically effective amount of a compound of formula (I) or a pharmaceutically acceptable salt, solvate, clathrate, and prodrug thereof, or a pharmaceutical composition comprising a compound of formula (I) or a pharmaceutically acceptable salt, solvate, clathrate, and prodrug thereof, is administered to a patient in need of treatment of cancer. In another embodiment of the invention, a therapeutically effective amount of a compound of formula (I) or a pharmaceutically acceptable salt, solvate, clathrate, and prodrug thereof, or a pharmaceutical composition comprising a compound of formula (I) or a pharmaceutically acceptable salt, solvate, clathrate, and prodrug thereof, is administered to a patient in need of treatment of a blood disorder. Other conditions, diseases and disorders that would benefit from such uses are known to those of skill in the art.

The compounds of the invention are also contemplated for the treatment of inflammatory disorders (for example, of the skin, joints, etc.), immune tolerance, transplantation rejection, graft-versus-host disease, and the like.

Responsiveness of the disease to compounds and compositions of the invention can be measured directly by comparison against conventional drugs (for example, for cancer, chemotherapeutics; for certain blood disorders, FK228 or SAHA), or can be inferred based on an understanding of disease etiology and progression. For example, there are a number of fetal hemoglobin expression assay systems that are widely accepted in the art as predictive of in vivo effects. Thus, the showing that a compound of this invention induces fetal hemoglobin expression in these assays is evidence of the clinical utility of these for treating a hemoglobinopathy and/or a thalassemia, i.e., a blood disorder.

In one embodiment of the invention, "treatment" or "treating" refers to an amelioration of cancer or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of cancer, either physically, e.g., stabilization of a discernible symptom, physiologically, e.g., stabilization of a physical parameter, or both. In yet another embodiment, "treatment" or "treating" refers to delaying the onset of cancer or symptoms thereof.

In another embodiment of the invention, "treatment" or "treating" refers to an amelioration of a hemoglobinopathy and/or a thalassemia, i.e., a blood disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a hemoglobinopathy and/or a thalassemia, i.e., a blood disorder, either physically, e.g., stabilization of a discernible symptom, physiologically, e.g., stabilization of a physical parameter, or both. In yet another embodiment, "treatment" or "treating" refers to delaying the onset of a hemoglobinopathy and/or a thalassemia, i.e., a blood disorder, or symptoms thereof.

The compounds of formula (I) or pharmaceutically acceptable salts, solvates, clathrates, and prodrugs thereof can be assayed in vitro or in vivo, for the desired therapeutic or prophylactic activity, prior to use in humans. For example, animal model systems can be used to demonstrate the safety and efficacy of compounds of this invention.

Without wishing to be bound by theory, it is believed that the compounds and compositions of this invention induce gene expression, for example, BDNF (for psychiatric disease), HbF, SMA, p53, and/or p21 expression and, as a result, may be used to treat or prevent cancer. Further without wishing to be bound by theory, it is believed that the compounds and compositions of this invention induce gene expression, for example, fetal hemoglobin expression and, as a result, may be used to treat or prevent a hemoglobinopathy and/or a thalassemia, i.e., a blood disorder. It should be noted, however, that the compounds might act by a secondary or a different activity, such as, without limitation, delaying the normally fixed fetal-to-adult globin gene switch or stimulating hematopoiesis, erythropoiesis, myelopoiesis and/or neutrophil production.

Pharmaceutical Compositions

In one embodiment, pharmaceutical compositions and dosage forms of the invention comprise a compound of formula (I) or a pharmaceutically acceptable prodrug, salt, solvate, or clathrate thereof, in relative amounts and formulated in such a way that a given pharmaceutical composition or dosage form reduces or inhibits the growth of transformed (cancer) cells. In another embodiment of the invention, such pharmaceutical compositions and dosage forms comprise one or more additional active agents such as chemotherapeutic agents known in the art.

In another embodiment, pharmaceutical compositions and dosage forms of the invention comprise a compound of formula (I) or a pharmaceutically acceptable prodrug, salt, solvate, or clathrate thereof, in relative amounts and formulated in such a way that a given pharmaceutical composition or dosage form induces the expression of fetal hemoglobin. In another embodiment of the invention, such pharmaceutical compositions and dosage forms comprise one or more additional active agents.

The compounds of the invention and pharmaceutically acceptable salts thereof can be administered via, for example, the oral, parenteral, topical, rectal, subcutaneous, transdermal, pulmonary (inhaled) routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

In one embodiment, the pharmaceutical compositions of the invention may be administered alone or in combination with other known compositions for treating cancer in a subject, e.g., a mammal. Preferred mammals include cats, dogs, pigs, rats, mice, monkeys, chimpanzees, baboons and humans. In one embodiment, the subject is suffering from cancer. In another embodiment, the subject is at risk of suffering from cancer.

In another embodiment, the pharmaceutical compositions of the invention may be administered alone or in combination with other known compositions for treating blood disorders in a subject, e.g., a mammal. Preferred mammals include cats, dogs, pigs, rats, mice, monkeys, chimpanzees, baboons and humans. In one embodiment, the subject is suffering from a blood disorder. In another embodiment, the subject is at risk of suffering from a blood disorder.

The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating cancer or blood disorders can be used in the methods of the invention.

The compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is derivatized with differentially degradable coatings, e.g., by microencapsulation, multiple coatings, etc.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

It will also be understood that normal, conventionally known precautions will be taken regarding the administration of the compounds of the invention generally to ensure their efficacy under normal use circumstances. Especially when employed for therapeutic treatment of humans and animals in vivo, the practitioner should take all sensible precautions to avoid conventionally known contradictions and toxic effects.

The composition, shape, and type of dosage forms of the invention will typically vary depending on their use. For example, a dosage form suitable for mucosal administration may contain a smaller amount of active ingredient(s) than an oral dosage form used to treat the same indication. This aspect of the invention will be readily apparent to those skilled in the art, e.g., Remington's Pharmaceutical Sciences (1990) 18th ed., Mack Publishing, Eastern Pa.

The invention further encompasses pharmaceutical compositions and dosage forms that comprise one or more compounds that reduce the rate by which the compound of the invention will decompose. Such compounds, which are referred to herein as "stabilizer" include, but are not limited to, antioxidants such as ascorbic acid, pH buffers, or salt buffers.

The interrelationship of dosages for animals and humans (based on milligrams per meter squared of body surface) is described in Freireich, et al. 1966 *Cancer Chemother Rep* 50: 219. Body surface area may be approximately determined from height and weight of the patient, e.g., Scientific Tables, Geigy Pharmaceuticals, Ardley, N.Y., 1970, 537.

Like the amounts and types of excipients, the amount of the compound of the invention in a dosage form may differ depending on factors such as, but not limited to, the route by which it is to be administered to subjects. It is within the skill of the art to determine the appropriate dose and dosage form for a given patient.

Furthermore, the invention also pertains to the use of a compound of the invention for the preparation of a medicament. In one embodiment of the invention, the medicament may include a pharmaceutically acceptable carrier and the compound is an effective amount, e.g., an effective amount to treat cancer. In another embodiment of the invention, the medicament may include a pharmaceutically acceptable carrier and the compound is an effective amount, e.g., an effective amount to treat a blood disorder.

Kits

In one aspect, the invention provides kits comprising a unit dosage form of an effective amount of a compound of formula (I) or a pharmaceutically acceptable prodrug, salt, solvate, hydrate, or clathrate thereof, and a device that can be used to administer the compound. Examples of such devices include, but are not limited to, syringes, drip bags, patches, and inhalers.

Kits of the invention can further comprise pharmaceutically acceptable vehicles. For example, if a compound of the invention is provided in a solid form that must be reconstituted for parenteral administration, the kit can comprise a sealed container of a suitable vehicle in which the compound can be dissolved to form a particulate-free sterile solution that is suitable for parenteral administration.

Combination Therapy

The herein-described methods for treating a hemoglobinopathy and/or a thalassemia, i.e., a blood disorder, in a subject can further comprise administering to the subject being administered a compound of this invention, an effective amount of one or more other therapeutic agents. In one embodiment of the invention where another therapeutic agent is administered to a subject, the effective amount of the compound of the invention is less than its effective amount would be where the other therapeutic agent is not administered. In another embodiment, the effective amount of the other therapeutic agent is less than its effective amount would be where the compound of the invention is not administered.

In some aspects described herein, the method includes an additional therapeutic modality. For example, the additional therapeutic modality is radiation therapy or a cytotoxic chemotherapy agent, such as an anti-metabolite (e.g., 5-FU, with leucovorin), irinotecan, (or other topoisomerase inhibitor), doxorubicin, or any combination all of these agents, including administration of all of these agents.

The methods can further include the step of monitoring the subject, e.g., for a reduction in one or more of: a reduction in tumor size; reduction in cancer markers, e.g., levels of cancer specific antigen; reduction in the appearance of new lesions, e.g., in a bone scan; a reduction in the appearance of new disease-related symptoms; or decreased or stabilization of size of soft tissue mass; or any parameter related to improvement in clinical outcome. The subject can be monitored in one or more of the following periods: prior to beginning of treatment; during the treatment; or after one or more elements of the treatment have been administered. Monitoring can be used to evaluate the need for further treatment with the compound of Formula (I) or for additional treatment with additional agents. Generally, a decrease in or stabilization of one or more of the parameters described above is indicative of the improved condition of the subject. Information about the monitoring can be recorded, e.g., in electronic or digital form.

The treatment methods disclosed herein can be used in combination with one or more additional treatment modalities, including, but not limited to: surgery; radiation therapy, and chemotherapy.

With reference to the methods disclosed herein, the term "combination" refers to the use of one or more additional agents or therapies to treat the same patient, wherein the use or action of the agents or therapies overlap in time. The additional agents or therapies can be administered at the same time as the compound of Formula (I) is administered, or sequentially in any order. Sequential administrations are administrations that are given at different times. The time between administration of the one agent and another agent can be minutes, hours, days, or weeks.

The additional agent or therapy can also be another anti-cancer agent or therapy. Nonlimiting examples of anti-cancer agents include, e.g., anti-microtubule agents, topoisomerase inhibitors, antimetabolites, mitotic inhibitors, alkylating agents, intercalating agents, agents capable of interfering with a signal transduction pathway, agents that promote apoptosis, radiation, and antibodies against other tumor-associated antigens (including naked antibodies, immunotoxins and radioconjugates). Examples of the particular classes of anti-cancer agents are provided in detail as follows: antitubulin/antimicrotubule, e.g., paclitaxel, vincristine, vinblastine, vindesine, vinorelbin, taxotere; topoisomerase I inhibitors, e.g., irinotecan, topotecan, camptothecin, doxorubicin, etoposide, mitoxantrone, daunorubicin, idarubicin, teniposide, amsacrine, epirubicin, merbarone, piroxantrone hydrochloride; antimetabolites, e.g., 5-fluorouracil (5-FU), methotrexate, 6-mercaptopurine, 6-thioguanine, fludarabine phosphate, cytarabine/Ara-C, trimetrexate, gemcitabine, acivicin, alanosine, pyrazofurin, N-Phosphoracetyl-L-Asparate=PALA, pentostatin, 5-azacitidine, 5-Aza 2'-deoxycytidine, ara-A, cladribine, 5-fluorouridine, FUDR, tiazofurin, N-[5-[N-(3,4-dihydro-2-methyl-4-oxoquinazolin-6-ylmethyl)-N-methylamino]—2-thenoyl]-L-glutamic acid; alkylating agents, e.g., cisplatin, carboplatin, mitomycin C, BCNU=Carmustine, melphalan, thiotepa, busulfan, chlorambucil, plicamycin, dacarbazine, ifosfamide phosphate, cyclophosphamide, nitrogen mustard, uracil mustard, pipobroman, 4-ipomeanol; agents acting via other mechanisms of action, e.g., dihydrolenperone, spiromustine, and desipeptide; biological response modifiers, e.g., to enhance anti-tumor responses, such as interferon; apoptotic agents, such as actinomycin D; and anti-hormones, for example anti-estrogens such as tamoxifen or, for example antiandrogens such as 4'-cyano-3-(4-fluorophenylsulphonyl)-2-hydroxy-2-methyl-3'-(trifluoromethyl)propionanilide.

A combination therapy can include administering an agent that reduces the side effects of other therapies. The agent can be an agent that reduces the side effects of anti-cancer treatments. A combinational therapy can also include administering an agent that reduces the frequency of administration of other therapies. The agent can be an agent that decreases growth of tumor after the anti-cancer effects of other therapies have decreased.

Useful combination therapies will be understood and appreciated by those of skill in the art. Potential advantages of such combination therapies include the ability to use less of each of the individual active ingredients to minimize toxic side effects, synergistic improvements in efficacy, improved ease of administration or use, and/or reduced overall expense of compound preparation or formulation. For example, the compounds of the invention may be administered to the subject for treatment of a hemoglobinopathy and/or a thalassemia, i.e., a blood disorder, in combination with one or more cytokines. In one embodiment, the cytokine is selected from the group consisting of IL-3, GM-CSF, G-CSF, stem cell factor (SCF) and IL-6.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description and the examples that follow, one skilled in the art can easily ascertain the essential characteristics of the present invention, and without departing from the spirit and scope thereof, can make various changes and modifications of the invention to adapt it to various usages and conditions. For example, the compounds of the invention may be used as research tools (for example, to isolate new targets for performing drug discovery). The compounds may, for instance, be radiolabelled for imaging tissue or organs or be used to form bioconjugates for affinity assays. These and other uses and embodiments of the compounds and compositions of this invention will be apparent to those of ordinary skill in the art.

The disclosure also encompasses all possible permutations of the claim set, as if they were multiple dependent claims.

Various embodiments of the disclosure could also include permutations of the various elements recited in the claims as if each dependent claim was multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described was chosen and described in order to best explain the principles of the invention, the practical application, and to enable others of ordinary skill in the art to understand the invention for various embodiments with various modifications as are suited to the particular use contemplated.

The invention is further defined by reference to the following examples describing in detail the preparation of compounds of, the invention. It will be apparent to those skilled in the art that many modifications, both to materials and methods, may be practiced without departing from the purpose and interest of this invention. The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

The following examples are provided for illustrative purposes only and are not intended to limit the scope of the invention.

General Experimental Methods

Unless otherwise noted, all reactions were run under an argon atmosphere in flame or oven dried glassware. Reactions were monitored using thin layer silica gel chromatography (TLC) using 0.25 mm silica gel 60F plates with fluorescent indicator (Merck). Plates were visualized by treatment with phosphomolybdic acid stain with gentle heating. Products were purified via column chromatography using the solvent system(s) indicated. Silica gel 60, 230-400 mesh (Sorbent Technologies). Tetrahydrofuran (THF), dichloromethane ($CH_2Cl_2$), acetonitrile ($CH_3CN$), triethylamine ($Et_3N$), toluene, diethyl ether ($Et_2O$), and N,N-dimethylformamide (DMF) were passed through an alumina drying column (Solv-Tek Inc.) using argon pressure. Melting points were determined in open-ended capillaries and are uncorrected. $^1H$ NMR and $^{13}C$ NMR spectra were recorded on Varian 300, 400, or 500 MHz NMR spectrometers. Chemical shifts are reported in ppm relative to $CHCl_3$ at $\delta=7.27$ ($^1H$ NMR) and $\delta=77.23$ ($^{13}C$ NMR) or tetramethylsilane (TMS) $\delta=0.00$, where noted. Mass spectra were obtained on Fisions VG Autospec. Optical rotations were collected at 589 nm on a Rudolph Research Automatic Polarimeter Autopol III.

Example 1

Synthesis of Largazole and Largazole Thiol

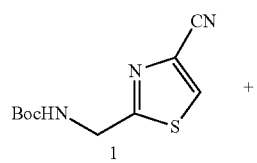

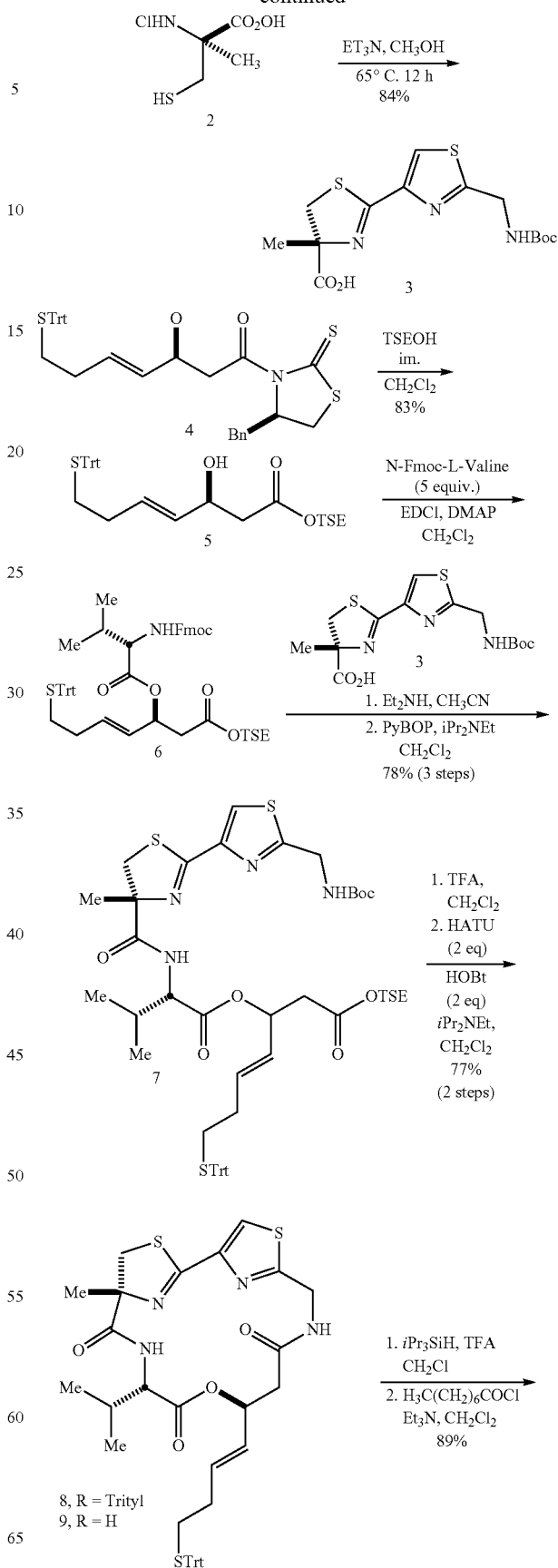

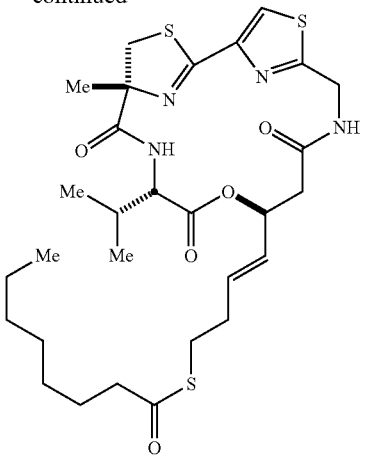

10, Largazole 0.800 g (3.3 mmol) Thiazole nitrile 1 (Videnov, G., et al. 1996 *Angew Chem Int Ed Eng* 35:1503-1506; Lange, U. E. W., et al. 1999 *Tetrahedron Lett* 40:7067-7070) and 1.00 g (5.3 mmol, 1.6 equiv.) α-methyl-cysteine-HCl 2 (Jeanguenat, A. and Seebach 1991 *J Chem Soc, Perkins Trans* 1:2291-2298; Mulqueen, G. C., et al. 1993 *Tetrahedron* 49:5359-5364) were dissolved 50 mL dry CH$_3$OH and 0.75 mL dry Et$_3$N was added dropwise. The resulting solution was heated at reflux overnight. The reaction was subsequently cooled to room temperature and the solvents removed in vaccuo. The crude reaction mixture was then dissolved in sat. aqu. NaHCO$_3$ and washed with diethyl ether. The aqueous layer was then acidified to pH ~3-4 by dropwise addition of 3N HCl and extracted with EtOAc (3×30 mL). The combined organics were dried over Na$_2$SO$_4$, filtered, and concentrated to provide 1.00 g (2.8 mmol, 84% yield) of 2-{2-[(tert-Butoxycarbonyl)methyl]thiazol-4-yl}-4-methyl-4,5-dihydrothiazole-4-carboxylic acid (3) in spectroscopically pure form. Clear oil. [α]$^{24}$$_D$: +30.9 (c=1, CH$_3$OH). $^1$H NMR (400 MHz, CDCl$_3$) δ 9.79 (bs, 1H), 7.98 (s, 1H), 5.59 (s, 1H), 4.59 (d J=6.3 Hz, 2H), 3.88 (d J=11.4 Hz, 1H), 3.30 (d J=11.4 Hz, 1H), 1.66 (s, 3H). $^{13}$C NMR (100.6 MHz, CDCl$_3$): δ 175.74, 170.38, 170.16, 165.03, 155.91, 147.77, 123.3, 84.23, 80.70, 42.39, 41.31, 28.51, 27.17, 26.67, 24.30. HRMS (ESI): m/z calcd. for C$_{14}$H$_{19}$N$_3$NaO$_4$S$_2$ (M+Na)$^+$380.07147. found 380.07165.

0.200 g (0.33 mmol) thiazoline-thione 4 (Yurek-George, A., et al. 2004 *J Am Chem Soc* 126:1030-1031) was dissolved in 5 mL CH$_2$Cl$_2$ and 0.470 mL (3.3 mmol, 10.0 equiv.) 2-trimethylsilyethanol was added, followed by 0.033 g (0.49 mmol, 1.5 equiv.) imidazole. The resulting solution was stirred overnight, when TLC revealed complete disappearance of starting material 4. The reaction mixture was concentrated in vaccuo and submitted immediately to column chromatography (elutes 4:1 hexanes:ethyl acetate), which provided 0.142 g (83% yield) of the protected ester, (3S,4E)-3-Hydroxy-7-[(triphenylmethyl)thio]-4-heptenoic acid (2-trimethylsilyl)ethyl ester (5), as a clear oil. [α]$^{24}$$_D$: -1.1 (c=2, CHCl$_3$). $^1$H NMR (400 MHz, CDCl$_3$) δ 7.40 (dd J=0.8, 8.8 Hz, 6H), 7.24-7.28 (m, 6H), 7.17-7.21 (m, 3H), 5.56 (dt J=6.4, 15.2 Hz, 1H), 5.40 (dd J=6.4, 15.2 Hz, 1H), 4.40-4.45 (m, 1H), 4.16-4.21 (m, 2H), 2.48 (dd J=4.8, 16.4 Hz, 1H), 2.43 (dd J=8.0, 16.4 Hz, 1H), 2.18-2.22 (m, 2H), 2.04-2.09 (m, 2H), 0.96-1.00 (m, 2H), 0.03 (s, 9H). $^{13}$C NMR (100.6 MHz, CDCl$_3$): δ 172.7, 145.1, 132.2, 130.3, 129.8, 128.1, 126.8, 68.8, 66.8, 63.3, 41.7, 31.7, 31.6, 17.5, -1.3. HRMS (ESI): m/z calcd. for C$_{31}$H$_{38}$NaO$_3$SSi (M+Na)$^+$541.22086. found 541.22072.

0.570 g (1.1 mmol) of β-hydroxy ester 5 and 1.865 g (5.5 mmol, 5 equiv.) N-Fmoc-L-valine were dissolved in 20 mL dry CH$_2$Cl$_2$. The reaction was cooled to 0° C. and 1.264 g (6.6 mmol, 6 equiv.) EDCI and 0.007 g (0.11 mmol, 0.1 equiv.) DMAP were added in ~5 mL CH$_2$Cl$_2$, followed by 1.15 mL iPr$_2$NEt. The reaction was allowed to warm to room temperature and stirred overnight, when TLC showed complete disappearance of 5. The reaction was concentrated and passed through a short plug of silica, washing with 100% EtOAc. The product diester eluted with a by-product from the excess amino acid used, which was not separated at this time. Instead, the crude diester was taken up in 50 mL CH$_3$CN (to ~0.02M) and treated with 5 mL diethylamine (to ~0.2M). The resulting solution was stirred for two hours and then concentrated, taken up in EtOAc, and concentrated again.

0.400 g (1.2 mmol, 1.1 equiv.) acid 3 was dissolved in 20 mL dry CH$_2$Cl$_2$ and treated with 1.020 g (2 mmol, 2.0 equiv) PyBOP and 0.510 mL (2.9 mmol, 3.0 equiv.) iPr$_2$NEt. After stirring for ~5 min., the crude amine in 10 mL CH$_3$CN was added to the mixture dropwise. After 2 hrs, the reaction was concentrated and submitted immediately to column chromatography, 0.820 g (0.86 mmol, 78% from 5) of (3S,4E)-2-(Trimethylsilyl)ethyl-3-[(S)-2-(R)-2-[2-[(tert-butoxycarbonyl)methyl]thiazol-4-yl]-4-methyl-4,5-dihydrothiazole-4-carboxamido)-3-methylbutanoyloxy]-7-(tritylthio)hept-4-enoate (7) eluting cleanly in (1:1 hexanes:EtOAc). Clear oil. $^1$H NMR (300 MHz, CDCl$_3$) δ 7.91 (s, 1H), 7.36-7.41 (m, 6H), 7.16-7.29 (m, 9H), 5.59-5.71 (m, 2H), 5.36 (dd J=7.5, 15.3 Hz, 1H), 5.30 (s, 1H), 4.62 (d J=6.0 Hz, 2H), 4.48 (dd J=4.8, 9.3 Hz, 1H), 4.12-2.18 (m, 2H), 3.77 (d J=11.4 Hz, 1H), 3.32 (d J=11.4 Hz, 1H), 2.69 (dd J=8.1, 15.9 Hz, 1H), 2.54 (dd J=5.1, 15.9 Hz, 1H), 2.03-2.18 (m, 5H), 1.57 (s, 3H), 1.47 (s, 9H), 0.93-0.99 (m, 2H), 0.81 (d J=6.9 Hz, 3H), 0.74 (d J=6.9 Hz, 3H), 0.02 (s, 9H). $^{13}$C NMR (75.5 MHz, CDCl$_3$): δ 174.6, 170.6, 169.9, 155.8, 148.8, 145.0, 134.2, 129.7, 128.1, 128.0, 126.8, 121.7, 85.3, 80.7, 77.5, 72.0, 66.8, 63.4, 57.0, 42.5, 41.7, 39.9, 31.5, 31.4, 31.3, 28.5, 25.0, 19.3, 17.7, 17.5, -1.3. HRMS (ESI): m/z calcd. for C$_{50}$H$_{64}$N$_4$NaO$_7$S$_3$Si (M+Na)$^+$979.36041. found 979.36045.

0.100 g (0.1 mmol) Acyclic precursor 7 was dissolved in 5 mL CH$_2$Cl$_2$ (to ~0.03M), cooled to 0° C. and treated with 1 mL TFA (to ~0.6M). The reaction was allowed to warm to room temperature and stirred overnight (shorter reaction times resulted in only partial deprotection of the TSE group). Solvents were evaporated and the crude amino acid redissolved in toluene and concentrated a second time to remove residual TFA. The crude amino acid was then taken up in ~5 mL CH$_2$Cl$_2$ and added dropwise to a stirred solution of 0.115 mL (6.0 equiv.) iPr$_2$Net in 100 mL dry CH$_3$CN (to ~0.001M). The resulting moderately opaque solution was allowed to stir ~10 min., before 0.085 g (0.2 mmol, 2 equiv.) HATU and 0.030 g (0.2 mmol, 2 equiv.) HOBt were added dropwise in ~5 mL CH$_3$CN. The reaction was allowed to stir for 16 hr., then concentrated and submitted immediately to column chromatography. S-Trityl macrocycle (8) (0.060 g, 77% yield) eluted quickly in EtOAc, after a general wash with 10:1 hexanes: EtOAc. Clear oil. [α]$^{24}$$_D$: +16.1 (c=1, CH$_3$OH). $^1$H NMR (400 MHz, CDCl$_3$) δ 7.72 (s, 1H), 7.30-7.33 (m, 6H), 7.19-7.24 (m, 6H), 7.11-7.15 (m, 3H), 7.08 (d J=9.6 Hz, 1H), 6.47 (d J=6.8 Hz, 1H), 5.65 (dt J=7.2, 15.6 Hz, 1H), 5.59 (t J=6.0 Hz, 1H), 5.32 (dd J=6.0, 15.6 Hz, 1H), 5.13 (dd J=8.4, 17.6 Hz, 1H), 4.49 (dd J=3.2, 9.6 Hz, 1H), 4.03 (d J=17.6 Hz, 1H), 3.98 (d J=11.6 Hz, 1H), 3.22 (d J=11.6 Hz, 1H), 2.73 (dd J=9.6, 15.6 Hz, 1H), 2.57 (dd J=2.4, 15.6 Hz, 1H), 2.09-2.16

(m, 2H), 1.92-2.04 (m, 3H), 1.77 (s, 3H), 0.60 (d J=6.8 Hz, 3H), 0.43 (d J=6.8 Hz, 3H). $^{13}$C NMR (100.6 MHz, CDCl$_3$): δ 173.3, 169.6, 168.9, 168.4, 147.1, 145.0, 133.4, 129.8, 128.1, 127.5, 126.9, 77.5, 72.1, 66.8, 58.1, 43.5, 41.2, 40.8, 34.3, 31.6, 31.5, 19.1, 17.0. HRMS (ESI): m/z calcd. for C$_{40}$H$_{42}$N$_4$NaO$_4$S$_3$ (M+Na)$^+$761.22659. found 761.22598.

0.030 g (0.04 mmol) S-Trityl macrocycle 8 was dissolved in 5 mL dry CH$_2$Cl$_2$ and cooled to 0° C. The mixture was successively treated with 0.017 mL (0.08 mmol, 2 equiv.) iPr$_3$SiH and 0.200 mL TFA (to ~0.2M in 8). The reaction mixture was allowed to warm to room temperature and stirred for 2 hrs before being concentrated and chromatographed (EtOAc) to provide 0.019 g (0.038 mmol, 95%) thiol 9. Clear oil. [α]$^{24}_D$: +11.0 (c=1, CHCl$_3$). $^1$H NMR (400 MHz, CDCl$_3$) δ 7.70 (s, 1H), 7.10 (d J=9.2 Hz, 1H), 6.43 (d J=6.8 Hz, 1H), 5.75 (dt J=8.4, 15.2 Hz, 1H), 5.58-5.63 (m, 1H), 5.45 (dd J=6.8, 15.2, 1H), 5.20 (dd J=9.2, 17.4 Hz, 1H), 4.53 (dd J=3.6, 9.6 Hz, 1H), 4.20 (dd J=2.4, 17.4 Hz, 1H), 3.96 (d J=11.2 Hz, 1H), 3.20 (d J=11.2 Hz, 1H), 2.79 (dd J=10.0, 16.8 Hz, 1H), 2.62 (dd J=2.8, 16.8 Hz, 1H), 2.48 (q J=7.2 Hz, 2H), 2.27-2.30 (m, 2H), 1.99-2.04 (m, 2H), 1.79 (s, 3H), 0.60 (d J=6.8 Hz, 3H), 0.43 (d J=6.8 Hz, 3H). $^{13}$C NMR (100.6 MHz, CDCl$_3$): δ 173.7, 169.6, 169.1, 168.2, 147.5, 132.8, 129.0, 124.6, 84.5, 77.5, 72.4, 58.0, 43.6, 41.3, 40.8, 36.6, 34.4, 24.4, 24.1, 19.1, 16.9. HRMS (ESI): m/z calcd. for C$_{21}$H$_{29}$N$_4$O$_4$S$_3$ (M+H)$^+$ 497.13509. found 497.13462.

0.010 g (0.020 mmol) thiol 9 was dissolved in 2 mL dry CH$_2$Cl$_2$ and cooled to 0° C. The mixture was successively treated with 0.010 mL (0.040 mmol, 2 equiv.) Et$_3$N and 0.021 mL (0.10 mmol, 5 equiv.) octanoyl chloride. The reaction was allowed to warm to room temperature and stirred for 2 hrs, when TLC showed complete disappearance of starting material in favor of a less polar compound. The reaction was cooled to 0° C. and quenched with 5 mL CH$_3$OH, before being concentrated and chromatographed (EtOAc) to provide 0.012 g (0.019 mmol, 94% yield) largazole 10. Clear oil. [α]$^{24}_D$: +25.9 (c=1, CH$_3$OH); lit.: [α]$^{24}_D$: +22 (c=0.1, CH$_3$OH). $^1$H NMR (400 MHz, CDCl$_3$) δ 7.77 (s, 1H), 7.15 (d J=9.6 Hz, 1H), 6.49 (bs, 1H), 5.82 (dt J=6.9, 15.6 Hz, 1H), 5.66 (t J=6.3 Hz, 1H), 5.50 (dd J=6.6, 15.6 Hz, 1H), 5.29 (dd J=7.8, 17.7 Hz, 1H), 4.60 (dd J=2.7, 8.7 Hz, 1H), 4.26 (d J=17.1 Hz, 1H), 4.05 (d J=11.4 Hz, 1H), 3.27 (d J=11.4 Hz, 1H), 2.89 (t J=6.9 Hz, 2H0, 2.84 (d J=14.7 Hz, 1H), 2.68 (d J=14.7 Hz, 1H), 2.53 (t J=7.2 Hz, 2H), 2.27-2.36 (m, 2H), 2.08-2.13 (m, 1H), 1.87 (s, 3H0, 1.61-1.66 (m, 2H), 1.25-1.29 (m, 8H), 0.87 (t J=7.2 Hz, 3H), 0.68 (d J=6.6 Hz, 3H), 0.50 (d J=6.6 Hz, 3H). $^{13}$C NMR (100.6 MHz, CDCl$_3$): δ 199.6, 173.7, 169.7, 169.1, 168.2, 147.5, 133.0, 128.6, 124.6 84.5, 72.3, 58.0, 44.4, 43.6, 41.4, 40.7, 34.5, 32.5, 31.9, 29.3, 29.2, 28.2, 25.9, 24.4, 22.9, 19.1, 16.9, 14.3. HRMS (ESI): m/z calcd. for C$_{29}$H$_{42}$N$_4$NaO$_5$S$_3$ (M+Na)$^+$645.22150. found 645.22103.

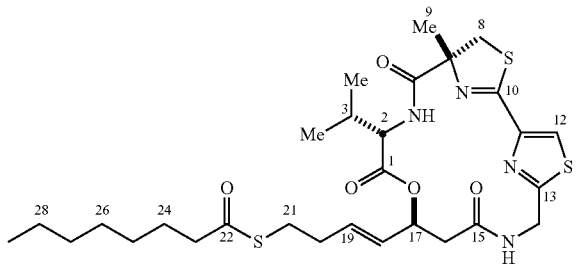

TABLE 1

Comparison of $^1$H and $^{13}$C NMR Spectra of Natural (Isolated)[4] and Synthetic Largazole (1).

| C/H no. | Natural | Synthetic | Natural | Synthetic |
|---|---|---|---|---|
| 1 | | | 168.9, qC | 169.1, qC |
| 2 | 4.61 (dd J = 9.2, 3.3) | 4.60 (dd J = 9.0, 3.3) | 57.7, CH | 58.0, CH |
| 3 | 2.10 (m) | 2.11 (m) | 34.2, CH | 34.5, CH |
| 4 | 0.68 (d J = 7.2) | 0.68 (d J = 6.9) | 18.9, CH$_3$ | 19.1, CH$_3$ |
| 5 | 0.50 (d J = 7.2) | 0.50 (d J = 6.9) | 16.6, CH$_3$ | 16.9, CH$_3$ |
| 2-NH | 7.15 (d J = 9.2) | 7.15 (d J = 9.3) | | |
| 6 | | | 173.5, qC | 173.7, qC |
| 7 | | | 84.4, qC | 84.5, qC |
| 8a | 4.04 (d J = 11.4) | 4.05 (d J = 11.4) | 43.3, CH$_2$ | 43.6, CH$_2$ |
| 8b | 3.27 (d J = 11.4) | 3.27 (d J = 11.4) | | |
| 9 | 1.87 (br s) | 1.87 (br s) | 24.2, CH$_3$ | 24.4, CH$_3$ |
| 10 | | | 164.6, qC | 165, qC |
| 11 | | | 147.4, qC | 147.5, qC |
| 12 | 7.76 (s) | 7.77 (s) | 124.4, CH | 124.6, CH |
| 13 | | | 167.9, qC | 168.2, qC |
| 14a | 5.29 (dd J = 17.4, 9.6) | 5.29 (dd J = 17.4, 9.6) | 41.1, CH | 41.4, CH |
| 14b | 4.27 (dd J = 17.4, 2.5) | 4.26 (dd J = 17.7, 3.3) | | |
| 14-NH | 6.45 (dd J = 9.6, 2.5) | 6.49 (dd J = 9.6, 3.0) | | |
| 15 | | | 169.4, qC | 169.7, qC |
| 16a | 2.86 (dd J = 16.5, 10.5) | 2.84 (dd J = 16.8, 10.5) | 40.5, CH$_2$ | 40.7, CH$_2$ |
| 16b | 2.68 (dd J = 16.5, 1.8) | 2.68 (dd J = 16.2, 2.7) | | |
| 17 | 5.66 (ddd J = 10.5, 7.2, 1.8) | 5.66 (ddd J = 9.9, 6.9, 2.7) | 72.0, CH | 72.3, CH |
| 18 | 5.51 (dd J = 15.6, 7.2) | 5.50 (dd J = 15.6, 6.6) | 128.4, CH | 128.6, CH |
| 19 | 5.82 (dt J = 15.6, 7.2) | 5.82 (dt J = 15.6, 6.9) | 132.7, CH | 133.0, CH |
| 20 | 2.31 (br q J = 7.2 2H) | 2.30 (br q J = 7.2 2H) | 32.3, CH$_2$ | 32.5, CH$_2$ |
| 21 | 2.90 (t J = 7.2 2H) | 2.89 (t J = 6.9 2H) | 27.9, CH$_2$ | 28.2, CH$_2$ |
| 22 | | | 199.4, qC | 199.6, qC |
| 23 | 2.52 (t J = 7.5 2H) | 2.53 (t J = 7.2 2H) | 44.1, CH$_2$ | 44.4, CH$_2$ |
| 24 | 1.64 (m 2H) | 1.64 (m 2H) | 25.6, CH$_2$ | 25.9, CH$_2$ |
| 25 | 1.29 (m 2H) | 1.25-1.29 (m 8H) | 28.9, CH$_2$ | 29.2, CH$_2$ |
| 26 | 1.25 (m 2H) | | 28.9, CH$_2$ | 29.3, CH$_2$ |
| 27 | 1.26 (m 2H) | | 31.6, CH$_2$ | 31.9, CH$_2$ |

TABLE 1-continued

Comparison of ¹H and ¹³C NMR Spectra of Natural (Isolated)⁴ and Synthetic Largazole (1).

| C/H no. | Natural | Synthetic | Natural | Synthetic |
|---|---|---|---|---|
| 28 | 1.28 (m 2H) | | 22.6, $CH_2$ | 22.9, $CH_2$ |
| 29 | 0.87 (br t J = 6.9) | 0.87 (br t J = 7.2) | 14.0, $CH_3$ | 14.3, $CH_3$ |

Example 2

Synthesis of Largazole Amide Isostere

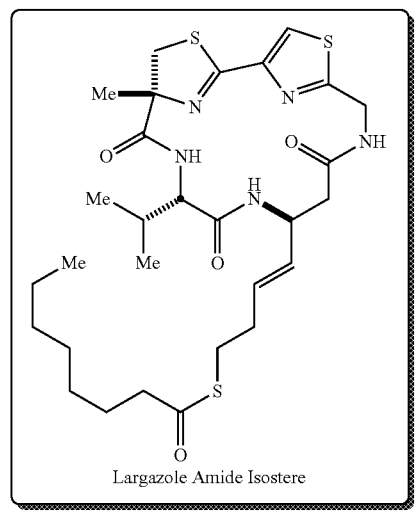

Largazole Amide Isostere

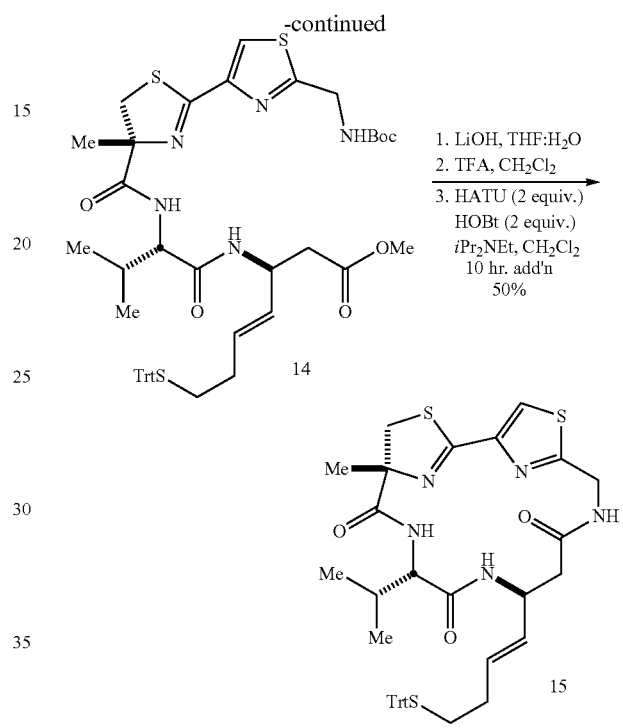

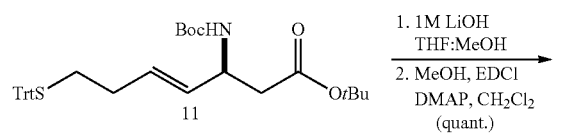

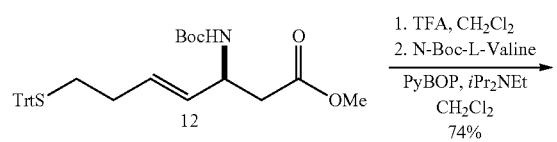

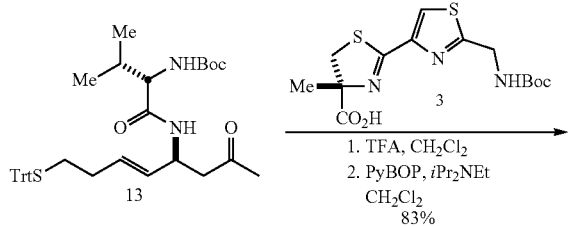

0.400 g (0.77 mmol, 1 equiv.) of β-amino acid 11 was dissolved in 8 mL dry $CH_2Cl_2$ and 0.890 g (4.63 mmol, 6 equiv.) EDCI and 0.019 g (0.15 mmol, 0.2 equiv.) DMAP were added, followed by 0.3 mL (7.7 mmol, 10 equiv.) $CH_3OH$. The resulting solution was stirred under argon for ~12 hrs, when TLC showed complete consumption of the starting material. The solvent was evaporated and the crude reaction mixture submitted immediately to column chromatography. 0.410 g (0.77 mmol, 100% yield) of the product ester eluted cleanly in 1:1 hexanes:EtOAc.

0.164 g (0.31 mmol, 1 equiv.) of β-amino ester 12 was dissolved in 10 mL dry $CH_2Cl_2$ at 0° C. and treated with ~1 mL TFA. The resulting solution was warmed to room temperature and stirred for 2 hrs. The solvents were removed in vaccuo. The crude salt was then dissolved in toluene, concentrated, and dried on mechanical pump to remove residual TFA. Meanwhile, 0.134 g (0.62 mmol, 2 equiv.) N-Boc-L-valine was dissolved in ~10 mL dry $CH_2Cl_2$ and treated with 0.321 g (0.62 mmol, 2 equiv.) PyBOP and 0.160 mL (0.92 mmol, 3 equiv.) iPr₂NEt. The resulting solution was stirred under argon for ~5 min. and then cooled to 0° C. The crude TFA-salt was taken up in 5 mL dry $CH_2Cl_2$ and added dropwise to the activated acid. The mixture was warmed to room temperature and stirred for 2 hrs, when the reaction was assumed complete. The solvents were removed in vaccuo and the crude reaction mixture submitted immediately to column chromatography. 0.163 g (0.23 mmol, 74% yield) of peptide 13 eluted in 1:1 hexanes:EtOAc.

0.346 g (0.40 mmol, 83% yield) of amino ester 14 was synthesized from 0.343 g (0.48 mmol) 13, according to the same procedure employed for compound 13 itself. The product ester was purified by column chromatography, eluting in 1:2 hexanes:EtOAc.

0.094 g (0.11 mmol, 1.0 equiv.) methyl ester 14 was dissolved in 2 mL THF and 1 mL water and treated with 0.005 g (0.21 mmo, ~2.0 equiv.) LiOH. The reaction was stirred for ~0.5 hr., when TLC showed complete consumption of the starting material. The reaction mixture was cooled to 0° C. and acidified to pH ~3-4 by dropwise addition of 1N HCl. The solution was diluted up with water and extracted with $CH_2Cl_2$. The organic layer was dried with $Na_2SO_4$, filtered, and concentrated to provide the free acid, which was used without further purification. The acid was dissolved in 5 mL (to ~0.03M in substrate) dry $CH_2Cl_2$ at 0° C. and treated with 1 mL (to ~0.3M in substrate) TFA. The mixture was then warmed to room temperature and stirred for 2 hrs. The solvents were removed in vaccuo. The crude salt was then dissolved in toluene, concentrated, and dried on mechanical pump to remove residual TFA. It was then dissolved in 5 mL dry $CH_2Cl_2$ and added dropwise to a solution of 0.122 mL (0.70 mmol, 6.0 equiv.) $iPr_2NEt$ in 10 mL $CH_3CN$ at 0° C. The solution was stirred ~0.5 hr., then taken up in syringe and added via syringe pump over 10 hr. to a solution of 0.088 g (0.23 mmol, 2.0 equiv.) HATU, 0.032 g (0.23 mmol, 2.0 equiv.), and 0.122 mL (0.7 mmol, 6.0 equiv.) $iPr_2NEt$ in 100 mL (to ~0.001M) $CH_3CN$. Upon completion of the addition, the solution was stirred a further 6 hrs, then concentrated and redissolved in ~2 mL $CH_2Cl_2$. Solids were removed by filtration through a cotton plug and the product macrocycle was purified via chromatotron. 0.040 g (0.054 mmol, 50% yield) macrocycle 15 eluted in 10:1 $CH_2Cl_2$:$CH_3OH$. HRMS (ESI): m/z calcd. for $C_{40}H_{43}N_5NaO_3S_3$ $(M+Na)^+$ 760.24257. found 760.24209.

Example 3

Synthesis of Largazole Proline Analogue

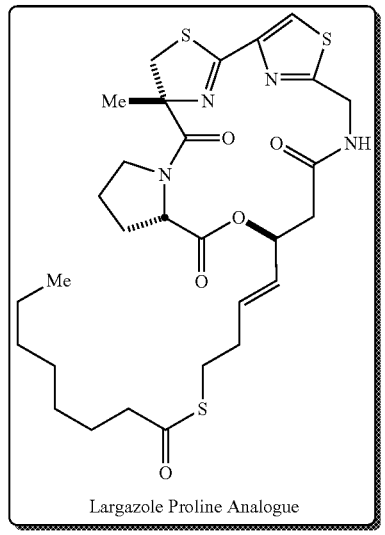
Largazole Proline Analogue

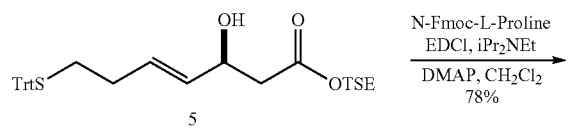

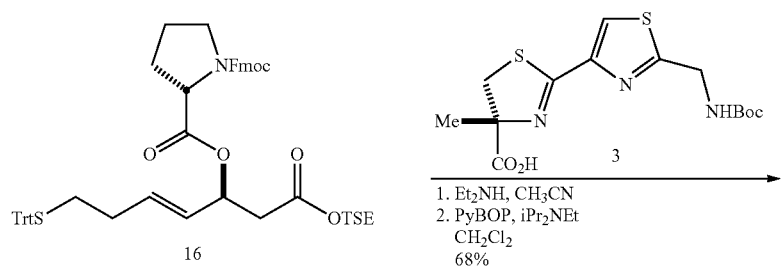

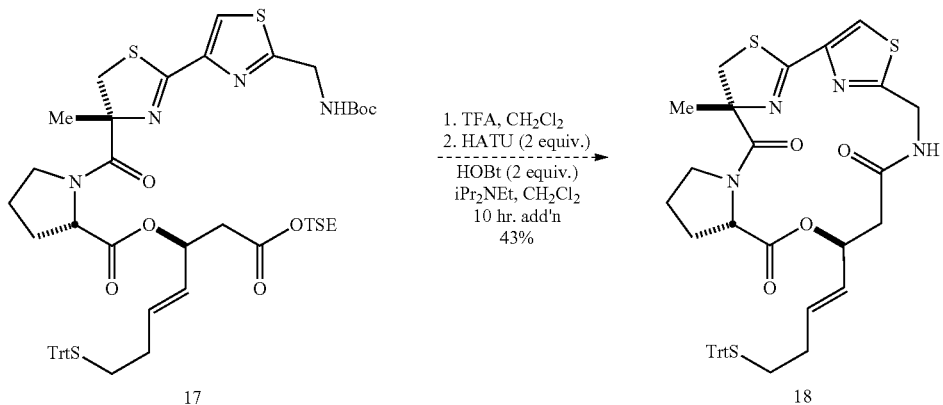

0.185 g (0.36 mmol, 1.0 equiv.) of β-hydroxy ester 5 and 0.601 g (1.8 mmol, 5 equiv.) N-Fmoc-L-proline were dissolved in 10 mL dry $CH_2Cl_2$. The reaction was cooled to 0° C. and 0.341 g (1.8 mmol, 5 equiv.) EDCI and 0.004 g (0.036 mmol, 0.1 equiv.) DMAP were added in ~5 mL $CH_2Cl_2$, followed by 0.370 mL (2.1 mmol, 6 equiv.) $iPr_2NEt$. The reaction was allowed to warm to room temperature and stirred over night, when TLC showed complete disappearance of β-hydroxy ester 5. The reaction was concentrated and submitted immediately to column chromatography. 0.234 g (0.28 mmol, 78% yield) Fmoc-protected diester 16 eluted in 4:1 hexanes:EtOAc.

0.100 g (0.12 mmol, 1.0 equiv.) Fmoc-protected diester 16 was taken up in 12 mL $CH_3CN$ (to ~0.01M) and treated with 0.600 mL diethylamine (to ~0.2M). The resulting solution was stirred for 2 hr. and then concentrated, taken up in EtOAc, reconcentrated, and dried on a mechanical pump to remove residual diethylamine. Meanwhile, 0.046 g (0.13 mmol, 1.1 equiv.) acid 3 was dissolved in 5 mL dry $CH_2Cl_2$ and treated with 0.124 g (0.24 mmol, 2.0 equiv) PyBOP and 0.0.62 mL (0.36 mmol, 3.0 equiv.) $iPr_2NEt$. After stirring for ~5 min., the crude amine in 10 mL $CH_3CN$ was added to the mixture dropwise. After 2 hrs, the reaction was assumed complete, concentrated, and submitted immediately to column chromatography. 0.078 g (0.081 mmol, 68% yield) of acyclic precursor 17 eluted cleanly in 2:1 hexanes:EtOAc. Clear oil. HRMS (ESI): m/z calcd. for $C_{50}H_{62}N_4NaO_7S_3Si$ $(M+Na)^+$ 977.34476. found 977.34522.

0.091 g (0.095 mmol, 1.0 equiv.) acyclic precursor 17 was dissolved in 5 mL (to ~0.03M in substrate) dry $CH_2Cl_2$ at 0° C. and treated with 1 mL (to ~0.3M in substrate) TFA. The mixture was then warmed to room temperature and stirred overnight. The solvents were removed in vaccuo. The crude salt was dissolved in toluene, concentrated, and dried on mechanical pump to remove residual TFA. It was then dissolved in 5 mL dry $CH_2Cl_2$ and added dropwise to a solution of 0.100 mL (0.57 mmol, 6.0 equiv.) $iPr_2NEt$ in 10 mL $CH_3CN$ at 0° C. The solution was stirred ~0.5 hr., then taken up in syringe and added via syringe pump over 10 hr. to a solution of 0.072 g (0.19 mmol, 2.0 equiv.) HATU, 0.026 g (0.19 mmol, 2.0 equiv.), and 0.100 mL (0.57 mmol, 6.0 equiv.) $iPr_2NEt$ in 100 mL (to ~0.001M) $CH_3CN$. Upon completion of the addition, the solution was stirred a further 6 hrs, then concentrated and redissolved in ~2 mL $CH_2Cl_2$. Solids were removed by filtration through a cotton plug and the product macrocycle was purified via chromatotron. 0.030 g (0.041 mmol, 43% yield) macrocycle 18 eluted in 30:1 $CH_2Cl_2$:$CH_3OH$.

Example 4

Synthesis of Largazole Metathesis Substrate

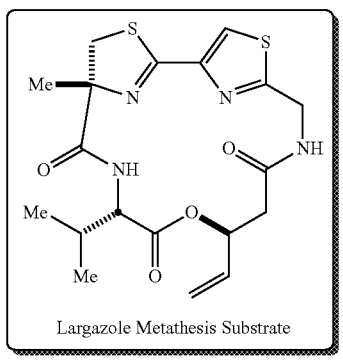

Largazole Metathesis Substrate

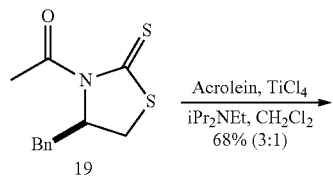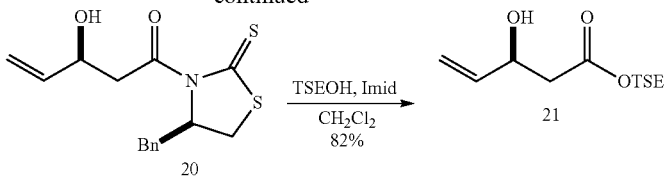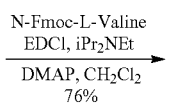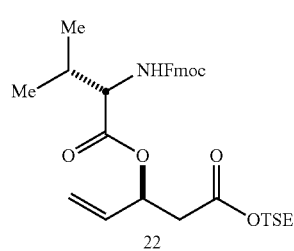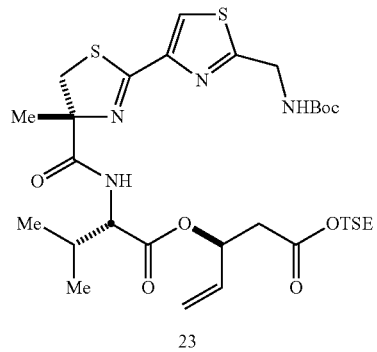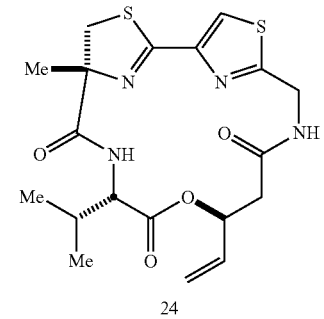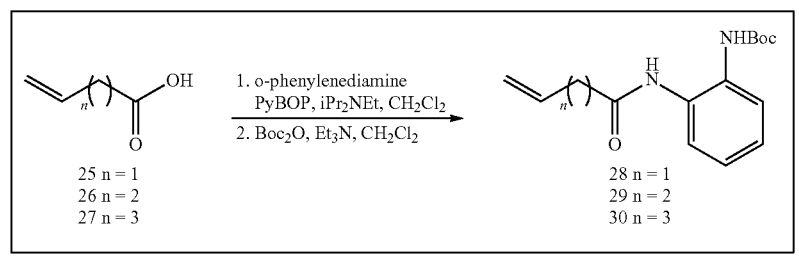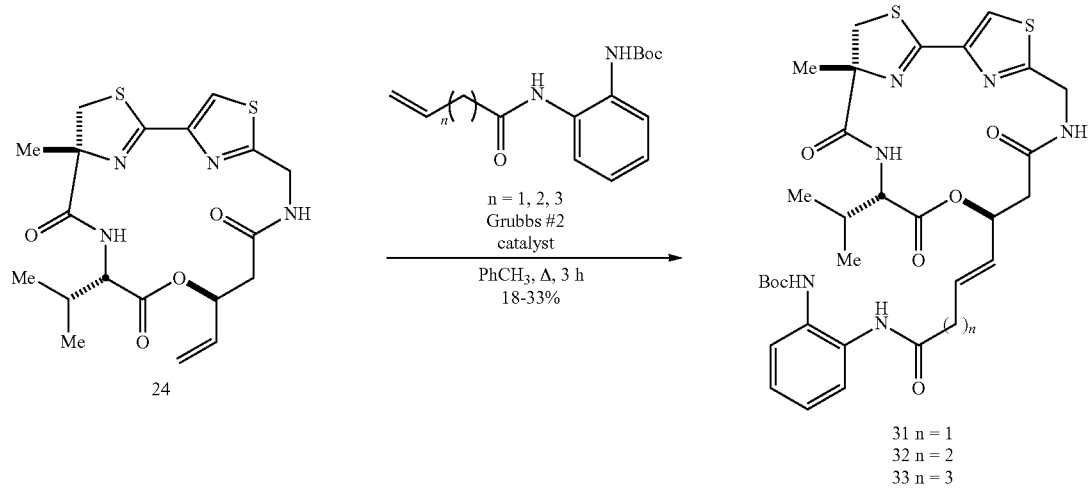

0.520 g (1.7 mmol) thiazoline-thione 20 (Yurek-George, A., et al. 2004 *J Am Chem Soc* 126:1030-1031) was dissolved in 5 mL CH$_2$Cl$_2$ and 2.42 mL (16.9 mmol, 10.0 equiv.) 2-trimethylsilyethanol was added, followed by 0.173 g (2.5 mmol, 1.5 equiv.) imidazole. The resulting solution was stirred overnight, when TLC revealed complete disappearance of the starting material. The reaction mixture was concentrated in vaccuo and submitted immediately to column chromatography (elutes 4:1 hexanes:ethyl acetate), which provided 0.300 g (1.4 mmol, 82% yield) of the protected ester, (3S)-3-Hydroxy-4-pentenoic acid (2-trimethylsilyl)ethyl ester (21), as a clear oil.

0.570 g (1.06 mmol, 76% yield) of diester 22 was synthesized from 0.300 g (1.39 mmol) 21, according to the same procedure employed for compound 6 above. The product diester was purified by column chromatography, eluting in 4:1 hexanes:EtOAc.

0.600 g (0.92 mmol, 85% yield) of acyclic precursor 23 was synthesized from 0.580 g (1.08 mmol) diester 22, according to the same procedure employed for compound 17 above. The product diester was purified by column chromatography, eluting in 2:1 hexanes:EtOAc.

0.308 g (0.47 mmol, 1.0 equiv.) Acyclic precursor 23 was dissolved in 15 mL CH$_2$Cl$_2$ (to ~0.03M), cooled to 0° C. and treated with 5 mL TFA (to ~0.6M). The reaction was allowed to warm to room temperature and stirred overnight. Solvents were evaporated and the crude amino acid redissolved in toluene and concentrated a second time to remove residual TFA. The crude amino acid was then taken up in ~5 mL CH$_2$Cl$_2$ and added dropwise to a stirred solution of 0.491 mL (2.8 mmol, 6.0 equiv.) iPr$_2$NEt in 500 mL dry CH$_3$CN (to ~0.001M). The resulting moderately opaque solution was allowed to stir ~10 min, before 0.358 g (0.94 mmol, 2 equiv.) HATU and 0.127 g (0.94 mmol, 2 equiv.) HOBt were added dropwise in ~5 mL CH$_3$CN. The reaction was allowed to stir for 16 hrs, then concentrated and submitted immediately to column chromatography. Macrocycle 24 (0.131 g, 0.30 mmol, 64% yield) eluted in 10:10:1 hexanes:EtOAc:CH$_3$OH. Clear oil.

For the cross-metathesis reaction, macrocycle 24 was dissolved in dry toluene (to ~0.026M) and heated to reflux under argon. Solutions of sacrificial olefin (2.0 equiv., ~0.26M in toluene) and catalyst (0.2 equiv., ~0.052M in toluene) were then added to the reaction. The resulting mixture was stirred at 110° C. for a further 3 hrs, with equivalent portions of olefin (2.0 equiv., ~0.26M in toluene) and catalyst (0.2 equiv., ~0.052M in toluene) being added each hour. After 3 hrs, the reaction mixture was cooled to room temperature and several drops of DMSO were added and the mixture was stirred overnight. Concentration in vaccuo, followed by column chromatography provided the substituted olefins as products.

According to this general procedure, 0.025 g (0.057 mmol) macrocycle 24 was combined with olefin 29 to yield 0.006 g (0.0087 mmol, 15% yield) compound 32, which eluted slowly in 100% EtOAc. Clear oil. HRMS (ESI): m/z calcd. for C$_{33}$H$_{42}$N$_6$NaO$_7$S$_2$ (M+Na)$^+$721.24541. found 721.24526.

According to this general procedure, 0.039 g (0.089 mmol) macrocycle 24 was combined with olefin 30 to yield 0.012 g (0.017 mmol, 20% yield) compound 33, which eluted slowly in 100% EtOAc. Clear oil. HRMS (ESI): m/z calcd. for C$_{34}$H$_{44}$N$_6$NaO$_7$S$_2$ (M+Na)$^+$735.26106. found 735.2609.

Example 5

Synthesis of Largazole Oxazoline-oxazole Analogue

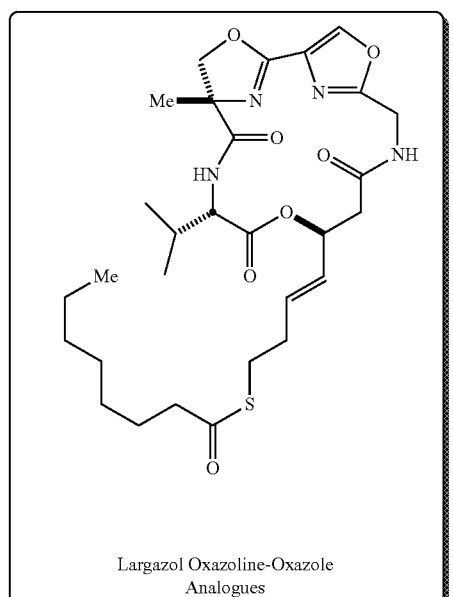

Largazol Oxazoline-Oxazole Analogues

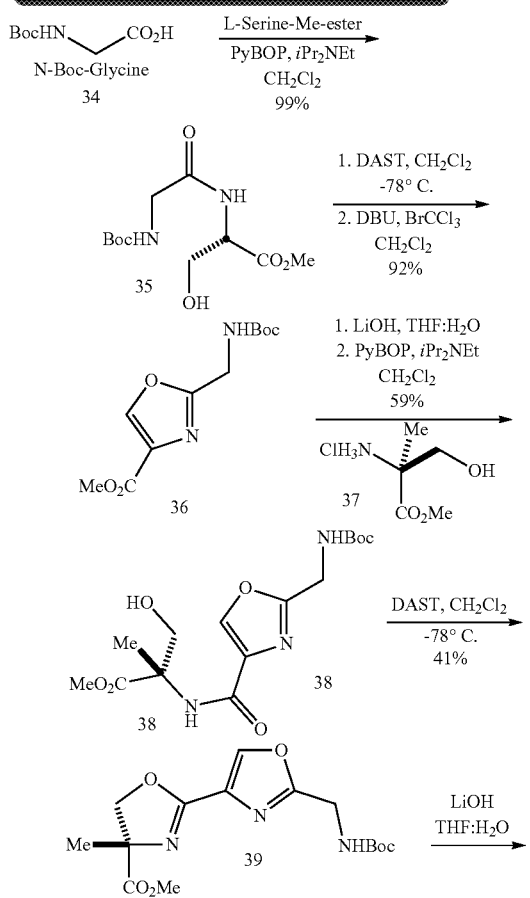

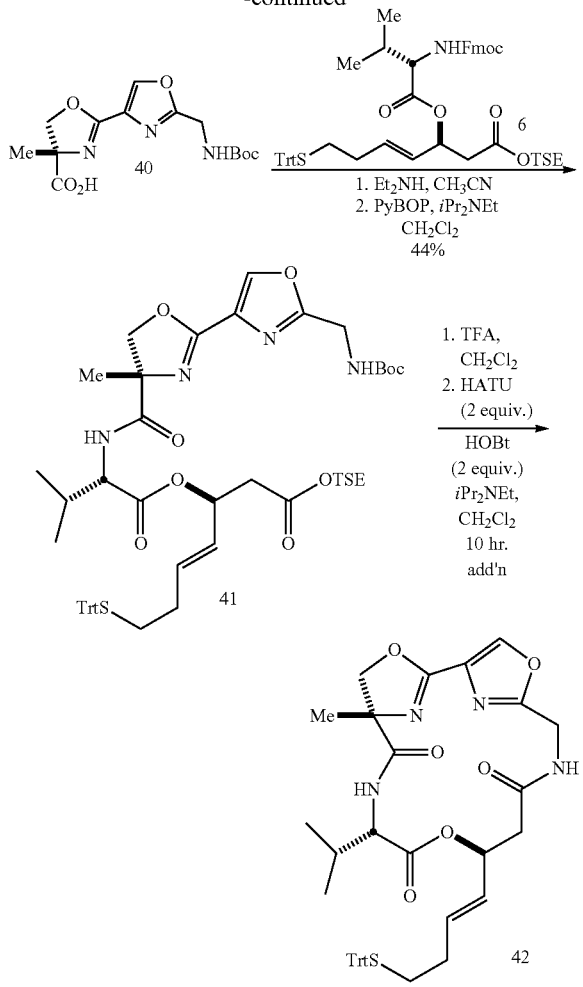

disappearance of the oxazoline in favor of a slightly less polar UV-active compound. The solvents were removed in vaccuo and the product purified by column chromatography. 0.406 g (1.6 mmol, 92% yield) oxazole eluted in 1:1 hexanes:EtOAc.

0.170 g (0.66 mmol, 1.0 equiv.) Oxazole 36 was dissolved in 16 mL THF and 8 mL water and treated with 0.032 g (1.3 mmol, ~2.0 equiv.) LiOH. The reaction was stirred for ~0.5 hrs, when TLC showed complete consumption of the starting material. The reaction mixture was cooled to 0° C. and acidified to pH ~3-4 by dropwise addition of 1N HCl. The solution was diluted up with water and extracted with $CH_2Cl_2$. The organic layer was dried with $Na_2SO_4$, filtered, and concentrated to provide the free acid, which was used without further purification. The acid was dissolved in ~10 mL dry $CH_2Cl_2$ (to ~0.1M) and 0.690 g (1.3 mmol, 2.0 equiv.) PyBOP was added. The reaction and cooled to 0° C. and 0.347 mL (2.0 mmol, 3.0 equiv.) $iPr_2NEt$ was added dropwise. The mixture was allowed to stir for 10 min further at 0° C., when 0.112 g (0.66 mmol, 1.0 equiv.) α-methyl-serine methyl ester hydrochloride salt was added. The reaction was allowed to warm to room temperature and stirred ~2 hrs, when it was assumed complete. Removal of the solvent by rotary evaporator, followed by column chromatography provided 0.140 g (0.39 mmol, 59% yield) alcohol 38 (elutes 100% EtOAc).

0.080 g (0.22 mmol, 1.0 equiv.) Alcohol 38 was dissolved in 5 mL dry $CH_2Cl_2$ (to ~0.3M) under argon and cooled to −78° C. 0.035 mL (0.27 mmol, 1.2 equiv.) DAST in 5 mL $CH_2Cl_2$ was added dropwise to the reaction mixture and it was allowed to stir at −78° C. for ~1.5 hrs, when TLC showed complete disappearance of the starting alcohol. The reaction mixture was poured onto saturated aqueous $NaHCO_3$ at 0° C., stirred and extracted with $CH_2Cl_2$. The organic layer was dried over $Na_2SO_4$, filtered and concentrated. Purification by column chromatography (eluant 100% EtOAc) provided 0.031 g (0.091 mmol, 41% yield) oxazoline-oxazole 39. Clear oil. HRMS (ESI): m/z calcd. for $C_{15}H_{22}N_3O_6$ $(M+H)^+$ 340.15031. found 340.15034.

0.025 g (0.074 mmol, 1.0 equiv.) Oxazole-oxazoline 39 was dissolved in 2 mL THF and 1 mL water and treated with 0.004 g (0.15 mmol, ~2.0 equiv.) LiOH. The reaction was stirred for ~0.5 hr., when TLC showed complete consumption of the starting material. The reaction mixture was cooled to 0° C. and acidified to pH ~3-4 by dropwise addition of 1N HCl. The solution was diluted up with water and extracted with $CH_2Cl_2$. The organic layer was dried with $Na_2SO_4$, filtered, and concentrated to provide the free acid, which was used without further purification. This acid was coupled to 0.068 g (0.081 mmol, 1.0 equiv.) diester 6 according to the same procedure used in preparation of acyclic precursor 41. The product oxazole-oxazoline acyclic precursor was purified by column chromatography. 0.030 g (0.032 mmol, 44% yield) eluted in 1:1 hexanes:EtOAc. White solid. $[\alpha]^{24}_D$: −14.5. (C=1, $CHCl_3$). $^1H$ NMR (300 MHz, $CDCl_3$) δ 9.79 (bs, 1H), 7.98 (s, 1H), 5.59 (s, 1H), 4.59 (d J=6.3 Hz, 2H), 3.88 (d J=11.4 Hz, 1H), 3.30 (d J=11.4 Hz, 1H), 1.66 (s, 3H). $^{13}C$ NMR (75.3 MHz, $CDCl_3$): δ 174.4, 170.3, 169.9, 162.7, 158.0, 145.0, 142.0, 133.9, 130.6, 129.8, 128.1, 128.0, 126.8, 80.6, 75.2, 71.8, 66.8, 63.3, 57.2, 39.9, 38.2, 31.6, 31.3, 31.1, Under argon 1.126 g (6.43 mmol, 1.0 equiv.) N-Boc-glycine was dissolved in ~60 mL dry $CH_2Cl_2$ (to ~0.1M) and 4.01 g (7.7 mmol, 1.2 equiv.) PyBOP was added. The reaction and cooled to 0° C. and 3.36 mL (19.3 mmol, 3 equiv.) $iPr_2NEt$ was added dropwise. The mixture was allowed to stir for 10 min further at 0° C., when 1.00 g (6.43 mmol, 1.0 equiv.) L-serine methyl ester hydrochloride salt was added. The reaction was allowed to warm to room temperature and stirred ~2 hrs, when it was assumed complete. Removal of the solvent by rotary evaporator, followed by column chromatography provided 1.77 g (6.41 mmol, 99% yield) alcohol 35 (elutes 100% EtOAc).

0.476 g (1.7 mmol, 1.0 equiv.) Alcohol 35 was dissolved in 5 mL dry $CH_2Cl_2$ (to ~0.3M) under argon and cooled to −78° C. 0.273 mL (2.07 mmol, 1.2 equiv.) DAST in 5 mL $CH_2Cl_2$ was added dropwise to the reaction mixture, and it was allowed to stir at −78° C. for ~1.5 hrs, when TLC showed complete disappearance of the starting alcohol. The reaction mixture was poured onto saturated aqueous $NaHCO_3$ at 0° C., stirred and extracted with $CH_2Cl_2$. The organic layer was dried over $Na_2SO_4$, filtered and concentrated to give the crude oxazoline. This was then dissolved in 10 mL $CH_2Cl_2$ (to ~0.25M) and 0.850 mL (8.6 mmol, 5.0 equiv.) $BrCCl_3$ and 1.29 mL (8.6 mmol, 5.0 equiv.) DBU were added. The resulting reaction mixture was stirred for 3 hrs, when TLC showed 29.9, 28.5, 26.6, 19.3, 18.1, 17.5, −1.3. HRMS (ESI): m/z calcd. for $C_{50}H_{64}N_4NaO_9SSi$ (M+Na)$^+$ 947.40610. found 947.40756.

Example 6

Synthesis of β-Hydroxy Acid Analogues

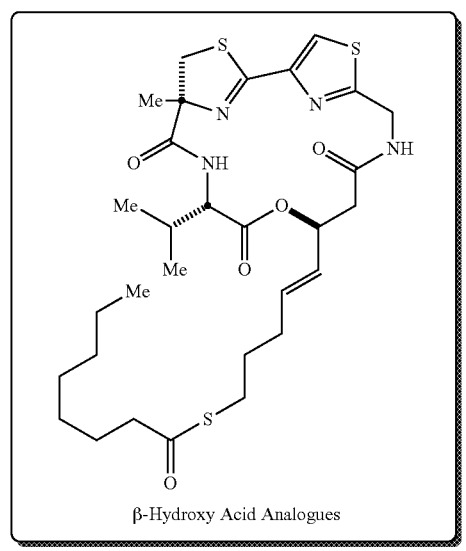
β-Hydroxy Acid Analogues

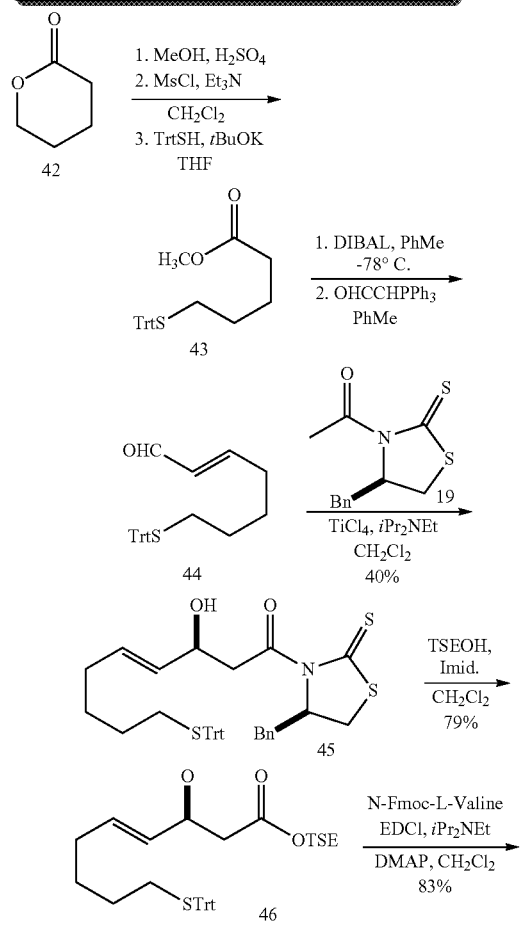

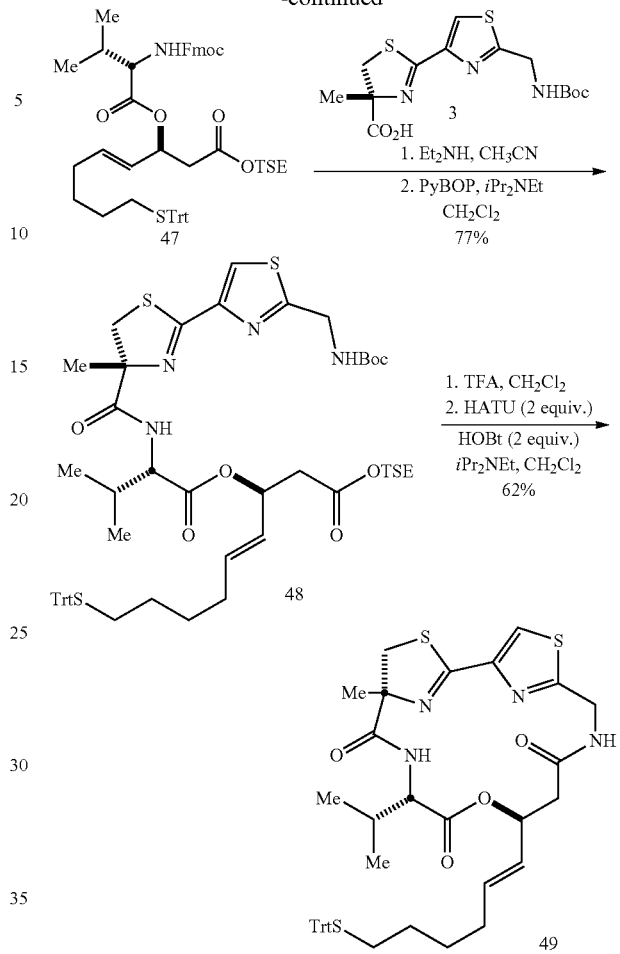

6.4 mL (69.3 mmol, 1.0 equiv.) δ-Valerolactone was added to ~150 mL $CH_3OH$ (to ~0.5M) together with 12 drops of $H_2SO_4$ and the mixture was heated at reflux for 5 hr. The reaction mixture was then cooled to 0° C. and 1.00 g $NaHCO_3$ was added with stirring. The result suspension was placed in the −40° C. freezer for ~2 hrs to precipitate the unconsumed base, which was then filtered off. The solvent was evaporated under water aspirator (bath temp. <35° C.) and dried on a mechanical pump. The crude alcohol, so prepared was dissolved in ~250 mL $CH_2Cl_2$ (to ~0.3M) and 15 mL (104 mmol, 1.5 equiv.) $Et_3N$ and cooled to 0° C. 6.5 mL (83.2 mmol, 1.2 equiv.) Methanesulfonyl chloride was added dropwise. The reaction was then allowed to warm to room temperature and stirred ~2 hrs, when TLC showed complete consumption of the alcohol. The reaction was cooled back to 0° C. and ~50 mL 1N HCl was added. The organic layer was separated, dried over $Na_2SO_4$, filtered, and concentrated to provide the crude mesylate, which was used without further purification.

15.00 g (52 mmol, 1.5 equiv.) Triphenylmethanethiol was dissolved in 100 mL dry THF (to ~0.2M) under argon and 11.66 g (52 mmol, 1.5 equiv.) potassium tert-butoxide was added. The resulting suspension was stirred for ~0.5 hrs and then cooled to 0° C. Approximately half of the crude mesylate was taken up in 10 mL dry THF and added to the thiolate anion dropwise. The reaction mixture was allowed to warm to room temperature and stirred overnight. It was then cooled back to 0° C., and ~15 mL 1N HCl was added. The organic layer was separated and the aqueous layer further extracted with EtOAc. The combined organics were then washed with brine, dried over $Na_2SO_4$, filtered, concentrated, and chromatographed to provide ester 43 (eluent 9:1 hexanes:EtOAc).

1.760 g (4.5 mmol, 1.0 equiv.) Ester 43 was dissolved in 25 mL dry toluene and cooled to −78° C. 6.75 mL (6.8 mmol, 1.0M in toluene, 1.5 equiv.) DIBAL was added via syringe pump over ~0.5 hrs and the reaction was allowed to stir ~1.5 hrs at −78° C. The reaction was then quenched by slow addition of ~5 mL $CH_3OH$ and warmed to room temperature. 25 mL Saturated aqueous sodium potassium tartrate was added and stirred ~5 min. The reaction was diluted with $CH_2Cl_2$ and the organics separated, dried over $Na_2SO_4$, filtered, and concentrated to provide the crude aldehyde, which was carried on without further purification.

The crude aldehyde was dissolved in 25 mL toluene (to ~0.2M), 1.66 g (5.45 mmol, 1.1 equiv.) (triphenylphosphoranylidene)acetaldehyde was added, and the reaction mixture was heated to reflux for 7 hrs. It was then cooled to room temperature, concentrated, chromatographed to provide aldehyde 44 (elutes 4:1 hexanes:EtOAc).

To a stirred solution of 0.243 g (0.97 mmol, 1.2 equiv.) Nagao auxiliary in 10 mL $CH_2Cl_2$ at 0° C. was added 0.115 mL (1.05 mmol, 1.3 equiv.) $TiCl_4$. The reaction mixture was stirred for 5 minutes, cooled to −78° C. before the addition of 0.182 mL (1.05 mmol, 1.3 equiv.) $iPr_2NEt$ and stirred for 2 hours. 0.311 g (0.96 mmol, 1.0 equiv.) Aldehyde 44 in 5 mL $CH_2Cl_2$ was added dropwise and the reaction mixture stirred for 1.5 hrs. 25 mL Saturated $NH_4Cl$ was then added and the reaction mixture diluted with $CH_2Cl_2$ (20 mL), allowed to attain room temperature, extracted with $CH_2Cl_2$ (3×50 mL), washed with brine, and dried over $Na_2SO_4$. The solvent was then removed and the residue purified by flash chromatography (eluant 4:1 hexanes:EtOAc) to give 0.201 g (0.32 mmol, 40% yield) of the major isomer 45 as a yellow oil.

0.200 g (0.31 mmol) thiazoline-thione 45 was dissolved in 5 mL $CH_2Cl_2$ and 0.450 mL (3.1 mmol, 10.0 equiv.) 2-trimethylsilyethanol was added, followed by 0.032 g (0.47 mmol, 1.5 equiv.) imidazole. The resulting solution was stirred overnight, when TLC revealed complete disappearance of the starting material. The reaction mixture was concentrated in vaccuo and submitted immediately to column chromatography (elutes 4:1 hexanes:ethyl acetate), which provided 0.135 g (0.25 mmol, 79% yield) of the protected ester, (3S,4E)-3-Hydroxy-7-[(triphenylmethyl)thio]-4-heptenoic acid (2-trimethylsilyl)ethyl ester (46), as a clear oil.

0.177 g (0.204 mmol, 83% yield) of diester 47 was synthesized from 0.0.135 g (0.247 mmol) 46, according to the same procedure employed for compound 16 above. The product diester was purified by column chromatography, eluting in 4:1 hexanes:EtOAc.

0.155 g (0.157 mmol, 77% yield) of acyclic precursor 48 was synthesized from 0.177 g (0.204 mmol) diester 47, according to the same procedure employed for compound 17 above. The product diester was purified by column chromatography, eluting in 2:1 hexanes:EtOAc.

0.010 g (0.013 mmol, 62% yield) of macrocycle 49 was synthesized from 0.021 g (0.021 mmol) acyclic precursor 48, according to the same cyclization procedure employed for compound 10 above. The product macrocycle was purified by column chromatography, eluting in 100% EtOAc.

Example 7

Biochemical Activity of Synthetic Largazole and Largazole Thiol

The biochemical activity of synthetic largazole (1) and the largazole thiol (2) against HDACs 1, 2, 3 and 6 was investigated employing robust, kinetic biochemical assays. To measure the inhibitory effect on deacetylase function in vitro, a continuous kinetic biochemical assay miniaturized to 384-well plate format was optimized. In this assay, purified, full-length HDAC protein (HDAC1 1.67 ng/μL, HDAC2 0.067 ng/μL, HDAC3/NCor2 0.033 ng/μL, HDAC6 0.67 ng/μL; BPS Biosciences) was incubated with a commercially available fluorophore-conjugated substrate at a concentration equivalent to the substrate $K_m$ (Upstate 17-372; 6 μM for HDAC1, 3 μM for HDAC2, 6 μM for HDAC3/NCoR2 and 20 μM for HDAC6).

Figure 1B:
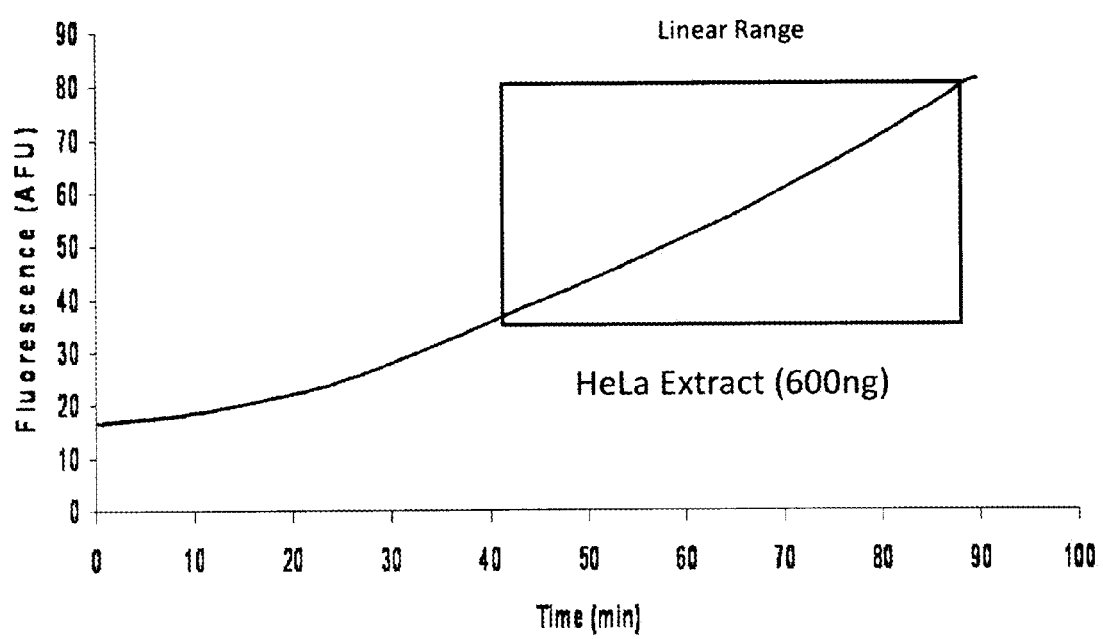
FIG. 1B graphically provides linear data captured after a pre-incubation phase (5-30 minutes) providing a kinetic assessment of deacetylase activity.

Reactions were performed in assay buffer (mM HEPES, 100 mM KCl, 0.001% Tween-20, 0.05% BSA, 200 μM Tris (2-Carboxyethyl)-Phosphine Hydrochloride, pH 7.4) and followed for fluorogenic release of 7-amino-4-methylcoumarin from substrate upon deacetylase and trypsin enzymatic activity (FIG. 1). Fluorescence measurements were obtained in real-time on a Varioskan microtiter plate reader (Thermo). Triplicate experimental data from incubations with inhibitor were normalized to solvent-only wells and analyzed by logistic regression (Spotfire DecisionSite). Calculation of K, was determined using a derivation of the standard formula $K_i = [inhibitor]/(1+S/K_m))-[substrate]/K_m)^{-1}$.

Figure 2:
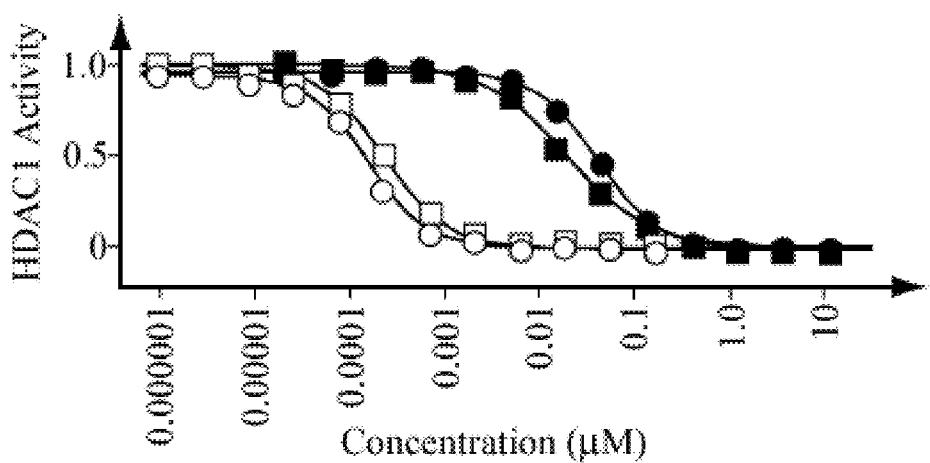
FIG. 2 graphically depicts the inhibition of HDAC1 by largazole (filled circles), largazole thiol (open circles), SAHA (filled squares), and FK228 (open squares).

As presented in FIGS. 2, 3, and Table 2, below, largazole thiol is an extraordinarily potent inhibitor of HDAC1 and HDAC2 ($K_i$=70 μM). The table indicates the HDAC inhibitory activity (Ki; nM) of largazole (1) and largazole thiol (2), as compared to pharmaceutical HDAC inhibitors.

TABLE 2

| Compound | HDAC1 | HDAC2 | HDAC3 | HDAC6 |
|---|---|---|---|---|
| largazole (1) | 20 | 21 | 48 | >1000 |
| largazole thiol (2) | 0.07 | 0.07 | 0.17 | 25 |
| FK228[a] | 0.12 | 0.14 | 0.28 | 35 |
| SAHA | 10 | 10 | 15 | 9 |

[a]The FK228 sample used in this study was synthesized12a and then purified by PTLC to homogeneity.

The parent natural product largazole itself, on the other hand, is a comparatively weak HDAC inhibitor, with potency approximating the non-selective pharmaceutical product SAHA (Vorinostat; Merck Research Laboratories). In fact, the measurement of potency obtained in these studies of largazole define the maximal possible HDAC inhibitory effect. That is, even a trace contamination of largazole thiol or free thiol liberated under aqueous assay conditions or by trypsin (present in this enzyme-coupled reaction) could account for the substantial decrease in enzyme potency observed.

Detailed studies of FK228 isoform selectivity previously identified a strong bias favoring the Class I enzymes, HDAC1, HDAC2 and HDAC3, over the Class IIb enzyme, HDAC6.[12b] Similarly, the active depsipeptide largazole thiol (2) exhibits substantial potency against HDAC1, HDAC2 and HDAC3 in the picomolar range (Table 2, above). Indeed, this degree of inhibitory potency against HDAC1, HDAC2 and HDAC3 is unprecedented. Only FK228 itself has HDACi potency approaching that of 2.

The biochemical data provided herein reflect activity in highly robust, miniaturized homogeneous assays with Z' calculations compatible with high-throughput screening. In this assay, high concordance with published, kinetic measurements of enzyme inhibition (Ki) was observed. Thus, the accuracy of the instant HDAC inhibitory data would be expected to be markedly improved. This is important due to the recorded observation of the unusual, likely unprecedented potency of largazole thiol for HDAC 1 and the direct comparison provided to FK228. Of note, the present synthesis is significantly higher yielding than that previously reported[1(b)].

Example 8

Biochemical Activity of Largazole Thiol Compared to FK228

Figure 3:
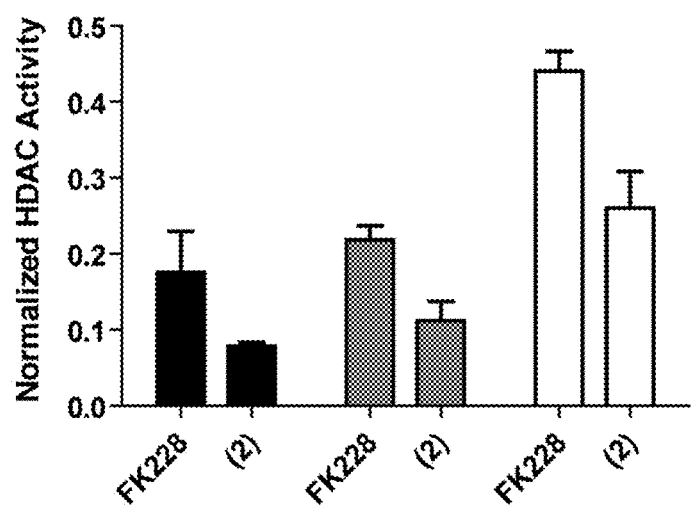
FIG. 3 depicts, in bar graph form, the results of dose-ranging studies of FK228, largazole, and largazole thiol performed against Class I HDAC proteins. As a comparative measure of potency, compounds were studied in triplicate at a standard concentration (0.6 nM). Average data are presented for inhibition of HDAC1 (black), HDAC2 (gray), and HDAC3/NCoR2 (white). Error bars reflect one standard deviation from the mean.

Comparative profiling of FK228 and the largazole thiol (2) demonstrated superior inhibitory potency of the thiol derivative against HDAC1, HDAC2 and HDAC3 (FIG. 3). The comparatively diminished potency of largazole itself in these homogeneous assays indicated pro-drug activation of largazole.

Example 9

Investigation of Antiproliferative Effects of Largazole and Largazole Thiol

Studies aimed at determining the potential utility of largazole as an HDAC inhibitor-based therapeutic agent have been initiated, including studies to determine the antineoplastic effects of largazole (1) and the largazole thiol (2) on cultured human cancer cells. Predicting a potent anti-proliferative effect of largazole based on the biochemical potency for Class I HDACs as described above, a panel of malignant melanoma cell lines was selected for study, due to the typically extreme chemoresistance of this tumor. Effects on cell viability were evaluated using a panel of human malignant melanoma cell lines, using the standard, surrogate measurement of ATP content (Cell TiterGlo; Promega) in 384-well plate format. Replicate measurements were normalized to vehicle-only controls and $IC_{50}$ calculations were performed by logistic regression (Spotfire DecisionSite).

Figure 4:
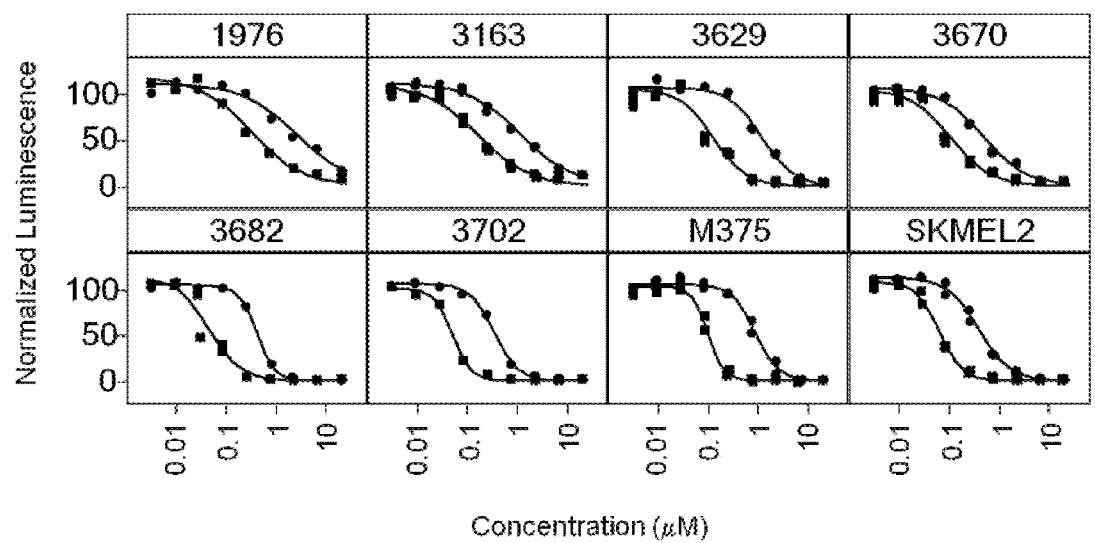
FIG. 4 graphically depicts the effects on cell viability evaluated using a panel of human malignant melanoma cell lines, using the standard, surrogate measurement of ATP content (Cell TiterGlo; Promega) in 384-well plate format. Replicate measurements were normalized to vehicle-only controls, and $IC_{50}$ calculations were performed by logistic regression (Spotfire DecisionSite). Shaded circles depict the antiproliferative effects of largazole thiol, and shaded squares depict the antiproliferative effects of largazole.

As demonstrated in FIG. 4, largazole exhibited sub-micromolar inhibitory effect on melanoma cell proliferation. Of note, largazole has a consistent, superior potency ($IC_{50}$ 45 nM-315 nM) compared to largazole thiol ($IC_{50}$ 360 nM-2600 nM).

Example 10

HDAC Inhibition of Largazole Analogs

A biochemical study of HDAC2 inhibition was carried out using the trypsin-coupled, kinetic fluorescence homogeneous assay described above. Compounds of the invention were assayed in comparison with known standards such as SAHA and a trypsin inhibitor.

TABLE 3

Results from scatter plots depicting activity versus concentration of various compounds.
Conc (uM)

| CompoundName- | CompoundName- | CompoundName- | CompoundName- |
| --- | --- | --- | --- |
| Leupeptin | ab6_113b Largazole | ab6_125 Pyrioyl Disulfide of depsipeptide | ab6_162afr1 n + 2 thiol |
| R2 = 0.9912 | R2 = 0.9617 | R2 = 0.9905 | R2 = 0.9884 |
| min = −25 | min = −2.21E4 | min = 108.2 | min = −240.1 |
| max = 9169 | max = 9652 | max = 9761 | max = 9258 |
| Hill = −1.205 | Hill = −1.165 | Hill = −1.887 | Hill = −1.035 |
| X50 = 0.3077 | X50 = 7.136 | X50 = 0.3265 | X50 = 0.07852 |
| CompoundName- | CompoundName- | CompoundName- | CompoundName- |
| SAHA | ab6_1236 acyl amide | ab6_161afr1 Proline thiol | ab6_162b |
| R2 = 0.9926 | Reached max iterations | R2 = 0.9761 | R2 = 0.9404 |
| min = 102.4 | R2 = 0.009834 | min = 340.3 | min = −1720 |
| max = 9012 | min = 9527 | max = 9470 | max = 8721 |
| Hill = −1.115 | max = 4.862E4 | Hill = −1.823 | Hill = −1.241 |
| X50 = 0.02683 | Hill = 0.2128 | X50 = 0.7733 | X50 = 2.689 |
|  | X50 = 1.677E12 |  |  |
| CompoundName- | CompoundName- | CompoundName- | CompoundName- |
| ab6_113a thiol depsipeptide | ab6_123a amide thiol | ab6_161b Proline acyl | none |
| R2 = 0.994 | R2 = 0.995 | Reached max iterations | Not solved. All |
| min = −84.01 | min = 40.61 | R2 = 0.04023 | data points have |
| max = 9677 | max = 9382 | min = 7262 | the same x-value. |
| Hill = −1.55 | Hill = −1.09 | max = 9299 |  |
| X50 = 0.003574 | X50 = 0.01112 | Hill = −0.3774 |  |
|  |  | X50 = 707.6 |  |

Figure 5:
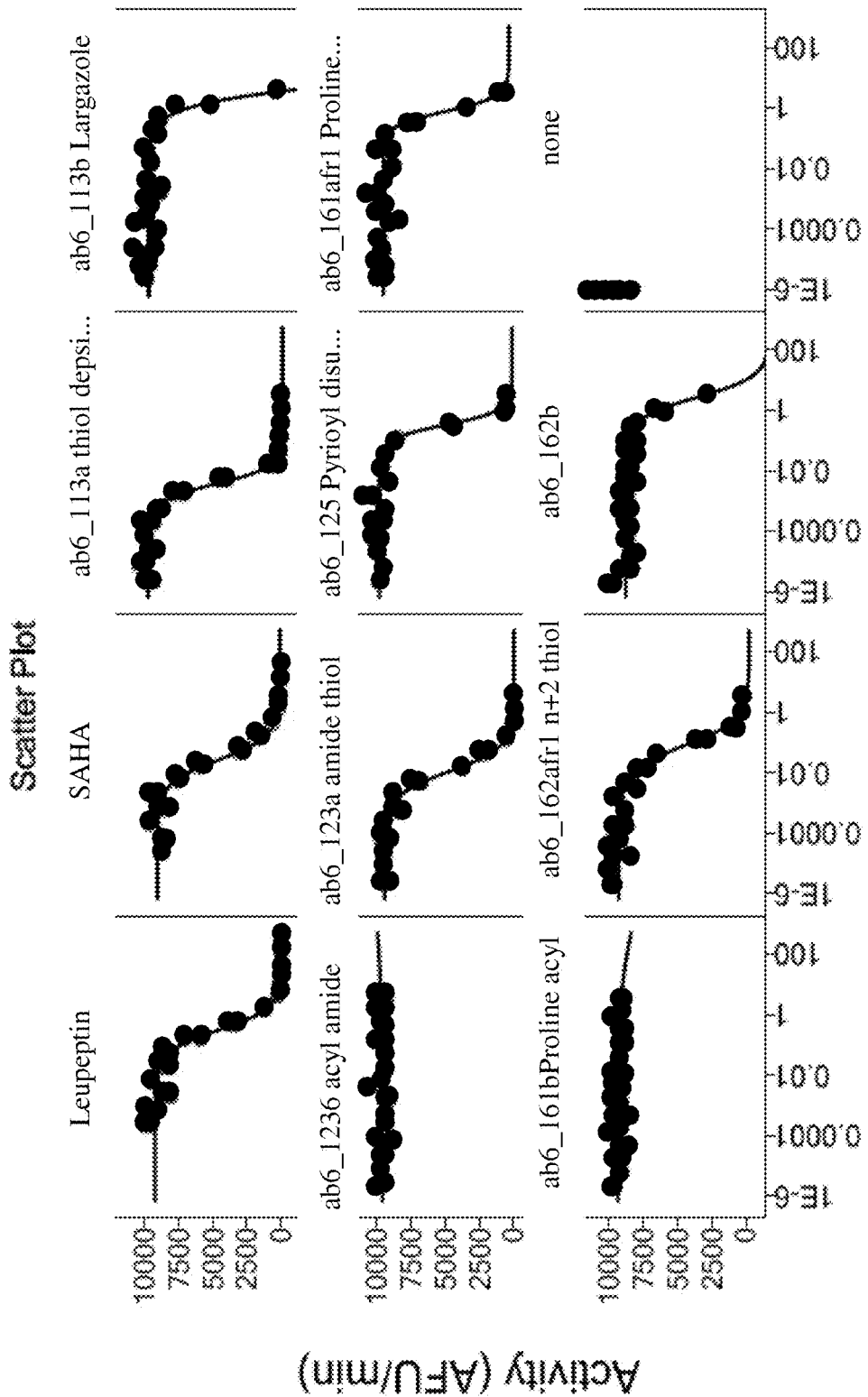
FIG. 5 shows, above, scatter plots depicting HDAC inhibition by various largazole analogs. The curves represent IC50 curves comparing compounds of the invention to standards (SAHA and a trypsin inhibitor).

The chemical structures of the compounds designated numerically in FIG. 5, above, are shown below.
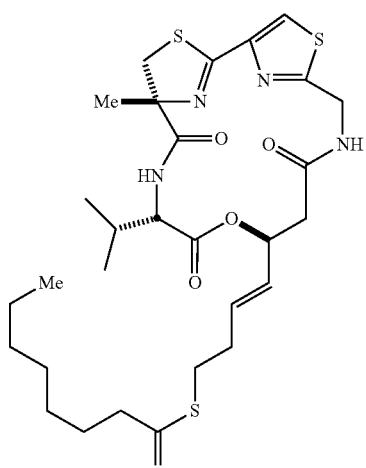
ab6_113b Largazole
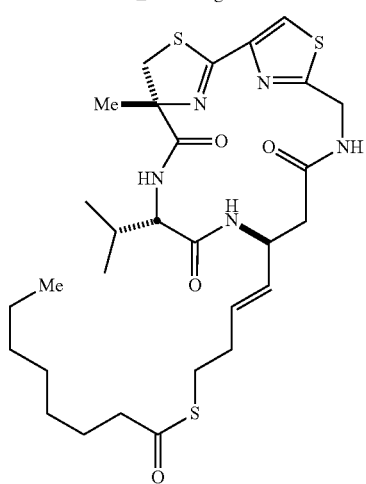
ab6_1236 acyl amide
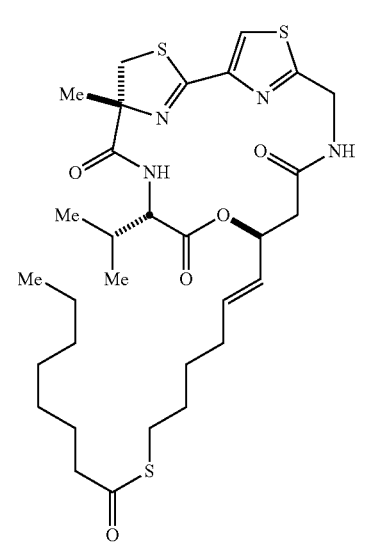
ab6_162b
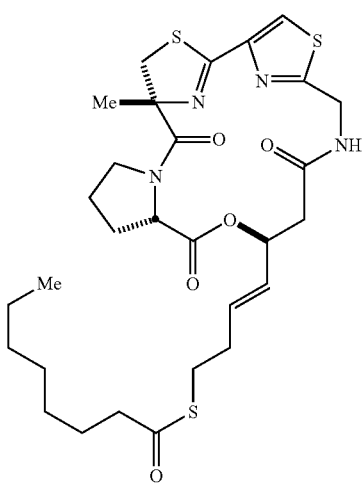
ab6_161b Proline acyl
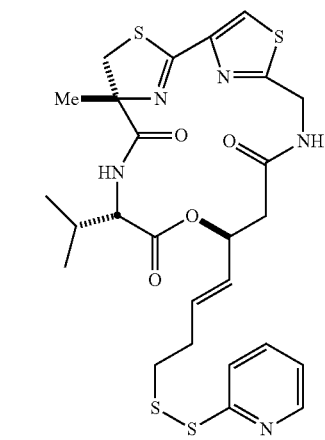
ab6_125 Pyrioyl Disulfide
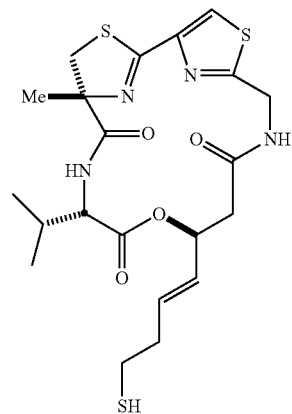
ab6_113a thiol depsipeptide

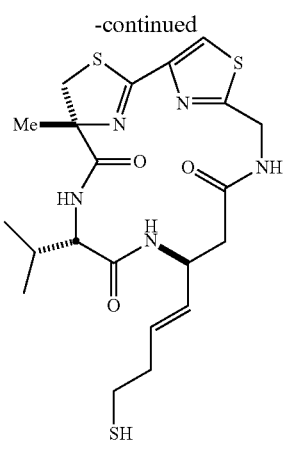

ab6_123a amide thiol

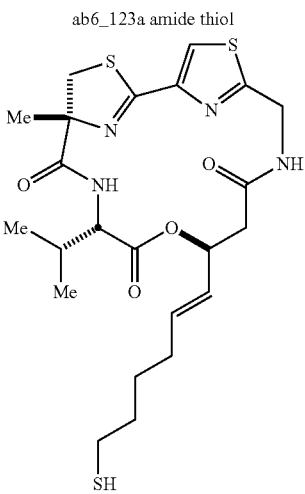

ab6_162afr1 n + 2 thiol

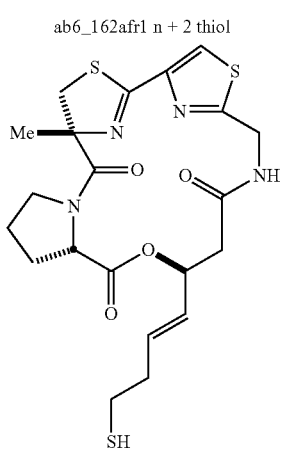

ab6_161afr1 Proline thiol

Thus, described herein thus far is an efficient total synthesis of largazole (1) in eight linear steps and 37% overall yield, and its active metabolite, the largazole thiol (2) in seven linear steps. The synthesis recorded herein provided 12 milligrams of synthetic largazole and 19 milligrams of largazole thiol on the first pass (and should be readily scaleable to gram-quantities), allowing for further investigation of the biological activity of this potential cancer chemotherapeutic.

Further described herein is that largazole is, in fact, a pro-drug, which must be converted to its active form, free-thiol 2. The combination of cap group and zinc-binding motif present in this thiol provide the most potent and selective HDACi reported to date. The octanoyl residue in largazole likely serves a dual role, imparting better cell-permeability and allowing facile presentation of the free thiol within the cell. The observed inverse difference in cytotoxicity can be attributed to the superior cell-permeability of the thioester (1) as compared to the thiol (2). The data presented herein can be used to design and develop potent and therapeutically active agents that target inhibition of HDAC's.

Since FK228, FR901375 and spiruchostatin mask the common and key 3-hydroxy-7-mercaptohept-4-enoic acid unit as a reductively labile disulfide, other protect-and-release strategies for exploiting this potent zinc-binding arm in the context of new molecular scaffolds are contemplated. In addition, the molecular scaffold of largazole provides yet another macrocyclic template from which a myriad of potentially active and isoform-selective HDAC inhibitors can be designed and synthesized.

Example 11

Synthesis of Largazole-Azumamide Hybrid

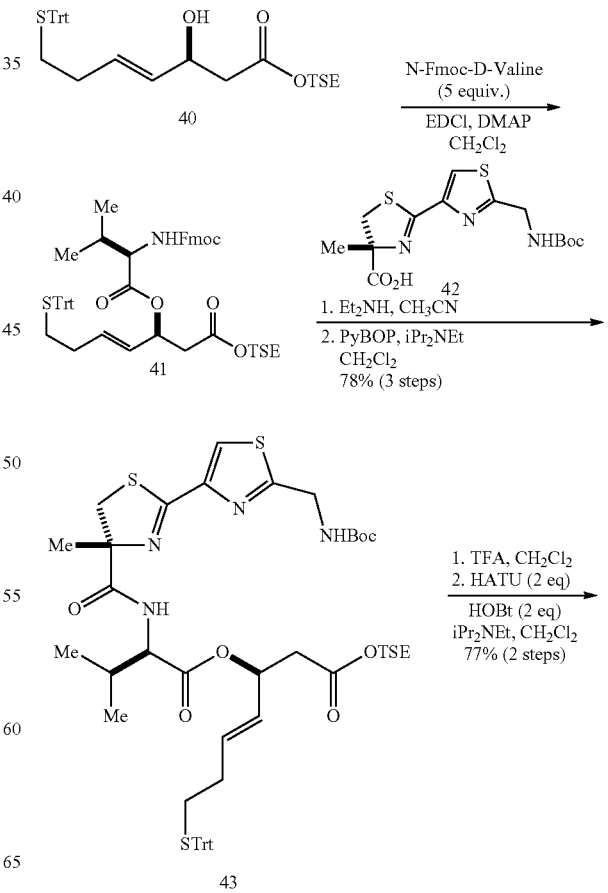

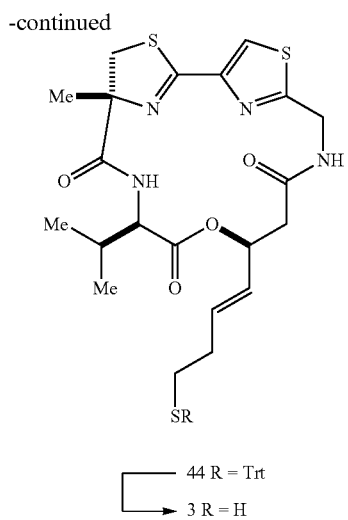

44 R = Trt
3 R = H (3S,4E)-2-(Trimethylsilyl)ethyl-3-[(R)-2-((R)-2-{2-[(tert-butoxycarbonyl)methyl]thiazol-4-yl}-4-methyl-4,5-dihydrothiazole-4-carboxamido)-3-methylbutanoyloxy]-7-(tritylthio)hept-4-enoate (43)

0.104 g (0.2 mmol) of β-hydroxy ester 40 and 0.340 g (1.0 mmol, 5 equiv.) N-Fmoc-D-valine were dissolved in 5 mL dry CH$_2$Cl$_2$. The reaction was cooled to 0° C. and 0.192 g (1.0 mmol, 5 equiv.) EDCI and 0.003 g (0.02 mmol, cat.) DMAP were added in ~5 mL CH$_2$Cl$_2$, followed by 0.2 mL iPr$_2$NEt. The reaction was allowed to warm to room temperature and stirred over night, when TLC showed complete disappearance of 40. The reaction was concentrated and passed through a short plug of silica, washing with 100% EtOAc. The product diester eluted with a by-product from the excess amino acid used, which was not separated at this time. Instead, the crude diester was taken up in 15 mL CH$_3$CN (to ~0.01M) and treated with 1 mL diethylamine (to ~0.2M). The resulting solution was stirred for two hours and then concentrated, taken up in EtOAc, and concentrated again.

0.061 g (0.22 mmol, 1.1 equiv.) acid 42 was dissolved in 5 mL dry CH$_2$Cl$_2$ and treated with 0.151 g (0.44 mmol, 2.0 equiv) PyBOP and 0.076 mL (0.66 mmol, 3.0 equiv.) iPr$_2$NEt. After stirring for ~5 min., the crude amine in 5 mL CH$_2$Cl$_2$ was added to the mixture dropwise. After 2 hrs, the reaction was concentrated and submitted immediately to column chromatography, 0.056 g (0.058 mmol, 30% from 40) of peptide 43 eluting cleanly in (2:1 hexanes:EtOAc). Clear oil. [α]$^{24}_D$: −6.0 (c=1, CHCl$_3$). $^1$H NMR (300 MHz, CDCl$_3$) δ 0.02 (s, 9H), 0.88 (d J=6.9 Hz, 3H), 0.95 (d J=6.9 Hz, 3H), 1.32-1.38 (m, 2H), 1.47 (s, 9H), 1.59 (s, 3H), 1.96-2.05 (m, 2H), 2.12-2.21 (m, 3H), 2.45 (dd J=5.1, 15.9 Hz, 1H), 2.59 (dd J=8.4, 15.9 Hz, 1H), 3.29 (d J=11.4 Hz, 1H), 3.73 (d J=11.4 Hz, 1H), 4.05-4.17 (m, 2H), 4.52 (dd J=4.5, 9.0 Hz, 1H), 4.63 (d J=6.3 Hz, 1H), 5.26-5.35 (m, 2H), 5.54-5.61 (m, 2H), 7.18-7.39 (m, 16H), 7.93 (s, 1H). $^{13}$C NMR (75.5 MHz, CDCl$_3$): δ −1.3, 11.3, 12.0, 17.5, 17.6, 18.8, 19.2, 19.3, 25.4, 28.5, 29.9, 31.2, 31.5, 31.7, 39.8, 41.2, 42.1, 42.5, 53.7, 57.0, 63.3, 66.8, 71.8, 80.6, 85.3, 121.9, 126.8, 127.8, 128.0, 129.7, 133.4, 145.0, 148.8, 155.8, 163.5, 169.9, 170.5, 174.7. HRMS (ESI): m/z calcd. for C$_{50}$H$_{64}$N$_4$NaO$_7$S$_3$Si (M+Na)$^+$ 979.35986. found 979.35980.

General Procedure for Macrocyclization 0.056 g (0.058 mmol) Acyclic precursor 43 was dissolved in 5 mL CH$_2$Cl$_2$ (to ~0.03M), cooled to 0° C. and treated with 1 mL TFA (to ~0.6M). The reaction was allowed to warm to room temperature and stirred overnight. Solvents were evaporated and the crude amino acid redissolved in toluene and concentrated a second time to remove residual TFA. The crude amino acid was then taken up in ~5 mL CH$_2$Cl$_2$ and added dropwise to a stirred solution of 0.061 mL (6.0 equiv.) iPr$_2$Net in 60 mL dry CH$_3$CN (to ~0.001M). The resulting moderately opaque solution was allowed to stir ~10 min., before 0.044 g (0.12 mmol, 2 equiv.) HATU and 0.016 g (0.12 mmol, 2 equiv.) HOBt were added dropwise in ~5 mL CH$_3$CN. The reaction was allowed to stir for 16 hr., then concentrated and submitted immediately to column chromatography. Macrocycle 44 (0.020 g, 57% yield) eluted quickly in EtOAc, after a general wash with 10:1 hexanes:EtOAc. Clear oil. [α]$^{24}_D$: +16.1 (c=1, CH$_3$OH). $^1$H NMR (300 MHz, 5:1 CDCl$_3$:CD$_3$OD) δ 0.70 (d J=6.6 Hz, 3H), 0.80 (d J=6.6 Hz, 3H), 1.71 (s, 3H), 1.90-2.03 (m, 3H), 2.05-2.12 (m, 2H), 2.41 (d J=16.8 Hz, 1H), 2.80 (dd J=10.5, 16.8 Hz, 1H), 3.14 (d J=11.4 Hz, 1H), 4.08-4.19 (m, 3H), 4.90 (d J=17.1 Hz, 1H), 5.21 (dd J=8.4, 15.3 Hz, 1H), 5.57-5.71 (m, 2H), 7.09-7.22 (m, 10H), 7.28-7.32 (m, 6H), 7.67 (s, 1H). $^{13}$C NMR (100.6 MHz, 5:1 CDCl$_3$:CD$_3$OD): δ 18.0, 18.8, 26.4, 31.0, 31.4, 32.2, 38.7, 39.9, 40.7, 41.5, 59.8, 59.9, 66.8, 73.0, 77.5, 84.6, 125.0, 126.8, 127.9, 128.0, 129.7, 135.3, 144.9, 147.1, 163.8, 167.9, 168.5, 170.4, 174.0. HRMS (ESI): m/z calcd. for C$_{40}$H$_{42}$N$_4$NaO$_4$S$_3$ (M+Na)$^+$ 761.22604. found 761.22478.

General Procedure for Trityl Deprotection 0.010 g (0.04 mmol) S-Trityl macrocycle 44 was dissolved in 5 mL dry CH$_2$Cl$_2$ and cooled to 0° C. The mixture was successively treated with 0.017 mL (0.08 mmol, 2 equiv.) iPr$_3$SiH and 0.200 mL TFA (to ~0.2M in 44). The reaction mixture was allowed to warm to room temperature and stirred for 2 hrs, before being concentrated and chromatographed (EtOAc) to provide 0.019 g (0.038 mmol, 95%) thiol 9. Clear oil. [α]$^{24}_D$: +11.0 (c=1, CHCl$_3$). $^1$H NMR (300 MHz, CDCl$_3$) δ 0.89 (d J=6.9 Hz, 3H), 0.97 (d J=6.9 Hz, 3H), 1.42 (t J=7.8 Hz, 1H), 2.10-2.18 (m, 1H), 2.29-2.40 (m, 2H), 2.53-2.63 (m, 3H), 2.82-2.94 (m, 1H), 3.22 (d J=11.4 Hz, 1H), 4.23-4.35 (m, 3H), 5.10 (dd J=7.8, 16.5 Hz, 1H), 5.45 (dd J=8.7, 15.9 Hz, 1H), 5.82 (t J=9.9 Hz, 1H), 5.90 (dt J=7.8, 15.3 Hz, 1H), 6.43 (s, 1H), 7.25 (s, 1H), 7.72 (s, 1H). $^{13}$C NMR (100.6 MHz, CDCl$_3$): δ 18.3, 19.1, 23.9, 26.7, 32.5, 36.6, 38.8, 40.6, 41.0, 41.9, 59.9, 72.9, 85.0, 124.8, 124.9, 129.1, 134.8, 167.9, 168.1, 169.8, 173.4. HRMS (ESI): m/z calcd. for C$_{21}$H$_{28}$N$_4$NaO$_4$S$_3$ (M+Na)$^+$ 519.11649. found 519.11777.

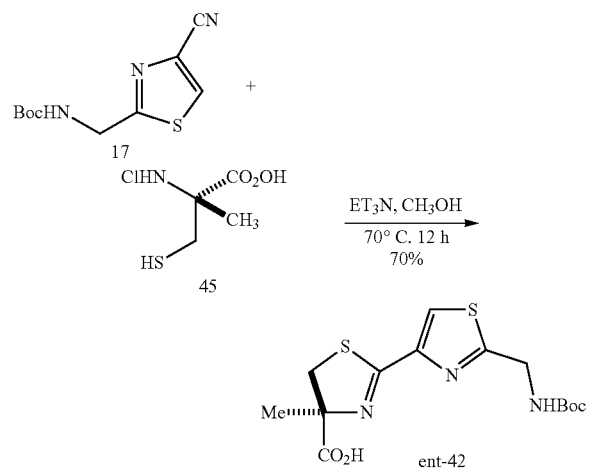

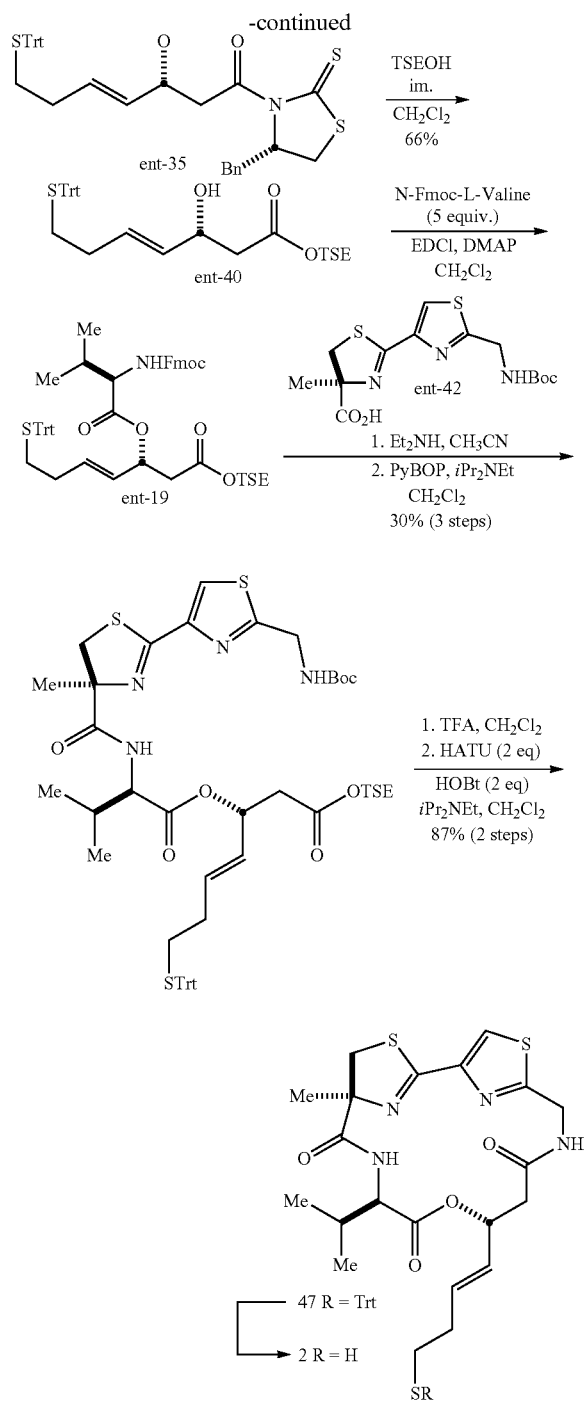

(S)-2-(2-((tert-Butoxycarbonylamino)methyl)thiazol-4-yl)-4-methyl-4,5-dihydrothiazole-4-carboxylic acid (ent-42)

To a solution of sodium bicarbonate (0.65 g, 7.68 mmol) in CH$_3$OH (22 ml) and pH 7 phosphate buffer (14.4 ml) was added 17 and 45. The mixture was stirred overnight at 70° C. and then cooled to room temperature. The solvent was evaporated, and the residue dissolved in ether and water. Following extraction into ether, the organic layers were discarded and the aqueous layer was acidified to pH 2 with 3 N HCl. This was then extracted into EtOAC (3×20 ml), washed with brine, and dried over sodium sulfate to give ent-42 as a light brown foam (0.96 g, 70% yield). [α]$^{24}_D$: +22.0 (c=1, CH$_3$OH). Both $^1$H and $^{13}$C NMR spectra of ent-42 matched previously published spectra of 42 itself.

(R,E)-2-(Trimethylsilyl)ethyl 3-hydroxy-7-(tritylthio)hept-4-enoate (ent-40)

To a stirred solution of ent-35 (0.88 g, 1.44 mmol) in CH$_2$Cl$_2$ (14 ml) was added 2-(trimethylsilyl)ethanol (2 ml, 14.4 mmol) and imidazole (0.15 g, 2.16 mmol). The mixture was stirred overnight, after which the solvent was evaporated and the residue purified by column chromatography (10:1 to 4:1 hexanes/ethyl acetate) to give ent-40 as a clear oil (0.49 g, 66%). [α]$^{24}_D$: +5.0 (c=2, CHCl$_3$). Both $^1$H and $^{13}$C NMR spectra of ent-40 matched previously published spectra of 40 itself.

(3R,4E)-2-(Trimethylsilyl)ethyl-3-[(S)-2-((S)-2-{2-[(tert-butoxycarbonyl)methyl]thiazol-4-yl}-4-methyl-4,5-dihydrothiazole-4-carboxamido)-3-methylbutanoyloxy]-7-(tritylthio)hept-4-enoate (46)

46 was prepared from ent-40 (0.14 g, 0.28 mmol) in the same fashion as 43, to give 46 in 50% yield (0.12 g, 0.14 mmol). [α]$^{24}_D$: +20.0, (c=0.2, CHCl$_3$. Both $^1$H and $^{13}$C NMR spectra of 43 matched previously published spectra of ent-43.

(−)-Largazole thiol (2).

The general procedure for both cyclization and deprotection described above was followed to give trityl protected macrocycle 47 in 87% yield (0.07 g, 0.14 mmol), [α]$_D$=−6, c=0.0.1 in methanol. Ent-Largazole (2) was completed in 90% yield (0.03 g, 0.05 mmol), [α]$_D$=−21.0 (c=0.1, CHCl$_3$). $^1$H and $^{13}$C NMR of both 47 and 2 match those of (+)-Largazole.

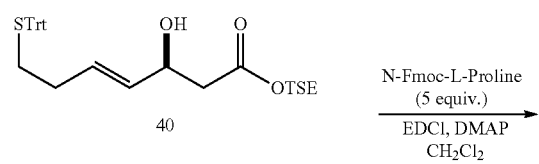

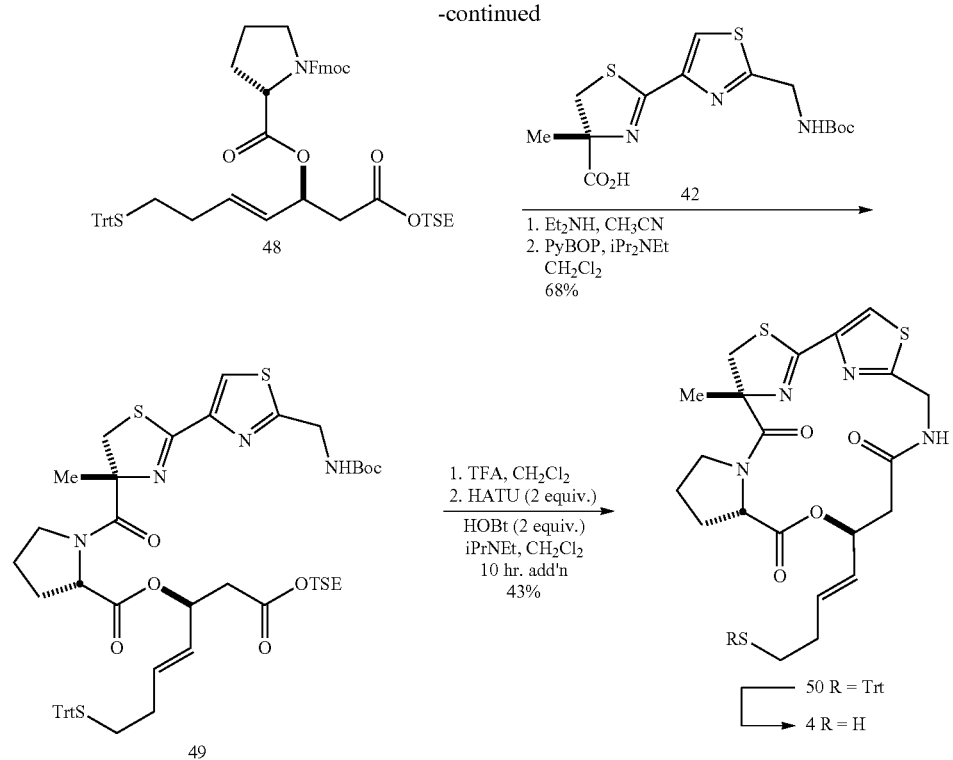

Acyclic Precursor 49.

0.185 g (0.36 mmol, 1.0 equiv.) of β-hydroxy ester 40 and 0.601 g (1.8 mmol, 5 equiv.) N-Fmoc-L-proline were dissolved in 10 mL dry $CH_2Cl_2$. The reaction was cooled to 0° C. and 0.341 g (1.8 mmol, 5 equiv.) EDCI, and 0.004 g (0.036 mmol, 0.1 equiv.) DMAP were added in ~5 mL $CH_2Cl_2$, followed by 0.370 mL (2.1 mmol, 6 equiv.) $iPr_2NEt$. The reaction was allowed to warm to room temperature and stirred overnight, when TLC showed complete disappearance of β-hydroxy ester 40. The reaction was concentrated and submitted immediately to column chromatography. 0.234 g (0.28 mmol, 78% yield) Fmoc-protected diester 48 eluted in 4:1 hexanes:EtOAc.

0.100 g (0.12 mmol, 1.0 equiv.) Fmoc-protected diester 48 was taken up in 12 mL $CH_3CN$ (to ~0.01M) and treated with 0.600 mL diethylamine (to ~0.2M). The resulting solution was stirred for 2 hrs and then concentrated, taken up in EtOAc, reconcentrated, and dried on a mechanical pump to remove residual diethylamine. Meanwhile, 0.046 g (0.13 mmol, 1.1 equiv.) acid 42 was dissolved in 5 mL dry $CH_2Cl_2$ and treated with 0.124 g (0.24 mmol, 2.0 equiv) PyBOP and 0.0.62 mL (0.36 mmol, 3.0 equiv.) $iPr_2NEt$. After stirring for ~5 min., the crude amine in 10 mL $CH_3CN$ was added to the mixture dropwise. After 2 hrs, the reaction was assumed complete, concentrated, and submitted immediately to column chromatography. 0.078 g (0.081 mmol, 68% yield) of acyclic precursor 49 eluted cleanly in 2:1 hexanes:EtOAc. (49): Clear oil. Compound NMRs display highly complex mixtures of conformational isomers; the room temperature $^1$H NMR spectrum (300 MHz, $CDCl_3$) and $^{13}$C NMR spectrum (100.6 MHz, $CDCl_3$), as well as elevated temperature $^1$H NMR spectra (300 MHz, DMSO-$d_6$) not shown. HRMS (ESI): m/z calcd. for $C_{50}H_{62}N_4NaO_7S_3Si$ $(M+Na)^+$ 977.34476. found 977.34522.

S-Trityl macrocycle 50 and thiol 4

0.091 g (0.095 mmol, 1.0 equiv.) acyclic precursor 49 was dissolved in 5 mL (to ~0.03M in substrate) dry $CH_2Cl_2$ at 0° C. and treated with 1 mL (to ~0.3M in substrate) TFA. The mixture was then warmed to room temperature and stirred overnight. The solvents were removed in vacuo. The crude salt was dissolved in toluene, concentrated, and dried on mechanical pump to remove residual TFA. It was then dissolved in 5 mL dry $CH_2Cl_2$ and added dropwise to a solution of 0.100 mL (0.57 mmol, 6.0 equiv.) $iPr_2NEt$ in 10 mL $CH_3CN$ at 0° C. The solution was stirred ~0.5 hrs, then taken up in syringe and added via syringe pump over 10 hrs to a solution of 0.072 g (0.19 mmol, 2.0 equiv.) HATU, 0.026 g (0.19 mmol, 2.0 equiv.), and 0.100 mL (0.57 mmol, 6.0 equiv.) $iPr_2NEt$ in 100 mL (to ~0.001M) $CH_3CN$. Upon completion of the addition, the solution was stirred a further 6 hrs, then concentrated and redissolved in ~2 mL $CH_2Cl_2$. Solids were removed by filtration through a cotton plug, and the product macrocycle was purified via chromatotron. 0.030 g (0.041 mmol, 43% yield) macrocycle 50 eluted in 30:1 $CH_2Cl_2$:$CH_3OH$. (50): $[\alpha]^{24}_D$: +29.1 (c=1, $CHCl_3$). $^1$H NMR (400 MHz, $CDCl_3$) δ 1.43 (s, 3H), 1.56-1.60 (m, 2H), 1.70-1.79 m, 2H), 1.89-1.95 (m, 1H), 2.03-2.19 (m, 4H), 2.26 (d J=17.6 Hz, 1H), 2.56 (dd J=2.8, 14.0 Hz, 1H), 2.81 (dd J=5.2, 14.0 Hz, 1H), 3.51 (dd J=11.6, 16.4 HZ, 1H), 3.52 (d J=11.6 Hz, 1H), 3.76-3.80 (m, 1H), 3.86 (d J=11.6 Hz, 1H), 3.88 (dd J=4.8, 17.7 Hz, 1H), 4.72 (dd J=6.4, 17.6 Hz, 1H), 5.12 (dd J=2.8, 8.4 Hz, 1H), 5.21-5.25 (m, 1H), 5.70 (dt J=6.4, 16.0 Hz, 1H), 5.91 (dd J=5.6, 16.0 Hz, 1H), 7.15-7.23 (m, 10H), 7.59 (s, 1H). $^{13}$C NMR (100.6 MHz, $CDCl_3$): δ 25.7, 31.5, 31.8, 32.5, 41.1, 42.8, 44.9, 49.6, 60.8, 67.0, 73.0, 77.4, 86.9, 124.0, 127.0, 128.1, 128.5, 129.8, 130.6, 130.8, 144.7, 147.9, 158.4, 167.2, 170.1, 172.3, 173.8. HRMS (ESI): m/z calcd. for $C_{40}H_{40}N_4NaO_4S_3$ $(M+Na)^+$759.21039. found 759.21059. 0.009 g 50 was deprotected according to the general procedure to provide 4, which was purified by preparative thin layer chromatography.

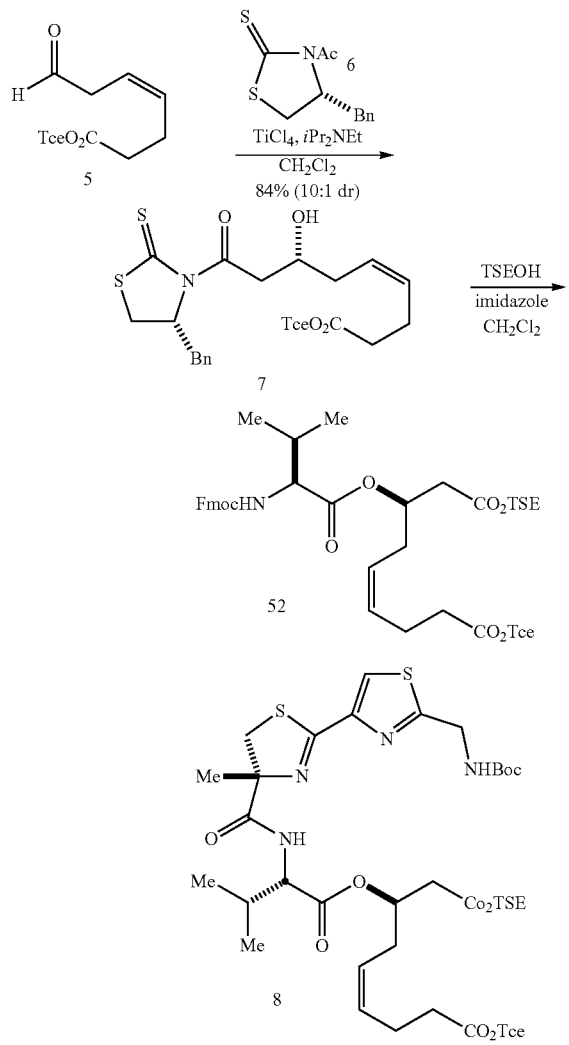

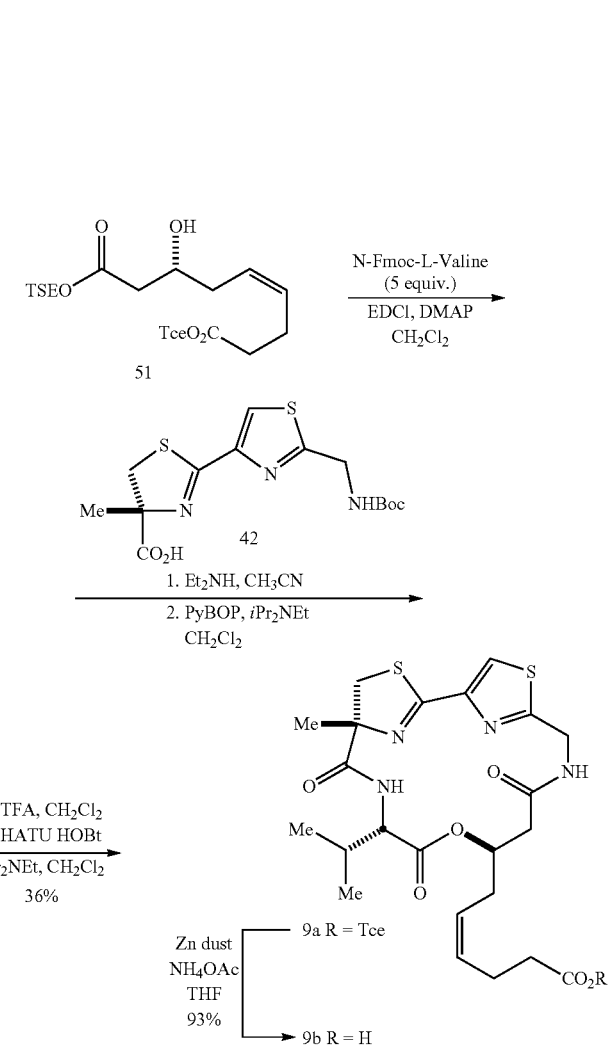

(R,Z)-2,2,2-trichloroethyl 9-((R)-4-benzyl-2-thioxothiazolidin-3-yl)-7-hydroxy-9-oxonon-4-enoate 7

A solution of the chiral auxiliary (887 mg, 3.53 mmol) in CH$_2$Cl$_2$ (28.5 mL) was cooled to 0° C., followed by addition of TiCl$_4$ (0.47 mL, 4.39 mmol). The reaction was allowed to stir for 5 minutes, then cooled to −78° C., before iPr$_2$NEt (0.76 mL, 4.37 mmol) were slowly added and stirred for 2 hours. The aldehyde was dissolved in CH$_2$Cl$_2$ (2.2 mL) and added dropwise to the auxiliary solution, then stirred for 1.5 hours. The reaction was quenched with saturated aq NH$_4$Cl and diluted with CH$_2$Cl$_2$ and warmed to room temperature. The reaction was extracted with CH$_2$Cl$_2$, then washed with brine and dried over Na$_2$SO$_4$, filtered and condensed. Purification was accomplished with silica gel chromatography (30% EtOAc/Hex) to afford yellow oil. $^1$H NMR (400 MHz, CDCl$_3$) d 83 m, 1H), 1.23 (s, 1H), 2.35 (m, 2 H), 2.45 (m, 2H), 2.53 (m, 2H), 2.88 (dd, 3.2, 11.6 Hz, 1 H), 3.02 (dd, 10.4, 13.2 Hz, 1 H), 3.17 (m, 2 H), 3.42 (m, 2 H), 3.62 (dd, 2.8, 17.6 Hz, 1 H) 4.15 (m, 2 H), 4.73 (s, 2H), 5.37 (m, 1 H), 5.52 (m, 2H), 7.30 (m, 5 H). $^{13}$C NMR (75 MHz, CDCl$_3$) d 22.8, 29.8, 32.2, 33.8, 34.3, 34.5, 36.9, 45.1, 45.5, 67.7, 68.2, 68.4, 68.5, 95.1, 126.8, 127.4, 129.1, 129.6, 130.5, 136.5, 169.1, 171.6, 173.1, 173.7. HRMS (ESI): m/z calcd. for C$_{21}$H$_{25}$Cl$_3$NO$_4$S$_2$ (M+H)$^+$524.02742. found 524.02851 [α]$_D$=−74.2 (c 2, CHCl$_3$)

(R,Z)-1-(2,2,2-trichloroethyl) 9-(2-(trimethylsilyl) ethyl) 7-hydroxynon-4-enedioate 51

The alcohol (764 mg, 1.45 mmol) dissolved in CH$_2$Cl$_2$ (2.9 mL) was treated with imidazole (148 mg, 2.175 mmol) followed by the addition of 2-(trimethylsilyl)ethanol (2.08 mL, 14.5 mmol). The reaction was stirred overnight, then condensed and purified by silica gel chromatography (30% EtOAc/Hex) to give the protected β-hydroxy acid as yellow oil. $^1$H NMR (300 MHz, CDCl$_3$) d 0.04 (s, 9 H), 0.99 (m, 2H), 2.30 (m, 2 H), 2.45 (m, 4 H), 2.54 (m, 2H), 4.06 (m, 1H), 4.20 (m, 2 H), 4.73 (s, 2H), 5.52 (m, 2 H). $^{13}$C NMR (75 MHz, CDCl$_3$) d −0.127, 17.5, 22.8, 33.8, 34.5, 41.0, 63.3, 67.9, 74.1, 95.1, 126.8, 130.3 171.7, 173.2. [α]$_D$=−1.7 (c 2, CHCl$_3$)

(R,Z)-1-(2,2,2-trichloroethyl) 9-(2-(trimethylsilyl) ethyl) 7-((S)-2-(((9H-fluoren-9-yl)methoxy)carbonylamino)-3-methylbutanoyloxy)non-4-enedioate 52

The protected acid (97 mg, 0.224 mmol) and N-Fmoc-L-Val (380 mg, 1.123 mmol) were dissolved in $CH_2Cl_2$ (4.08 mL) and cooled to 0° C. EDCI (258 mg, 1.347 mmol) and DMAP (2.7 mg, 0.0225 mmol) were dissolved in $CH_2Cl_2$ (1.02 mL) and added to the cooled reaction followed by the slow addition of $iPr_2NEt$ (0.23 mL, 1.347 mmol). The reaction was allowed to warm to room temperature and stirred overnight, then condensed and purified with column chromatography (30% EtOAc/Hex) $^1H$ NMR (300 MHz $CDCl_3$) d 3 s, 9 H), 0.88 (d, 3 H), 0.97 (m, 5 H) 2.15 (m, 1 H), 2.43 (m, 3 H), 2.50 (d, 2 H), 2.59 (m, 3 H), 4.25 (m, 3 H), 4.38 (m, 2 H), 4.73 (s, 2H), 5.32 (m, 2 H) 5.43, (m, 1 H), 5.53 (m, 1 H), 7.35 (m, 4 H), 7.60 (d, 2 H), 7.76 (d, 2 H). $^{13}C$ NMR (75 MHz, $CDCl_3$) d −1.27, 17.5, 19.2, 22.8, 31.4, 31.7, 33.7, 38.7, 47.4, 59.1, 63.3, 67.2, 71.5, 71.6, 74.1, 95.1, 120.2, 125.1, 125.3, 127.2, 127.9, 131.1, 131.2, 141.5, 143.9, 144.1, 156.3, 156.4. $(M+Na^-)$ calcd for $C_{36}H_{46}Cl_3NO_8Si$ 753.20627. found 776.19549. $[\alpha]_D$=0.0 (c 2, $CHCl_3$)

(R,Z)-1-(2,2,2-trichloroethyl) 9-(2-(trimethylsilyl) ethyl) 7-((S)-2-((R)-2-(2-((tert-butoxycarbonylamino)methyl)thiazol-4-yl)-4-methyl-4,5-dihydrothiazole-4-carboxamido)-3-methylbutanoyloxy) non-4-enedioate 8.

The protected amine (118 mg, 0.157 mmol) was dissolved in $CH_2Cl_2$ (7.85 mL) and treated with $Et_2NH$, then allowed to stir for 2 hrs. The reaction was concentrated, then taken up in EtOAc and re-concentrated again to remove any left-over $Et_2NH$. The thiazolinethiazole (61.7 mg, 0.172 mmol) and PyBOP (164 mg, 0.471 mmol) were dissolved in $CH_2Cl_2$ (2.87 mL) and treated with $iPr_2NEt$ and allowed to stir for 5 minutes. Then the crude amine in $CH_3CN$ (1.42 mL) was slowly added to the PyBOP solution and allowed to stir overnight. The reaction was then condensed and purified with column chromatography (30-50% EtOAc/Hex). $^1H$ NMR (300 MHz $CDCl_3$) d 3 s, 9 H), 0.82 (d, J=3 H), 0.88 (m, 3 H), 0.97 (m, 2 H), 1.47 (s, 9 H), 1.62 (s, 3 H), 2.15 (m, 1 H), 2.45 (m, 3 H), 2.57 (m, 5 H), 3.34 (d, J=11.4 1 H), 3.81 (d, J=11.4, 1 H), 4.15 (m, 2 H), 4.48 (m, 1H), 4.63 (d, J=6.3Hz, 2 H), 4.74 (s, 2 H), 5.31 (m, 2 H), 5.43 (m, 1 H), 5.54 (m, 1 H), 8.06 (s, 1 H). $^{13}C$ NMR (75 MHz, $CDCl_3$) d −1.3, 17.5, 17.7, 19.3, 22.8, 24.9, 28.5, 31.2, 33.7, 38.7, 38.8, 41.6, 42.6, 51.4, 57.3, 63.3, 71.5, 74.1, 80.7, 85.0, 95.1, 125.1, 125.3, 131.0, 131.1, 148.5, 155.9, 170.3, 170.4, 170.8, 170.9, 171.4, 171.5, 174.4. $(M+H^-)$ calcd for $C_{35}H_{53}C_{13}N_4O_8S_2Si$ 870.21108. found 871.21836. $[\alpha]_D$=−19.86 (c 2, $CHCl_3$)

Formation of the Trichloroethyl Ester Protected Largazole Azumamide Hybrid 9a

The acyclic precursor (77 mg, 0.088 mmol) was dissolved in $CH_2Cl_2$ (2.95 mL) and cooled to 0° C. TFA (0.15 mL) was slowly added to the cooled solution. The reaction was allowed to warm to room temperature and stirred overnight. The reaction was then condensed, and re-dissolved in toluene and condensed again to remove any excess TFA. The crude amino acid was dissolved in $CH_2Cl_2$ (4.4 mL), then cooled to 0° C. and treated with $iPr_2NEt$ (0.093 mL, 0.53 mmol) and stirred for 30 min. In a separate flask, HOBt (23 mg, 0.177 mmol), HATU (67 mg, 0.177 mmol) were dissolved in $CH_3CN$ (88.7 mL) and treated with $iPr_2NEt$ (0.093 mL, 0.53 mmol). The crude amino acid solution was then added via syringe pump addition to the HATU solution in a 10-hour addition. The reaction was allowed to stir for an additional 6 hours before solvents were removed and purified with silica gel chromatography (30%-50% EtOAc/Hex). $^1H$ NMR (300 MHz $CDCl_3$) d 0. 47 d, J=6.9Hz, 3 H), 0.69 (d, J=8.7 Hz, 3 H), 1.24 (s, 1H), 1.87 (s, 3 H), 2.13 (m, 1 H), 2.43 (m, 3 H), 2.52 (d, J=6.6 Hz, 2 H), 2.72 (m, 4 H), 3.29 (d, J=12.3Hz, 1 H), 4.05 (d, J=11.4Hz, 1 H), 4.27 (dd, J=3, 17.7 Hz, 1 H), 4.64 (dd, J=3, 9.3Hz, 1 H), 4.75 (s, 2 H), 5.25 (m, 2 H), 5.40 (m, 1 H), 5.53 (m, 1 H), 6.33 (m, 1 H), 7.10 (d, J=9.3Hz, 1 H), 7.78 (s, 1 H) $^{13}C$ NMR (75 MHz, $CDCl_3$) d 14.4, 16.5, 18.5, 18.7, 19.3, 22.8, 24.1, 24.9, 29.4, 31.2, 32.7, 33.7, 33.9, 34.3, 35.5, 39.2, 41.2, 43.4, 43.7, 57.8, 59.7, 60.6, 72.5, 74.1, 83.8, 95.1, 110.5, 118.4, 124.9, 125.1, 127.3, 131.2, 146.8, 167.0, 168.7, 169.5, 170.6, 171.5, 173.2. $(M+H^-)$ calcd for $C_{25}H_{31}Cl_3N_4O_6S_2$ 675.0637. found 675.06428 $[a]_D$=−0.94 (c 2, $CHCl_3$)

Largazole Auzumamide E Hybrid 9b

The macrocycle (40) (9.8 mg, 0.015 mmol) was dissolved in dry THF (0.5 mL, 0.03M) and vigorously stirred. Then Zn dust (35 mg, 36 mmol) was added to the solution followed by 1M $NH_4OAc$ (0.083 mL, 0.18M) and allowed to stir for 24 hours under argon. The reaction was then filtered and taken up in EtOAc and washed with 5% aq $KHSO_4$ (2×2 mL) and Brine (2×2 mL) then dried over $Na_2SO_4$, filtered and solvents removed. Purification by PTLC ($MeOH/CH_2Cl_2$ 10%). $^1H$ NMR (300 MHz $CDCl_3$) d 0.47 (d, J=6.9Hz, 3 H), 0.69 (d, J=6.9 Hz, 3 H), 0.85 (m, 2 H), 1.88 (s, 3 H), 2.14 (m, 1 H), 2.41 (m, 5 H), 2.71 (m, 4 H), 3.29 (d, J=11.4Hz, 1 H), 4.06 (d, J=11.4Hz, 1 H), 4.27 (dd, J=3.3, 17.4Hz, 1 H), 4.45 (d, J=6.0 Hz, 2 H), 4.64 (dd, J=3.0, 9.3Hz, 1 H), 5.29 (m, 2 H), 5.42 (m, 1H), 5.51 (m, 1 H), 5.85 (t, J=6.0 Hz, 1 H), 6.40 (m, 1 H), 7.11 (d, J=9.3Hz, 1 H), 7.79 (s, 1 H). $^{13}C$ NMR (75 MHz, $CDCl_3$) d 14.4, 16.6, 19.2, 21.8, 24.2, 29.9, 31.1, 33.7, 39.3, 41.3, 43.5, 57.8, 60.6, 68.4, 68.6, 72.4, 124.8, 131.4, 168.2, 169.6, 170.2, 172.1, 173.6. (M−H=) calcd for $C_{23}H_{30}N_4O_6S_2$ 521.1534. found 521.15292. $[a]_D$=+ 10.107 (c 2, $CHCl_3$)

Example 12

Metathesis route to Largazole hybrids

General procedure for the cross-metathesis reactions

Adapting the procedure described by Luesch and co-workers, macrocycle 10 was dissolved in the indicated solvent (to ~0.026M) and heated to reflux under argon. Solutions of sacrificial olefin (2.0 equiv., ~0.26M) and catalyst (0.2 equiv., ~0.052M) were then added to the reaction. The resulting mixture was stirred at reflux for a further 3 hrs, with equivalent portions of olefin (2.0 equiv., ~0.26M in toluene) and catalyst (0.2 equiv., ~0.052M in toluene) being added each hour. After the last addition of olefin and catalyst, the reaction was refluxed for 1 hr. and then cooled to room temperature. Several drops of DMSO were added and the mixture was stirred overnight. Concentration in vaccuo, followed by column chromatography, provided the substituted olefins as products. Alternatively, dichloroethane can be used as the solvent and Grubbs-Hoveyda second generation as the catalyst in the cross-metathesis reaction.

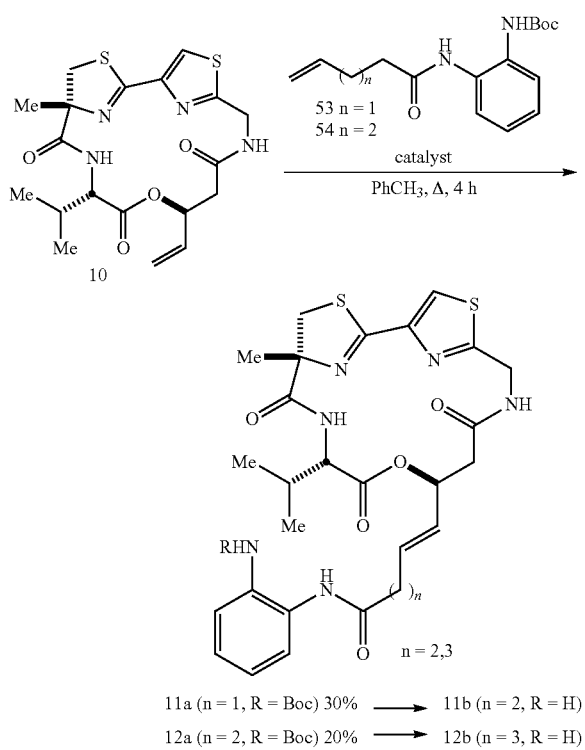

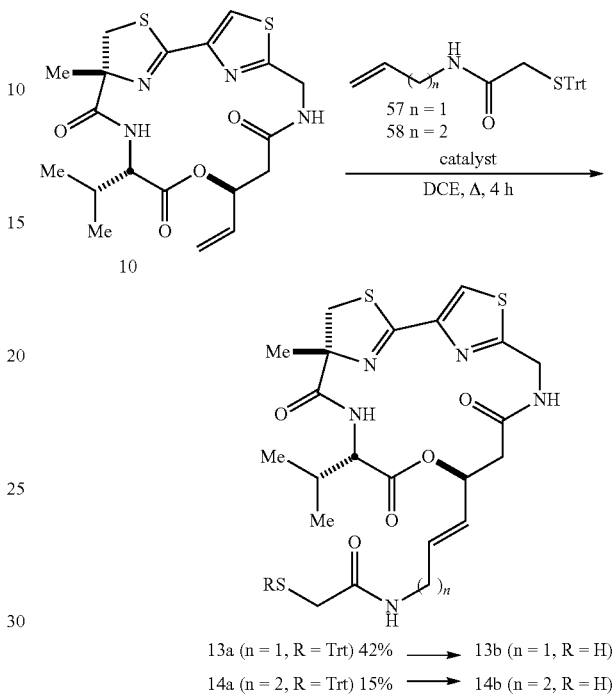

11a (n = 1, R = Boc) 30% → 11b (n = 2, R = H)
12a (n = 2, R = Boc) 20% → 12b (n = 3, R = H)

13a (n = 1, R = Trt) 42% → 13b (n = 1, R = H)
14a (n = 2, R = Trt) 15% → 14b (n = 2, R = H)

Boc-Protected Benzamide 11a and Amine 11b

According to the general procedure, 0.025 g (0.057 mmol) macrocycle 10 was combined with olefin 53 to yield 0.012 g (0.017 mmol, 30% yield) compound IIa, which eluted slowly in 100% EtOAc. Clear oil. $^1$H NMR (300 MHz, CDCl$_3$) δ 0.62 (d J=6.9Hz, 3H), 0.73 (d J=6.9Hz, 3H), 1.53 (s, 9H), 1.87 (s, 3H), 1.98-2.00 (m, 1H), 2.42-2.65 (m, 5H), 2.77 (dd J=6.0, 15.6 Hz, 1H), 3.31 (d J=11.4Hz, 1H), 3.91 (dd J=4.2, 16.8 Hz, 1H), 4.00 (d J=11.4Hz, 1H), 4.54 (dd J=4.8, 9.3Hz, 1H), 4.86 (dd J=8.1, 16.8 Hz, 1H), 5.69-5.79 (m, 2H), 5.86-5.97 (m, 1H), 6.61-6.67 (m, 1H), 6.90 (t J=7.8 Hz, 1H), 6.98 (d J=7.2Hz, 1H), 7.08 (td J=1.2, 8.1 Hz, 1H), 7.19 (d J=9.0 Hz, 1H), 7.48 (d J=7.8 HZ, 1H), 7.67 (s, 1H), 7.98 (bs, 1H), 8.40 (bs, 1H). HRMS (ESI): m/z calcd. for $C_{33}H_{42}N_6NaO_7S_2$ (M+Na)$^+$721.24541. found 721.24526.

0.010 g Benzamide 11a was deprotected in 1 mL CH$_2$Cl$_2$ and 0.2 mL TFA. After 2 hrs, the solvents were removed and the product amine 11b purified by preparative thin layer chromatography.

Boc-Protected Benzamide 12a and Amine 12b

According to the general procedure, 0.039 g (0.089 mmol) macrocycle 10 was combined with olefin 54 to yield 0.012 g (0.017 mmol, 20% yield) compound 12a, which eluted slowly in 100% EtOAc. Clear oil. $^1$H NMR (300 MHz, CDCl$_3$) δ 0.59 (d J=6.9Hz, 3H), 0.73 (d J=6.9Hz, 3H), 1.50 (s, 9H), 1.86 (s, 3H), 1.99-2.00 (m, 1H), 2.15-2.32 (m, 3H), 2.32-2.41 (m, 3H), 2.66-2.73 (m, 2H), 3.30 (d J=11.4Hz, 1H), 4.02 (d J=11.4Hz, 1H), 4.28 (dd J=3.6, 17.7 Hz, 1H), 4.57 (dd J=4.5, 9.6 Hz, 1H), 4.99 (dd J=6.9, 17.7 Hz, 1H), 5.61-5.72 (m, 2H), 5.86 (dt J=7.2, 14.4Hz, 1H), 6.59-6.66 (m, 1H), 7.01 (t J=8.4Hz, 1H), 7.11-7.16 (m, 3H), 7.26 (d J=9.0 Hz, 1H), 7.49 (d J=8.1 Hz, 1H), 7.67 (s, 1H), 8.48 (s, 1H). HRMS (ESI): m/z calcd. for $C_{34}H_{44}N_6NaO_7S_2$ (M+Na)$^+$735.26106. found 735.2609. 0.004 g Benzamide 12a was deprotected in 1 mL CH$_2$Cl$_2$ and 0.2 mL TFA. After 2 hrs, the solvents were removed and the product amine 12b purified by preparative thin layer chromatography.

S-Trityl-α-thioamide 13a According to the general procedure, 0.060 g (0.14 mmol) macrocycle 10 was combined with olefin 55 in presence of the Hoveyda-Grubbs second generation catalyst in toluene to yield 0.046 g (0.058 mmol, 42% yield) compound 13a, which eluted in 10:1 CH$_2$Cl$_2$:CH$_3$OH. Clear oil. (13a): [α]$^{24}_D$: +12.4 (c=1, CHCl$_3$). $^1$H NMR (400 MHz, CDCl$_3$) δ 0.53 (d J=6.8 Hz, 3H), 0.69 (d J=6.8 Hz, 3H), 1.81 (s, 3H), 1.96-2.10 (m, 3H), 2.64 (dd J=3.6, 15.6 Hz, 1H), 2.76 (dd J=8.8, 15.6 Hz, 1H), 3.03 (s, 2H), 3.25 (d J=11.2Hz, 1H), 3.52 (t J=5.6 Hz, 1H), 4.00 (d J=11.2Hz, 1H), 4.25 (dd J=3.2, 17.2Hz, 1H), 4.55 (dd J=4.0, 9.6 Hz, 1H), 5.20 (dd J=8.8, 17.2Hz, 1H), 5.49 (dd J=6.4, 15.6 Hz, 1H), 5.63-5.96 (m, 1H), 5.71 (dt J=4.2, 15.6 Hz, 1H), 6.00 (t J=4.2Hz, 1H), 6.50-6.52 (m, 1H), 7.15-7.29 (m, 9H), 7.37-7.39 (m, 6H), 7.70 (s, 1H). $^{13}$C NMR (100.6 MHz, CDCl$_3$): δ 14.3, 17.1, 19.1, 24.4, 29.9, 34.1, 35.9, 40.8, 41.2, 41.4, 43.5, 58.2, 68.0, 71.5, 127.3, 128.1, 128.4, 129.6, 130.0, 144.1, 168.4, 168.9, 169.3. HRMS (ESI): m/z calcd. for $C_{41}H_{43}N_5NaO_5S_3$ (M+Na)$^+$804.23185. found 804.23259.

Thiol 13b

According to the general procedure, 0.035 g 13a was deprotected to give 0.022 g 13b after preparative thin layer chromatography. (13b): [α]$^{24}_D$: +6.1 (c=0.5, CHCl$_3$). $^1$H NMR (300 MHz, CDCl$_3$) δ 0.56 (d J=6.9Hz, 3H), 0.71 (d J=6.9Hz, 3H), 1.88 (s, 3H), 1.95 (t J=9.0 Hz, 1H), 2.04-2.16 (m, 1H), 2.26-2.33 (m, 2H), 2.70 (dd J=3.0, 16.2Hz, 1H), 2.88 (dd J=9.9, 16.2Hz, 1H), 3.24-3.32 (m, 2H), 3.19 (d J=8.7 Hz, 1H), 3.30 (d J=11.4Hz, 1H), 3.42-3.50 (m, 1H), 4.06 (d J=11.4Hz, 1H), 4.35 (dd J=3.6, 17.7 Hz, 1H), 4.61 (dd J=3.3, 9.3 Hz, 1H), 5.25 (dd J=9.3, 17.7 Hz, 1H), 5.56 (dd J=7.2, 15.3 Hz, 1H), 5.64-5.70 (m, 1H), 5.83 (dt J=7.2, 15.3 Hz, 1H), 6.44 (d J=6.0 Hz, 1H), 6.74 (s, 1H), 7.19 (d J=9.6 Hz, 1H), 7.80 (s, 1H). $^{13}$C NMR (100.6 MHz, CDCl$_3$): δ 17.0, 19.1, 24.5, 28.5, 32.3, 34.4, 38.8, 40.8, 41.3, 43.6, 58.1, 72.6, 77.4, 84.6, 124.6, 129.8, 131.8, 147.7, 168.2, 169.4, 169.5, 169.6, 173.7. HRMS (ESI): m/z calcd. for C$_{23}$H$_{31}$N$_5$NaO$_5$S$_3$ (M+Na)$^+$ 576.13795. found 576.13795.

S-Trityl-α-thioamide 14a

According to the general procedure, 0.052 g (0.12 mmol) macrocycle 10 was combined with olefin 56 in presence of the Grubbs second generation catalyst in toluene to yield 0.014 g (0.018 mmol, 15% yield) compound 14a, which eluted in 10:1 CH$_2$Cl$_2$:CH$_3$OH. Clear oil. (14a): [α]$^{24}_D$: +8.1 (c=1, CHCl$_3$). $^1$H NMR (300 MHz, CDCl$_3$) δ 0.50 (d J=6.9 Hz, 3H), 0.67 (d J=6.9 Hz, 3H), 1.89 (s, 3H), 2.00-2.11 (m, 3H), 2.61 (dd J=2.7, 16.5 Hz, 1H), 2.78 (dd J=10.2, 16.5 Hz, 1H), 2.94-3.05 (m, 2H), 3.10 (s, 2H), 3.27 (d J=11.4 Hz, 1H), 4.04 (d J=11.4 Hz, 1H), 4.25 (dd J=3.0, 17.7 Hz, 1H), 4.58 (dd J=3.6, 9.6 Hz, 1H), 5.25 (dd J=9.3, 17.4 Hz, 1H), 5.43 (dd J=6.9, 15.6 Hz, 1H), 5.57-5.63 (m, 1H), 5.69 (dt J=6.9, 11.1 Hz, 1H), 6.06 (t J=5.4 Hz, 1H), 6.33 (dd J=3.0, 9.3 Hz, 1H), 7.14 (d J=9.6 Hz, 1H), 7.20-7.37 (m, 9H), 7.38-7.42 (m, 6H), 7.75 (s, 1H). $^{13}$C NMR (100.6 MHz, CDCl$_3$): δ 16.9, 19.1, 24.4, 32.2, 34.4, 36.1, 38.9, 40.7, 41.3, 43.6, 58.0, 68.0, 72.4, 77.5, 84.5, 124.7, 127.3, 128.4, 129.2, 129.7, 131.8, 144.2, 147.6, 168.1, 169.1, 169.5, 173.7. HRMS (ESI): m/z calcd. for C$_{42}$H$_{45}$N$_5$NaO$_5$S$_3$ (M+Na)$^+$ 818.2475. found 818.2469.

Thiol 14b

According to the general procedure, 0.035 g 14a was deprotected to give 0.022 g 14b after preparative thin layer chromatography. (14b): [α]$^{24}_D$: +15.6 (c=0.5, CHCl$_3$). $^1$H NMR (300 MHz, CDCl$_3$) δ 0.56 (d J=6.9 Hz, 3H), 0.71 (d J=6.9 Hz, 3H), 1.88 (s, 3H), 1.95 (t J=9.0 Hz, 1H), 2.04-2.16 (m, 1H), 2.26-2.33 (m, 2H), 2.70 (dd J=3.0, 16.2 Hz, 1H), 2.88 (dd J=9.9, 16.2 Hz, 1H), 3.24-3.32 (m, 2H), 3.19 (d J=8.7 Hz, 1H), 3.30 (d J=11.4 Hz, 1H), 3.42-3.50 (m, 1H), 4.06 (d J=11.4 Hz, 1H), 4.35 (dd J=3.6, 17.7 Hz, 1H), 4.61 (dd J=3.3, 9.3 Hz, 1H), 5.25 (dd J=9.3, 17.7 Hz, 1H), 5.56 (dd J=7.2, 15.3 Hz, 1H), 5.64-5.70 (m, 1H), 5.83 (dt J=7.2, 15.3 Hz, 1H), 6.44 (d J=6.0 Hz, 1H), 6.74 (s, 1H), 7.19 (d J=9.6 Hz, 1H), 7.80 (s, 1H). $^{13}$C NMR (100.6 MHz, CDCl$_3$): δ 17.0, 19.1, 24.5, 28.5, 32.3, 34.4, 38.8, 40.8, 41.3, 43.6, 58.1, 72.6, 77.4, 84.6, 124.6, 129.8, 131.8, 147.7, 168.2, 169.4, 169.5, 169.6, 173.7. HRMS (ESI): m/z calcd. for C$_{23}$H$_{31}$N$_5$NaO$_5$S$_3$ (M+Na)$^+$ 576.13795. found 576.13795.

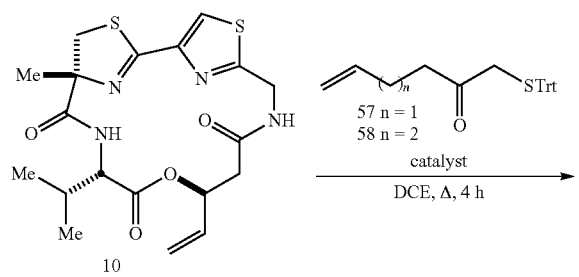

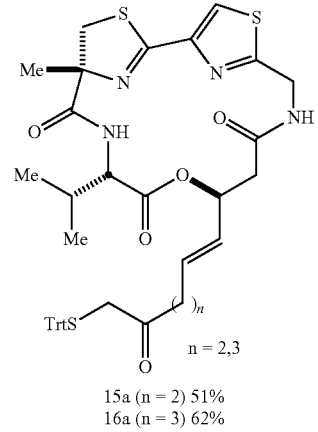

15a (n = 2) 51%
16a (n = 3) 62%

S-Trityl-α-thioketone 15a

According to the general procedure, 0.044 g (0.10 mmol) macrocycle 10 was combined with olefin 57 in presence of the Hoveyda-Grubbs second generation catalyst in 1,2-dichloroethane to yield 0.040 g (0.051 mmol, 51% yield) compound 15a, which eluted in EtOAc. Clear oil. (15a): [α]$^{24}_D$: +11.0 (c=1, CHCl$_3$). $^1$H NMR (300 MHz, CDCl$_3$) δ 0.55 (d J=6.9 Hz, 3H), 0.71 (d J=6.9 Hz, 3H), 1.85 (s, 3H), 2.04-2.41 (m, 7H), 2.66 (dd J=3.6, 15.9 Hz, 1H), 2.79 (dd J=8.4, 15.9 Hz, 1H), 2.93 (d J=14.7 Hz, 1H), 3.00 (d J=14.7 Hz, 1H), 3.28 (d J=11.4 Hz, 1H), 4.03 (d J=11.4 Hz, 1H), 4.29 (dd J=6.3, 17.7 Hz, 1H), 4.57 (dd J=3.9, 9.6 Hz, 1H), 5.25 (dd J=9.3, 17.7 Hz, 1H), 5.45 (dd J=6.3, 15.3 Hz, 1H), 5.62-5.68 (m, 1H), 5.79 (dt J=6.3, 15.3 Hz, 1H), 6.54 (dd J=2.4, 9.0 Hz, 1H), 7.18-7.33 (m, 10H), 7.36-7.41 (m, 6H), 7.72 (s, 1H). $^{13}$C NMR (100.6 MHz, CDCl$_3$): δ 17.1, 19.1, 24.5, 26.3, 34.2, 40.4, 40.8, 41.4, 42.8, 43.5, 58.2, 67.3, 71.8, 84.7, 124.4, 127.2, 127.4, 128.3, 129.8, 133.7, 144.3, 147.7, 164.8, 168.3, 168.9, 169.5, 173.7, 205.5. HRMS (ESI): m/z calcd. for C$_{42}$H$_{44}$N$_4$NaO$_5$S$_3$ (M+Na)$^+$ 803.2366. found 803.23654.

S-Trityl-α-thioketone 16a

According to the general procedure, 0.048 g (0.11 mmol) macrocycle 10 was combined with olefin 58 in presence of the Hoveyda-Grubbs second generation catalyst in 1,2-dichloroethane to yield 0.054 g (0.067 mmol, 62% yield) compound 16a, which eluted in EtOAc. Clear oil. (16a): [α]$^{24}_D$: +5.1 (c=2, CHCl$_3$). $^1$H NMR (300 MHz, CDCl$_3$) δ 0.52 (d J=6.9 Hz, 3H), 0.70 (d J=6.9 Hz, 3H), 1.43-1.53 (m, 2H), 1.87 (s, 3H), 1.89-1.97 (m, 2H), 2.06-2.23 (m, 3H), 2.65 (dd J=2.7, 16.5 Hz, 1H), 2.82 (dd J=10.5, 16.5 Hz, 1H), 3.06 (s, 2H), 3.28 (d J=11.4 Hz, 1H), 4.05 (d J=11.4 Hz, 1H), 4.26 (dd J=2.4, 17.7 Hz, 1H), 4.60 (dd J=3.3, 9.3 Hz, 1H), 5.27 (dd J=9.0, 17.7 Hz, 1H), 5.38 (dd J=6.9, 17.7 Hz, 1H), 5.60-5.66 (m, 1H), 5.74 (dt J=6.6, 15.3 Hz, 1H), 6.43 (d J=7.8 Hz, 1H), 7.15-7.33 (m, 10H), 7.37-7.44 (m, 6H), 7.77 (s, 1H). $^{13}$C NMR (100.6 MHz, CDCl$_3$): δ 16.9, 19.2, 22.9, 24.4, 31.5, 34.5, 40.8, 41.0, 41.3, 42.9, 43.6, 57.9, 67.3, 72.6, 84.6, 124.5, 127.2, 127.3, 128.3, 129.8, 134.8, 144.4, 147.7, 164.8, 168.2, 169.2, 169.7, 173.8, 205.8. HRMS (ESI): m/z calcd. for C$_{43}$H$_{46}$N$_4$NaO$_5$S$_3$ (M+Na)$^+$ 817.25225. found 817.25292.

Example 13

Synthesis of Cysteine & Thiazole-Thiazole Analogs

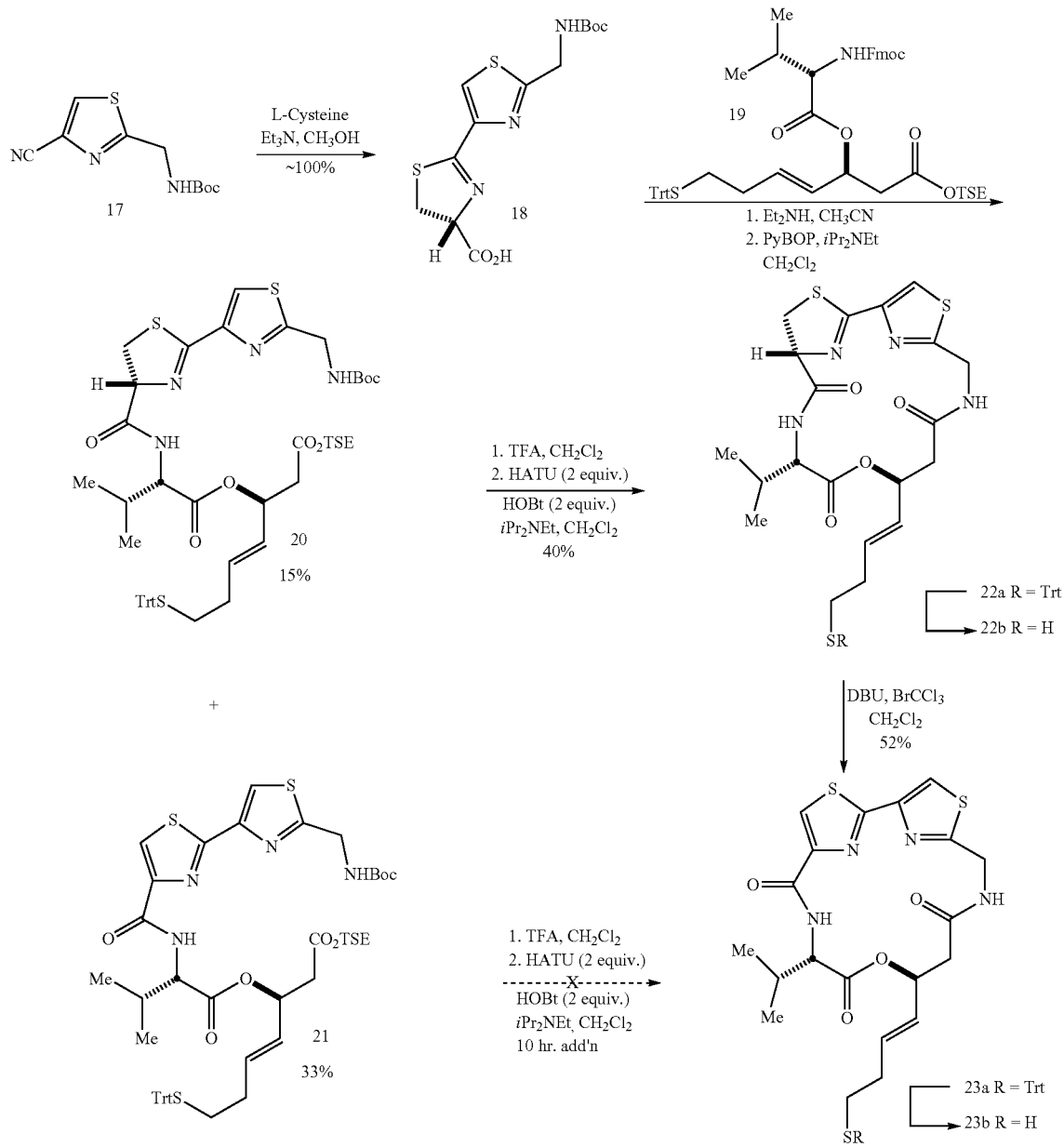

2-[2-[(tert-Butoxycarbonyl)methyl]thiazol-4-yl]-4,5-dihydrothiazole-4-carboxylic acid (18)

0.800 g (3.3 mmol) Thiazole nitrile 17 (Reiner, J., et al. 2002 *Bioorg Med Chem Lett* 12(8):1203-1208) and 0.446 g (3.6 mmol, 1.1 equiv.) cysteine were dissolved 33 mL dry $CH_3OH$ and 0.5 mL dry $Et_3N$ was added dropwise. The resulting solution was heated at reflux overnight. The reaction was subsequently cooled to room temperature and the solvents removed in vacuo. The crude reaction mixture was then dissolved in sat. aqu. $NaHCO_3$ and washed with diethyl ether. The aqueous layer was then acidified to pH ~3-4 by dropwise addition of 3N HCl and extracted with EtOAc (3×30 mL). The combined organics were dried over $Na_2SO_4$, filtered, and concentrated to provide 1.15 g (3.3 mmol, ~100% yield from 17) of acid 18 in spectroscopically pure form. Pale orange foam. $[\alpha]^{24}_D$: +30.9 (c=1, $CH_3OH$). $^1H$ NMR (400 MHz, $CDCl_3$) δ 9.79 (bs, 1H), 7.98 (s, 1H), 5.59 (s, 1H), 4.59 (d J=6.3Hz, 2H), 3.88 (d J=11.4Hz, 1H), 3.30 (d J=11.4Hz, 1H), 1.66 (s, 3H). $^{13}C$ NMR (100.6 MHz, $CDCl_3$): δ 175.74, 170.38, 170.16, 165.03, 155.91, 147.77, 123.3, 84.23, 80.70, 42.39, 41.31, 28.51, 27.17, 26.67, 24.30. HRMS (ESI): m/z calcd. for $C_{14}H_{19}N_3NaO_4S_2$ $(M+Na)^+$ 380.07147. found 380.07165.

Thiazoline-Thiazole Acyclic Precursor 20 and Thiazole-Thiazole Acyclic Precursor 0.300 g (0.36 mmol, 1.0 equiv.) diester 19 and 0.147 g (0.42 mmol, 1.2 equiv.) acid 18 were coupled according to the same procedure described above for synthesis of 43. The two resulting products could be separated via column chromatography, washing first with 4:1, then with 2:1 hexanes:EtOAc. 0.110 g (33% yield) 21 eluted first, followed quickly by 0.052 g (15% yield) 20. (20): $^1$H NMR (300 MHz, CDCl$_3$) δ 0.03 (s, 9H), 0.75 (d J=6.9Hz, 3H), 0.82 (d J=6.9Hz, 3H), 0.93-0.99 (m, 2H), 1.49 (s, 9H), 1.99-2.21 (m, 5H), 2.55 (dd J=5.4, 15.6 Hz, 1H), 2.69 (dd J=7.8, 15.6 Hz, 1H), 3.61-3.74 (m, 2H), 4.12-4.18 (m, 2H), 4.53 (dd J=4.8, 9.0 Hz, 1H), 4.62 (d J=6.0 Hz, 1H), 5.19 (t J=9.0 Hz, 1H), 5.25-5.32 (m, 1H), 5.37 (dd J=7.5, 15.3 Hz, 1H), 5.59-5.74 (m, 2H), 7.16-7.29 (m, 9H), 7.37-7.40 (m, 6H), 7.92 (s, 1H). $^{13}$C NMR (100.6 MHz, CDCl$_3$): δ −1.2, 17.5, 17.7, 19.2, 28.6, 31.3, 31.5, 31.7, 35.8, 39.9, 42.6, 57.0, 63.4, 66.8, 72.1, 79.4, 80.7, 121.7, 126.8, 128.0, 128.1, 129.8, 134.3, 145.0, 148.7, 155.9, 165.7, 169.9, 170.6, 171.2 HRMS (ESI): m/z calcd. for C$_{49}$H$_{63}$N$_4$O$_7$S$_3$Si (M+H)$^+$ 943.35463. found 943.3619. (21): [α]$^{24}_D$: −1.1 (c=2, CHCl$_3$). $^1$H NMR (300 MHz, CDCl$_3$) 8-0.01 (s, 9H), 0.90-0.98 (m, 8H), 1.49 (s, 9H), 2.01-2.08 (m, 2H), 2.14-2.21 (m, 2H), 2.23-2.30 (m, 1H), 2.56 (dd J=5.4, 15.6 Hz, 1H), 2.70 (dd J=8.1, 15.6 Hz, 1H), 4.11-4.16 (m, 2H), 4.66 (d J=5.7, 2H), 4.72 (dd J=4.8, 9.3Hz, 1H), 5.32-5.43 (m, 1H), 5.39 (dd J=8.7, 15.6 Hz, 1H), 5.63-5.76 (m, 2H), 7.19-7.30 (m, 8H), 7.37-7.44 (m, 7H), 7.88 (d J=9.0 Hz, 2H), 7.92 (s, 1H), 8.11 (s, 1H). $^{13}$C NMR (100.6 MHz, CDCl$_3$): δ −1.3, 17.5, 18.0, 19.4, 28.6, 31.3, 31.6, 32.0, 40.0, 42.6, 57.2, 63.5, 66.9, 72.3, 77.5, 80.8, 117.6, 124.4, 126.9, 127.9, 128.1, 129.8, 134.5, 145.1, 148.4, 150.4, 156.0, 161.2, 162.7, 170.5, 171.0. HRMS (ESI): m/z calcd. for C$_{49}$H$_{60}$N$_4$NaO$_7$S$_3$Si (M+Na)$^+$ 963.32911. found 963.32983.

S-Trityl Macrocycle 22a

According to the general procedure, 0.054 g acyclic precursor 20 was deprotected and cyclized to provide 0.030 g (72% yield) macrocycle 22a after purification by column chromatography. Eluent: EtOAc. (22a) Light yellow foam. [α]$^{24}_D$: +30.0 (c=1, CHCl$_3$). $^1$H NMR (300 MHz, 1:1 CDCl$_3$:CD$_3$OD) δ 0.39 (d J=6.9Hz, 3H), 0.63 (d J=6.9Hz, 3H), 1.97-2.18 (m, 5H), 2.54 (dd J=2.4, 16.5Hz, 1H), 3.66 (dd J=9.0, 14.7 Hz, 1H), 3.95 (dd J=1.2, 11.4Hz, 1H), 4.12 (d J=17.4Hz, 1H), 4.54 (dd J=3.6, 9.6 Hz, 1H), 5.15 (d J=17.4Hz, 1H), 5.29-5.34 (m, 1H), 5.35 (dd J=6.9, 15.6 Hz, 1H), 5.50-5.57 (m, 1H), 5.65 (dt J=6.9, 15.3Hz, 1H), 6.98 (d J=9.6 Hz, 1H), 7.14-7.26 (m, 10H), 7.32-7.36 (m, 6H), 7.77 (s, 1H). $^{13}$C NMR (100.6 MHz, CDCl$_3$): δ 16.6, 19.4, 31.6, 31.8, 34.4, 37.8, 38.9, 40.1, 41.2, 58.0, 73.2, 78.2, 125.7, 127.1, 127.3, 128.3, 130.0, 133.8, 145.2, 147.0, 166.4, 169.0, 169.5, 171.0, 171.5. HRMS (ESI): m/z calcd. for C$_{39}$H$_{40}$N$_4$NaO$_4$S$_3$ (M+Na)$^+$ 747.21039. found 747.21042.

Thiol 22b

According to the general procedure, 0.035 g 22a was deprotected to give 0.022 g 22b after preparative thin layer chromatography. Clear oil. (22b) [α]$^{24}_D$: −1.1 (c=0.2, CHCl$_3$). $^1$H NMR (300 MHz, 1:1 CDCl$_3$:CD$_3$OD) δ 0.52 (d J=6.9Hz, 3H), 0.70 (d J=6.9Hz, 3H), 1.42 (t J=4.8 Hz, 1H), 2.08-2.14 (m, 1H), 2.32-2.40 (m, 2H), 2.53-2.61 (m, 2H), 2.89 (dd J=10.2, 16.8 Hz, 1H), 3.68 (dd J=8.7, 14.1 Hz, 1H), 4.02 (d J=11.4Hz, 1H), 4.30 (dd J=3.3, 17.7 Hz, 1H), 4.63 (dd J=3.6, 9.6 Hz, 1H), 5.28 (dd J=9.3, 17.7 Hz, 1H), 5.40 (d J=6.0 Hz, 1H), 5.55 (ddt J=1.5, 6.6, 15.3Hz, 1H), 6.45-6.50 (m, 1H), 7.13 (d J=9.0 Hz, 1H), 7.79 (s, 1H). $^{13}$C NMR (100.6 MHz, CDCl$_3$): δ 16.8, 19.2, 24.1, 34.3, 36.6, 37.8, 38.9, 40.8, 41.4, 57.9, 72.3, 124.7, 129.0, 132.9, 147.5, 168.0, 169.1, 169.6, 170.8. HRMS (ESI): m/z calcd. for C$_{20}$H$_{26}$N$_4$NaO$_4$S$_3$ (M+Na)$^+$ 505.10139. found 505.10156.

S-Trityl-thiazole-thiazole Macrocycle 23a 0.020 g (0.028 mmol, 1.0 equiv.) 22a was dissolved in 1 mL dry CH$_2$Cl$_2$ and cooled to 0° C. 0.021 mL (0.14 mmol, 5.0 equiv.) DBU was added dropwise, followed by 0.014 mL (0.14 mmol, 5 equiv.) BrCCl$_3$ in 1 mL CH$_2$Cl$_2$. The reaction was allowed to warm to room temperature and stirred overnight. The resulting solution was then poured over cold (0° C.) saturated aqueous NaHCO$_3$, extracted, concentrated, and dried. The product was then purified by column chromatography, eluting in 1:2 hexanes:EtOAc (0.010 g, 52% yield). (23a) [α]$^{24}_D$: −7.0 (c=1, CHCl$_3$). $^1$H NMR (300 MHz, DMSO-d$_6$) δ 0.70 (d J=6.9Hz, 3H), 0.79 (d J=6.9 Hz, 3H), 1.91-1.99 (m, 2H), 2.07-2.12 (m, 2H), 2.16-2.24 (m, 1H), 2.33 (d J=14.1 Hz, 1H), 2.61 (dd J=10.8, 15.0 Hz, 1H), 4.39 (dd J=5.1, 17.4Hz, 1H), 4.77 (dd J=7.2, 17.4Hz, 1H), 5.17 (dd J=3.9, 9.9Hz, 1H), 5.35 (dd J=7.5, 15.0 Hz, 1H), 5.50-5.65 (m, 2H), 7.19-7.28 (m, 3H), 7.28-7.35 (m, 12H), 7.62 (d J=9.6 Hz, 1H), 8.30 (s, 1H), 8.32 (s, 1H), 8.72 (t J=6.3Hz, 1H). $^{13}$C NMR (100.6 MHz, DMSO-d$_6$): δ 16.6, 19.4, 31.6, 31.8, 34.4, 37.8, 38.9, 40.1, 41.2, 58.0, 73.2, 78.2, 125.7, 127.1, 127.3, 128.3, 130.0, 133.8, 145.2, 147.0, 166.4, 169.0, 169.5, 171.0, 171.5. HRMS (ESI): m/z calcd. for C$_{39}$H$_{38}$N$_4$NaO$_4$S$_3$ (M+Na)$^+$ 745.19474. found 745.19430.

Thiol 23b

According to the general procedure, 0.010 g 23a was deprotected to give 0.005 g 23b after preparative thin layer chromatography. (23b): Clear oil. [α]$^{24}_D$: −1.1 (c=0.2, CHCl$_3$). $^1$H NMR (300 MHz, DMSO-d$_6$) δ 0.82-0.85 (m, 6H), 2.21-2.29 (m, 4H), 2.39 (d J=14.1 Hz, 1H), 2.65 (dd J=10.5, 14.7 Hz, 1H), 4.40 (dd J=4.8, 17.1 Hz, 1H), 4.77 (dd J=7.2, 18.3Hz, 1H), 5.21 (dd J=3.9, 9.9Hz, 1H), 5.47-5.61 (m, 2H), 5.75 (dt J=6.9, 14.7 Hz, 1H), 7.68 (d J=9.9Hz, 1H), 8.31 (s, 1H), 8.33 (s, 1H), 8.74 (t J=5.4Hz, 1H). $^{13}$C NMR (100.6 MHz, DMSO-d$_6$): δ 16.8, 19.2, 24.1, 34.3, 36.6, 37.8, 38.9, 40.8, 41.4, 57.9, 72.3, 124.7, 129.0, 132.9, 147.5, 168.0, 169.1, 169.6, 170.8. HRMS (ESI): m/z calcd. for C$_{20}$H$_{24}$N$_4$NaO$_4$S$_3$ (M+Na)$^+$ 503.08519. found 503.08369.

Example 14

Synthesis of Thiazole to Pyridine Substitution

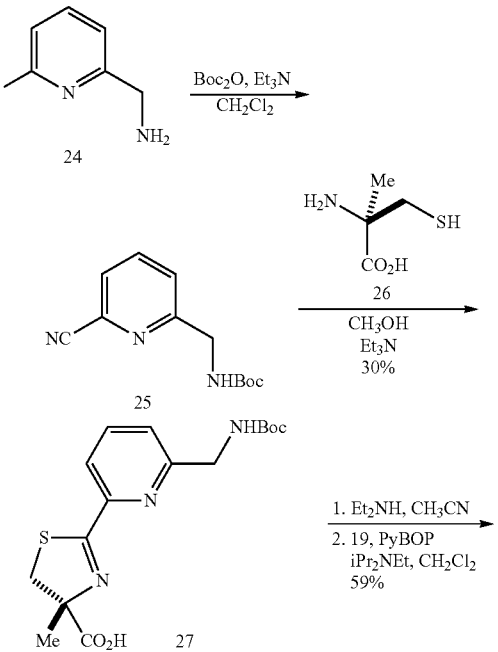

97
-continued

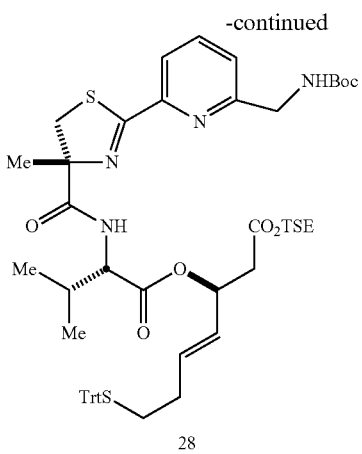

28

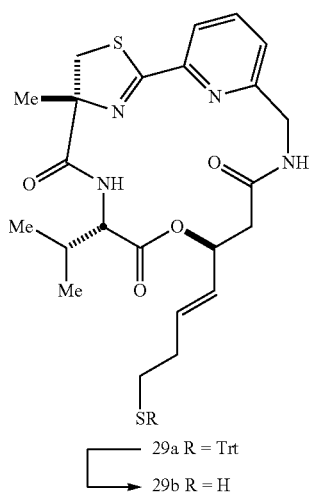

29a R = Trt
29b R = H

Acid 27

Amine 24 (Katsura, Y., et al. 1994 *J Med Chem* 37(1):57-66) was dissolved in $CH_2Cl_2$ and treated with 1.83 mL (1.31 mmol, 1.5 equiv.) $Et_3N$, followed by dropwise addition of a solution of 2.29 g (10.5 mmol, 1.2 equiv.) Boc anhydride in $CH_2Cl_2$. The resulting reaction was stirred overnight, then quenched with saturated aqueous $NaHCO_3$. The organic layer was separated, dried over $Na_2SO_3$, filtered, and concentrated to give the Boc protected amine as a white solid. This solid was then dissolved in 90 mL $CH_3OH$ together with 1.62 g (8.7 mmol, 1.0 equiv.) α-methyl cysteine and 2.44 mL (17.5 mmol, 2.0 equiv.) $Et_3N$. The resulting solution was heated at reflux overnight. The reaction was subsequently cooled to room temperature and the solvents removed in vacuo. The crude reaction mixture was then dissolved in saturated aqueous $NaHCO_3$ and washed with diethyl ether. The aqueous layer was then acidified to pH ~3-4 by dropwise addition of 3N HCl and extracted with EtOAc (3×30 mL). The combined organics were dried over $Na_2SO_4$, filtered, and concentrated to provide 0.500 g (1.4 mmol, 30% yield) of acid 27 in spectroscopically pure form. (27) $[\alpha]_D$: +55.2 (c=2, $CHCl_3$). $^1$H NMR (300 MHz, $CDCl_3$) δ 1.46 (s, 9H), 1.67 (s, 3H), 3.28 (d J=11.7 Hz, 1H), 3.81 (d J=11.7 Hz, 1H), 4.47 (d J=5.4Hz, 2H), 5.53 (s, 1H), 7.37 (d J=7.8 Hz, 1H), 7.74 (t J=7.8 Hz,

98

1H), 8.00 (d J=7.8 Hz, 1H). $^{13}$C NMR (100.6 MHz, $CDCl_3$): δ 21.9, 24.2, 28.6, 36.1, 40.5, 45.5, 47.9, 79.8, 85.1, 120.6, 123.9, 137.4, 149.9, 156.4, 157.4, 157.6, 171.3, 175.8.HRMS (ESI): m/z calcd. for $C_{16}H_{20}N_3Na_2O_4S$ $(M-H+2Na)^+$ 396.09699. found 396.09616.

Thiazoline-Pyridine Acyclic Precursor 28

1.100 g (1.3 mmol, 1.0 equiv.) diester 19 and 0.500 g (1.4 mmol, 1.1 equiv.) acid 27 were coupled according to the same procedure described above for synthesis of 43. 0.800 g (0.90 mmol, 59% yield) 28 was obtained after column chromatography. (28): Clear oil. $[\alpha]^{24}_D$: -22.1 (c=2, $CHCl_3$). $^1$H NMR (300 MHz, $CDCl_3$) δ 0.73 (d J=6.9Hz, 3H), 0.81 (d J=6.9Hz, 3H), 0.94-0.99 (m, 2H), 1.47 (s, 9H), 1.58 (s, 3H), 2.03-2.19 (m, 5H), 2.55 (dd J=5.7, 15.9Hz, 1H), 2.69 (dd J=8.1, 15.9Hz, 1H), 3.31 (d J=11.7 Hz, 1H), 3.69 (d J=11.7 Hz, 1H), 4.13-4.18 (m, 2H), 4.48-4.53 (m, 3H), 5.37 (dd J=7.5, 15.3Hz, 1H), 5.48-5.52 (m, 1H), 5.61-5.74 (m, 2H), 7.18-7.29 (m, 10H), 7.35-7.40 (m, 7H), 7.68 (t J=7.8 Hz, 1H), 7.98 (d J=7.8 Hz, 1H). $^{13}$C NMR (100.6 MHz, $CDCl_3$): δ -1.2, 17.5, 17.6, 19.3, 25.0, 28.7, 31.3, 31.5, 39.9, 40.8, 45.7, 56.9, 63.3, 66.8, 72.0, 79.8, 85.9, 120.2, 124.0, 126.8, 128.0, 128.1, 129.7, 134.2, 137.6, 145.0, 150.1, 156.3, 157.9, 169.9, 170.7, 171.2, 174.7. HRMS (ESI): m/z calcd. for $C_{52}H_{66}N_4NaO_7S_2Si$ $(M+Na)^+$ 973.40344. found 973.40443.

S-Trityl Macrocycle 29a

According to the general procedure, 0.400 g (0.42 mmol) 28 was deprotected and cyclized to provide 0.200 g (0.27 mmol, 64% yield) macrocycle 29a after column chromatography. Eluent: EtOAc. (29a): Clear oil. $[\alpha]^{24}_D$: +16.7 (c=1, $CHCl_3$). $^1$H NMR (300 MHz, 10:1 $CDCl_3$:$CD_3OD$) δ 0.52 (d J=6.9Hz, 3H), 0.74 (d J=6.9Hz, 3H), 1.84 (s, 3H), 2.03-2.17 (m, 5H), 2.64-2.79 (m, 2H), 3.38 (d J=11.4Hz, 1H), 4.09 (d J=11.4Hz, 1H), 4.30 (d J=17.7 Hz, 1H), 4.68 (dd J=3.9, 9.9Hz, 1H), 5.00 (dd J=6.6, 17.7 Hz, 1H), 5.40 (dd J=6.6, 15.6 Hz, 1H), 5.60-5.66 (m, 1H), 5.75 (dt J=7.8, 15.6 Hz, 1H), 7.10-7.37 (m, 18H), 7.64 (d J=7.5Hz, 1H), 7.80 (t J=7.5Hz, 1H). $^{13}$C NMR (100.6 MHz, 10:1 $CDCl_3$:$CD_3OD$): δ 16.2, 19.0, 24.5, 31.3, 31.5, 33.5, 38.7, 41.2, 43.4, 43.6, 51.4, 57.4, 66.7, 73.3, 84.3, 123.2, 124.7, 126.7, 128.0, 128.2, 129.7, 133.3, 138.2, 144.9, 148.7, 157.4, 166.0, 169.2, 170.0, 173.3, 173.6. HRMS (ESI): m/z calcd. for $C_{42}H_{44}N_4NaO_4S_2$ $(M+Na)^+$ 755.26962. found 755.26961.

Thiol 23b

According to the general procedure, 0.033 g 23a was deprotected to give 0.019 g 23b after preparative thin layer chromatography. (29b): Clear oil. $[\alpha]^{24}_D$: +3.4 (c=0.2, $CHCl_3$). $^1$H NMR (300 MHz, 10:1 $CDCl_3$:$CD_3OD$) δ 0.54 (d J=6.9Hz, 3H), 0.75 (d J=6.9Hz, 3H), 1.43 (t J=7.8 Hz, 1H), 1.89 (s, 3H), 2.04-2.17 (m, 1H), 2.32-2.39 (m, 2H), 2.49-2.57 (m, 2H), 2.69-2.86 (m, 2H), 3.39 (d J=11.4Hz, 1H), 4.10 (d J=11.4Hz, 1H), 4.37 (dd J=2.4, 17.7 Hz, 1H), 4.72 (dd J=3.9, 9.9Hz, 1H), 5.04 (dd J=6.9, 17.7 Hz, 1H), 5.57 (dd J=6.6, 15.6 Hz, 1H), 5.67-5.73 (m, 1H), 5.87 (dt J=7.2, 15.6 Hz, 1H), 7.38 (d J=7.8 Hz, 1H), 7.66 (d J=7.8 Hz, 1H), 7.84 (t J=7.8 Hz, 1H). $^{13}$C NMR (100.6 MHz, 10:1 $CDCl_3$:$CD_3OD$): δ 16.9, 19.2, 24.1, 24.8, 33.8, 36.7, 41.8, 43.8, 44.1, 51.4, 57.7, 72.5, 85.0, 123.5, 124.6, 128.6, 132.7, 138.1, 156.9, 169.0, 169.3, 173.6. HRMS (ESI): m/z calcd. for $C_{23}H_{30}N_4NaO_4S_2$ (M+Na)$^+$ 513.16007. found 513.16058.

Example 15

Synthesis of the Oxazoline-Oxazole Analog

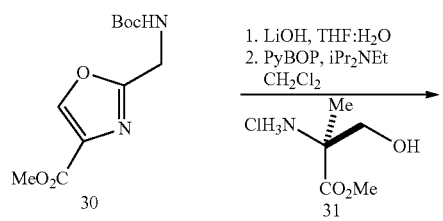

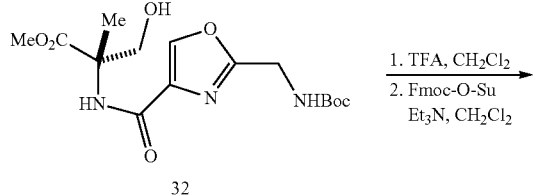

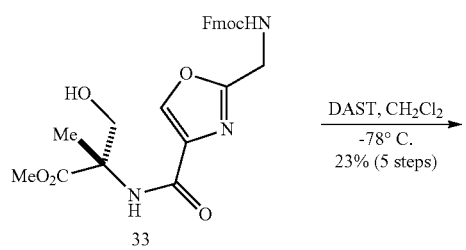

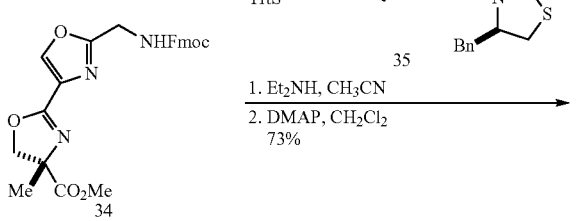

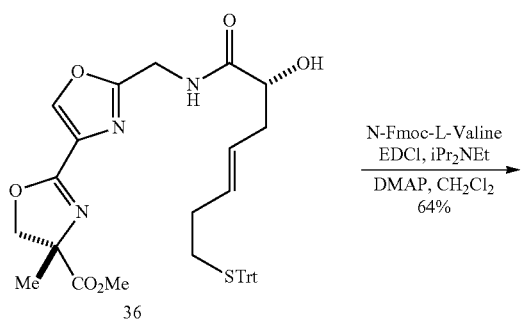

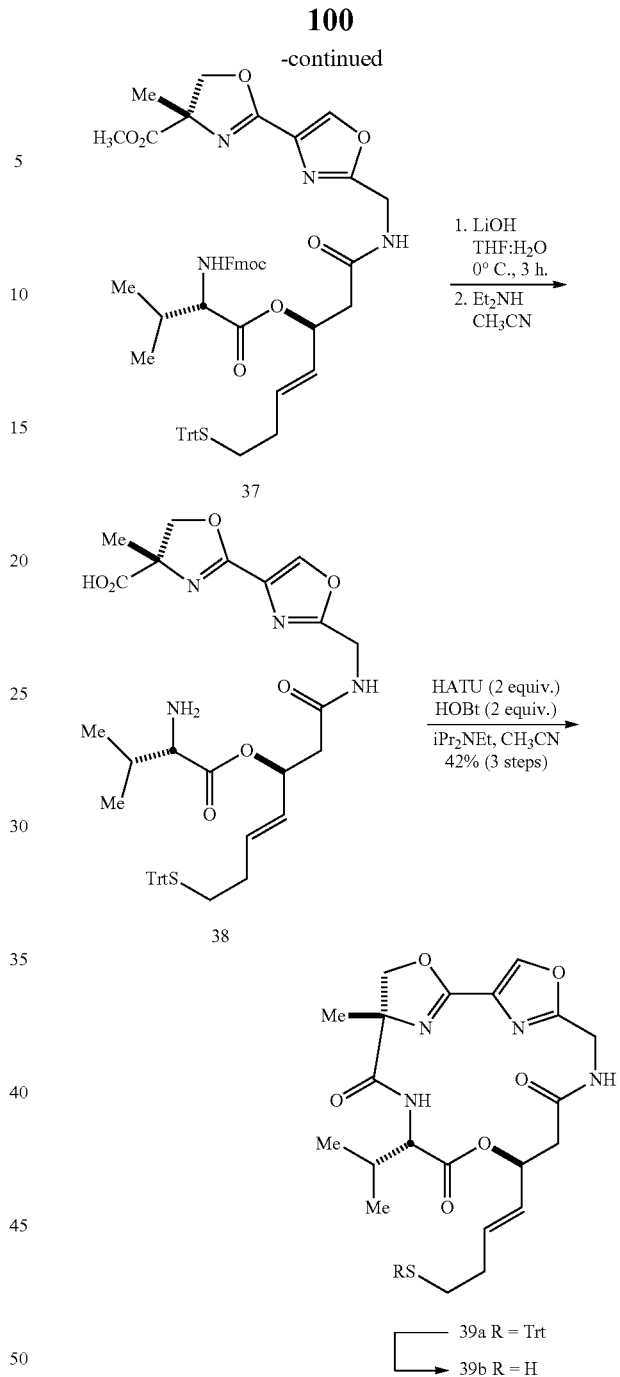

Oxazoline-oxazole 34

1.1 g (4.3 mmol, 1.0 equiv.) Oxazole 30 (Phillips, A. J., et al. 2000 *Org Lett* 2(8):1165-1168) was dissolved in 200 mL 2:1 THF:H$_2$O and treated with 0.205 g (8.6 mmol, 2.0 equiv.) LiOH. The resulting solution was stirred for ~1 hr., when TLC showed complete disappearance of starting material. The reaction was acidified with 1N HCl and extracted with CH$_2$Cl$_2$. The organic layer was dried over Na$_2$SO$_3$, filtered, and concentrated to give the crude acid, which was taken on without further purification. The acid was taken up in dry CH$_2$Cl$_2$. 4.47 g (8.6 mmol, 2.0 equiv.) PyBOP was added, followed by 0.874 g (5.2 mmol, 1.2 equiv.) α-methyl-serine-methylester-HCL salt (Avenoza, A., et al. 2001 *Tet Assym* 12(6):949-957) and 2.24 mL (12.9 mmol, 3.0 equiv.) iPr$_2$NEt.

The resulting reaction was stirred for ~2 hrs, then concentrated and passed through a short plug of silica, washing with EtOAc, to give alcohol 32.

Crude alcohol 32 was dissolved in 100 mL $CH_2Cl_2$ (to ~0.003M), cooled to 0° C., and treated with 14 mL TFA (to ~0.3M). The reaction was stirred for ~2 hrs, when TLC showed complete disappearance of starting material. The reaction mixture was concentrated, the residue dissolved in toluene, and concentrated again. The crude amine salt was dried on an oil pump for ~2 hrs, then dissolved in 50 mL dry $CH_2Cl_2$, cooled to 0° C., and treated successively with 0.720 mL (8.6 mmol, 2.0 equiv.) $Et_3N$ and 1.72 g (5.2 mmol, 1.2 equiv.) Fmoc-O-succinimide in 10 mL $CH_2Cl_2$. The resulting reaction was allowed to warm to room temperature and stirred overnight. The reaction was then quenched with saturated aqueous $NaHCO_3$, dried over $Na_2SO_3$, filtered, and concentrated. The residue was passed through a short plug of silica, washing with EtOAc to give alcohol 33.

Crude alcohol 33 was dissolved in 20 mL dry $CH_2Cl_2$ and cooled to −78° C. 0.690 mL (5.6 mmol, 1.2 equiv.) DAST was added dropwise and the reaction was allowed to stir at −78° C. for an additional 2 hrs. The mixture was then poured onto a saturated aqueous solution of $NaHCO_3$ at 0° C. The organic layer was separated, dried over $Na_2SO_3$, filtered, and concentrated. The residue was purified by column chromatography. An unidentified by-product elutes first in 1:1 hexanes:EtOAc, followed by the desired oxazoline 34 in 1:2 hexanes:EtOAc (0.455 g, 0.99 mmol, 23% yield from 30). (34): $[\alpha]^{24}_D$: +72.7 (c=1, $CHCl_3$). $^1$H NMR (300 MHz, $CDCl_3$) δ 1.62 (s, 3H), 3.78 (s, 3H), 4.17 (d J=8.7 Hz, 1H), 4.23 (t J=6.9Hz, 1H), 4.42-4.58 (m, 4H), 4.82 (d J=8.7 Hz, 1H), 5.54-5.57 (m, 1H), 7.31 (t J=7.5Hz, 2H), 7.40 (t J=7.5 Hz, 2H), 7.59 (d J=7.5Hz, 2H), 7.76 (d J=7.5Hz, 2H), 8.12 (s, 1H). $^{13}$C NMR (100.6 MHz, $CDCl_3$): δ 25.1, 38.5, 47.3, 53.1, 67.4, 74.5, 77.6, 120.2, 125.3, 127.3, 127.9, 130.4, 141.5, 142.0, 143.9, 156.5, 158.5, 162.3, 173.4. HRMS (ESI): m/z calcd. for $C_{25}H_{23}N_3NaO_6$ (M+Na)$^+$484.14791. found 484.14790.

Alcohol 36

0.250 g (0.54 mmol, 1.0 equiv.) 34 was dissolved in 30 mL $CH_3CN$ and treated with 3 mL $Et_2NH$. The reaction was allowed to stir for 2 hrs and then concentrated, redissolved in EtOAc, and concentrated again. The crude amine thus obtained was taken up in 5 mL dry $CH_2Cl_2$ together with 0.010 g (0.08 mmol, 0.15 equiv.) DMAP and added dropwise to a solution of 0.495 g (0.81 mmol, 1.5 equiv.) 35 in 20 mL $CH_2Cl_2$. The resulting reaction mixture was allowed to stir overnight, then concentrated and submitted immediately to column chromatography. 0.253 g (0.39 mmol, 73% yield) alcohol 36 eluted in 1:2 hexanes:EtOAc. (36): $[\alpha]^{24}_D$: −18.1 (c=1, $CHCl_3$). $^1$H NMR (300 MHz, $CDCl_3$) δ 1.61 (s, 3H), 2.03-2.10 (m, 2H), 2.16-2.22 (m, 2H), 2.38 (dd J=8.4, 15.3Hz, 1H), 2.46 (dd J=3.9, 15.3Hz, 1H), 3.77 (s, 3H), 4.17 (d J=9.0 Hz, 1H), 4.41-4.47 (m, 1H), 4.58 (d J=5.4Hz, 2H), 4.81 (d J=9.0 Hz, 1H), 5.41 (dd J=6.3, 15.6 Hz, 1H), 5.56 (dt J=6.9, 15.6 Hz, 1H), 6.63-6.66 (m, 1H), 7.17-7.30 (m, 9H), 7.37-7.41 (m, 6H), 8.11 (s, 1H). $^{13}$C NMR (100.6 MHz, $CDCl_3$): δ 25.2, 31.6, 31.7, 36.7, 43.0, 53.1, 66.8, 69.1, 74.4, 76.4, 126.8, 128.1, 129.8, 129.9, 130.2, 132.7, 142.1, 145.1, 158.6, 162.3, 172.4, 173.4. HRMS (ESI): m/z calcd. for $C_{36}H_{37}N_3NaO_6S$ (M+Na)$^+$662.22953. found 662.22913.

Oxazoline-oxazole Acyclic Precursor 37

0.250 g (0.39 mmol) of alcohol 36 and 0.663 g (2.0 mmol, 5 equiv.) N-Fmoc-L-valine were dissolved in 20 mL dry $CH_2Cl_2$. The reaction was cooled to 0° C., and 0.449 g (2.4 mmol, 6 equiv.) EDCI and 0.003 g (0.02 mmol, cat.) DMAP were added in ~5 mL $CH_2Cl_2$, followed by 0.4 mL $iPr_2NEt$. The reaction was allowed to warm to room temperature and stirred overnight, when TLC showed complete disappearance of 36. The reaction was concentrated and the product (0.240 g, 64% yield) purified by silica gel chromatography. Eluent: 1:2 hexanes:EtOAc. (37): $[\alpha]^{24}_D$: −2.0 (c=1, $CHCl_3$). $^1$H NMR (300 MHz, $CDCl_3$) δ 0.83 (d J=6.9 Hz, 3H), 0.90 (d J=6.9Hz, 3H), 1.58 (s, 3H), 1.64-1.73 (m, 1H), 2.00-2.18 (m, 5H), 2.49-2.62 (m, 2H), 3.76 (s, 3H), 4.12 (d J=8.7 Hz, 1H), 4.10-4.21 (m, 2H), 4.36 (d J=6.9Hz, 2H), 4.45-4.60 (m, 2H), 4.77 (d J=8.7 Hz, 1H), 5.34-5.42 (m, 2H), 5.58-5.71 (m, 2H), 6.50 (t J=5.1 Hz, 1H), 7.17-7.32 (m, 12H), 7.36-7.41 (m, 8H), 7.57 (d J=7.5Hz, 2H), 7.75 (d J=7.5Hz, 2H), 8.06 (s, 1H). $^{13}$C NMR (100.6 MHz, $CDCl_3$): δ 17.6, 17.9, 18.8, 19.3, 25.1, 31.2, 31.3, 31.5, 37.0, 41.5, 47.4, 53.1, 53.8, 59.4, 66.8, 67.1, 72.4, 74.5, 76.3, 120.2, 125.3, 126.8, 127.3, 127.9, 128.1, 129.8, 130.3, 134.1, 141.5, 142.0, 144.0, 144.1, 145.0, 156.6, 158.5, 162.0, 169.3, 171.3, 173.4. HRMS (ESI): m/z calcd. for $C_{56}H_{56}N_4NaO_9S$ (M+Na)$^+$983.36602. found 983.36673.

S-Trityl Macrocycle 39a 0.240 g (0.25 mmol, 1.0 equiv.) acyclic precursor 37 was dissolved in 7.5 mL 4:1 THF:$H_2O$ and cooled to 0° C. 0.5 mL of a 0.5M aqueous solution of LiOH was added dropwise, and the resulting reaction mixture was allowed to stir for ~3 hrs at 0° C., when TLC demonstrated disappearance of the starting material. The reaction was neutralized by dropwise addition of 1N HCl and extracted with $CH_2Cl_2$. The combined organics were dried and filtered and solvents evaporated to provide the crude acid. This was immediately dissolved in 25 mL $CH_3CN$ (to ~0.01M) and treated with 1.25 mL $Et_2NH$ (to ~0.2M). The reaction was stirred for ~2 hrs, when the reaction was assumed to be complete. The resulting solution was concentrated, taken up in EtOAc, and concentrated again. The crude amino acid was dried on the mechanical pump overnight and then submitted to cyclization conditions as described above. Column chromatography provided 0.074 g (0.10 mmol, 74% yield) macrocycle 39a as a clear oil. (39a): $[\alpha]^{24}_D$: +42.2 (c=1, $CHCl_3$). $^1$H NMR (300 MHz, $CDCl_3$) δ 0.53 (d J=6.9Hz, 3H), 0.56 (d J=6.9Hz, 3H), 1.58 (s, 3H), 1.89-2.16 (m, 5H), 2.51 (dd J=1.8, 17.1 Hz, 1H), 2.87 (dd J=9.9, 17.1 Hz, 1H), 3.82 (dd J=3.6, 17.7 Hz, 1H), 3.99 (d J=9.0 Hz, 1H), 4.32-3.36 (m, 1H), 4.62 (d J=9.0 Hz, 1H), 4.60-4.69 (m, 1H), 5.34-5.49 (m, 2H), 5.58 (dt J=6.9, 14.7 Hz, 1H), 7.08-7.21 (m, 9H), 7.26-7.31 (m, 7H), 7.62-7.67 (m, 1H), 7.97 (s, 1H). $^{13}$C NMR (100.6 MHz, 10:1 $CDCl_3$:$CD_3OD$): δ 17.1, 18.7, 21.1, 31.4, 34.0, 37.4, 39.9, 58.0, 66.8, 72.7, 73.6, 77.5, 78.8, 126.8, 128.0, 128.4, 129.2, 129.7, 133.2, 141.7, 144.9, 162.2, 164.1, 168.7, 171.9, 174.3. HRMS (ESI): m/z calcd. for $C_{40}H_{42}N_4NaO_6S$ (M+Na)$^+$ 729.27173. found 729.27147.

Disulfide Dimer 39b

To a vigorously stirring solution of 0.319 g (1.3 mmol, 12 equiv.) $I_2$ in 300 mL 10% MeOH/$CH_2Cl_2$ was added 0.074 g (0.10 mmol, 1.0 equiv.) protected thiol 39a in 60 mL 10% MeOH/$CH_2Cl_2$ dropwise over 10 minutes. The resulting mixture was stirred for a further 10 minutes. 250 mL 0.01 N $Na_2S_2O_3$ was added and the organic phase extracted with $CH_2Cl_2$ the combined organic extract washed with brine, dried over $Na_2SO_3$, filtered, and the solvent removed. The residue was purified by flash chromatography, washing first with EtOAC, then 10:1 $CH_2Cl_2$:$CH_3OH$. (39b): Clear oil. $[\alpha]^{24}_D$: +19.0 (c=0.5, $CHCl_3$). $^1$H NMR (300 MHz, $CDCl_3$) d 0.67-0.70 (m, 6H), 1.66 (s, 3H), 2.12-2.18 (m, 1H), 2.40-2.47 (m, 2H), 2.71-2.80 (m, 3H), 3.02 (dd J=9.6, 16.5Hz, 1H), 3.96 (dd J=4.5, 17.4Hz, 1H), 4.05 (d J=9.0 Hz, 1H), 4.51 (dd J=3.6, 8.7 Hz, 1H), 4.73 (d J=9.0 Hz, 1H), 4.85 (dd J=9.0, 17.4Hz, 1H), 5.54-5.69 (m, 2H), 5.90 (dt J=6.9, 15.6 Hz, 1H), 6.89-6.94 (m, 1H), 8.01 (s, 1H). $^{13}$C NMR (100.6 MHz, 10:1 $CDCl_3$:$CD_3OD$): δ 17.4, 18.7, 21.4, 29.8, 31.9, 34.1, 37.6, 38.0, 40.3, 51.4, 58.1, 72.4, 74.0, 78.9, 128.5, 129.8, 133.7, 141.2, 161.0, 164.2, 168.7, 170.8, 174.1. HRMS (ESI): m/z calcd. for $C_{42}H_{54}N_8NaO_{12}S_2$ (M+Na)$^+$949.31948. found 949.32045.

Example 16

HDAC Biochemical Assay

The inhibitory effect of compounds on deacetylase isoenzyme function was determined in vitro using an optimized homogenous assay performed in 384-well plate format. In this assay, recombinant, full-length HDAC protein (HDAC1 3.33 ng/μL, HDAC2 1 ng/μL, HDAC3/NCor2 0.17 ng/μL, HDAC6 1.3 ng/μL; BPS Biosciences) is incubated with a commercially-available fluorophore conjugated substrate at a concentration equivalent to the substrate $K_m$ (Upstate 17-372; 6 μM for HDAC1, 3 μM for HDAC2, 6 μM for HDAC3 and 16 μM for HDAC6). Reactions are performed in assay buffer (50 mM HEPES, 100 mM KCl, 0.001% Tween-20, 0.05% BSA, 200 μM TCEP, pH 7.4) and followed for fluorigenic release of 7-amino-4-methylcoumarin from substrate upon deacetylase and trypsin enzymatic activity. Fluorescence measurements are obtained approximately every five minutes using a multilabel plate reader and plate-stacker (Envision; Perkin-Elmer). Data are analyzed on a plate-by-plate basis for the linear range of fluorescence over time. Data from the plate capture corresponding to the mid-linear range is imported into analytical software and annotated with well identity and compound concentration (Spotfire DecisionSite). Replicate experimental data from incubations with inhibitor are normalized to control, solvent-only wells and IC-50 is deteremined by logistic regression.

Thus, small-molecule inhibitors were arrayed at twelve-point dose-response (3-fold increments) in 384-well library plates and transferred by robotic pin device to replicate assay plates containing assay buffer under reducing conditions (TCEP 200 μM). A liquid handling device then transferred a tripeptide substrate terminating in acetyl-lysine and amide conjugated to 4-methyl-7-aminocoumarin (AMC), recombinant human histone deacetylase (BPS Bioscience, San Diego, Calif.), and recombinant human trypsin (Sigma-Aldrich, St. Louis, Mo.). Following deacetylase hydrolysis of acetyl-lysine, trypsin cleavage liberated the AMC fluorophore. Kinetic (fluorescence per unit time) and end-point (total fluorescence) data were captured by a multilabel plate reader. Replicate data were analyzed by curve-fit using logistic regression (Snotfire Decision—Site). A summary of assay data are in Table 4, below.

TABLE 4

Biochemical inhibition of human HDACs ($IC_{50}$, μm).

| Compound | HDAC1 | HDAC2 | HDAC3 | HDAC6 |
|---|---|---|---|---|
| Largazole thiol (1b) | 0.0012 | 0.0035 | 0.0034 | 0.049 |
| Enantiomer (2) | 1.2 | 3.1 | 1.9 | 2.2 |
| C-2 epimer (3) | 0.030 | 0.082 | 0.084 | 0.68 |
| Proline substitution (4) | 0.11 | 0.80 | 0.58 | 13 |
| Largazole-Azumamide hybrid (9b) | >30 | >30 | >30 | >30 |
| Benzamide (11b) | 0.27 | 4.1 | 4.1 | >30 |
| Benzamide (12b) | 23 | 29 | 14 | >30 |
| Thioamide (13b) | 0.67 | 1.6 | 0.96 | 0.7 |
| Thioamide (14b) | 1 | 1.9 | 1.5 | 0.24 |
| Cysteine substitution 22b | 0.0019 | 0.0048 | 0.0038 | 0.13 |
| Thiazole-thiazole (23b) | 0.077 | 0.12 | 0.085 | >30 |
| Thiazole-pyridine substitution (29b) | 0.00032 | 0.00086 | 0.0011 | 0.029 |
| Oxazoline-oxazole (39b) | 0.00069 | 0.0017 | 0.0015 | 0.045 |
| MS-275 | 0.045 | 0.13 | 0.17 | >30 |

Several striking observations emerge from this dataset. The Largazole enantiomer (2) exhibits a decrease in potency by almost exactly three orders of magnitude for all isoforms tested, underscoring the obligate, stereochemical and conformation-activity relationship between the natural product and its protein targets. This is further substantiated by the intermediate potency of the C-2 epimer (3), the valine-to-proline substitution (4) and the oxidized and strained thiazole-thiazole derivative (23b). Of note, the single-atom substitutions of the sulfur atoms for oxygen atoms in the oxazoline-oxazole derivative (29b) provided a compound equipotent to Largazole itself.

The synthetic approach described herein allowed rapid diversification of the zinc-binding arm, modulating both potency and specificity (as for lib, 12b, 13b and 14b). A significant increase in potency was observed with pyridine substitution of the thiazole; this compound (29b) possesses sub-nanomolar activity against Class I HDACs. Compound 29b constitutes a highly biochemically potent Class I HDAC inhibitor—between three and four times more potent than Largazole itself against HDACs 1, 2 and 3. Notably, the methyl substituent of the thiazoline ring has been demonstrated to be non-essential for the dramatic potency of the natural product (cf. 22b).

The commercial availability of relatively inexpensive cysteine, compared with that of the α-methylcysteine residue of natural Largazole, permitted for a reduction in the overall synthetic approach to 22b by four steps, establishing a high-yielding, scalable, five-step synthesis of this agent. This highly efficient synthesis is compatible with further derivitization and potential for practical scale-up endeavors. Additionally provided herein is additional insight into the structural, functional, stereochemical, and conformational aspects of the Largazole molecular scaffold that constitutes the basis for the further design and synthesis of extraordinarily potent HDAC inhibitors with potential therapeutic significance.

The invention claimed is:

1. A compound of Formula (I)

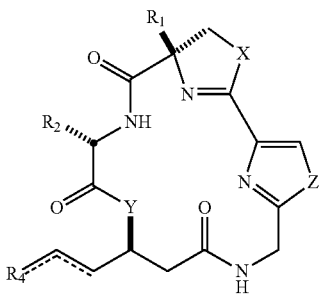

wherein X is S or O;
Y is NR, wherein R is H, lower alkyl, or lower arylalkyl;
Z is S or O;
$R_1$ is H, lower alkyl, or lower arylalkyl;
$R_2$ is lower alkyl, isopropyl, n-propyl, cyclopropyl, isobutyl, n-butyl, sec-butyl, or tert-butyl;
$R_4$ is H, $(CH_2)_n COOH$, $(CH_2)_n CONHR$, $(CH_2)_n CONHOH$, $(CH_2)_n SR_3$, $SR_5$ (wherein $R_5$ is lower alkyl or lower aryl),

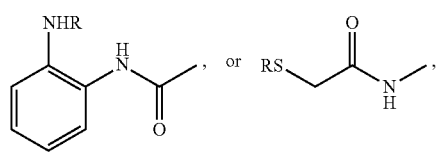

wherein n is at least 1, and wherein R₃ is H, octanoyl, acyl, SR, a higher acyl derivative, or

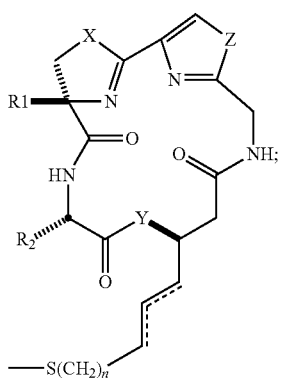

or a pharmaceutically acceptable salt, solvate, clathrate, prodrug, or stereoisomer thereof.

2. The compound of claim 1, having the Formula (III)

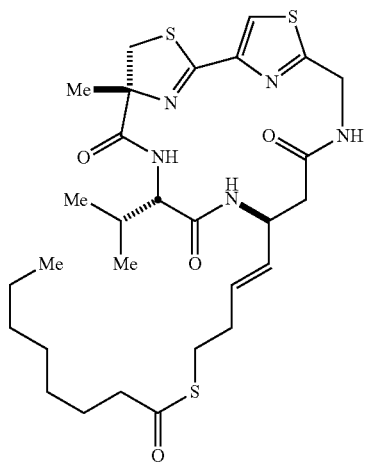

or a pharmaceutically acceptable salt, solvate, clathrate, prodrug, or stereoisomer thereof.

3. The compound of claim 1, having the Formula (VIII)

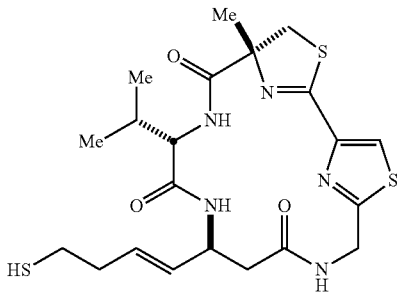

or a pharmaceutically acceptable salt, solvate, clathrate, prodrug, or stereoisomer thereof.

4. A pharmaceutical composition comprising a therapeutically effective amount of the compound of claim 1 and at least one pharmaceutically acceptable excipient for treating cancer in a subject.

5. The pharmaceutical composition of claim 4, wherein the subject is human.

6. The compound of claim 1, wherein $R_1$ is H or lower alkyl.

7. The compound of claim 1, wherein $R_1$ is methyl.

8. The compound of claim 1, wherein $R_2$ is lower alkyl.

9. The compound of claim 1, wherein $R_2$ is isopropyl.

10. The compound of claim 1, wherein X is S.

11. The compound of claim 1, wherein Z is S.

* * * * *